United States Patent [19]
Weller et al.

[11] Patent Number: 5,990,254
[45] Date of Patent: Nov. 23, 1999

[54] METALLOCENES AS CATALYSTS IN THE PREPARATION OF CYCLOOLEFIN COPOLYMERS

[75] Inventors: Thomas Weller, Mainz; Michael Aulbach, Hofheim; Frank Küber, Oberursel; Gerhard Erker; Christian Psiorz, both of Münster; Bernd Bachmann, Eppstein; Frank Osan, Kelkheim, all of Germany

[73] Assignee: Targor GmbH, Germany

[21] Appl. No.: 08/780,179

[22] Filed: Dec. 26, 1996

Related U.S. Application Data

[62] Division of application No. 08/712,681, Sep. 13, 1996, Pat. No. 5,710,297, which is a continuation of application No. 08/361,423, Dec. 21, 1994, abandoned.

[30] Foreign Application Priority Data

| Dec. 21, 1993 | [DE] | Germany | 43 43 566 |
| Dec. 24, 1993 | [DE] | Germany | 43 44 631 |
| Sep. 14, 1994 | [DE] | Germany | 44 32 617 |

[51] Int. Cl.$^6$ ................................................. C08F 232/04
[52] U.S. Cl. ........................ 526/160; 526/127; 526/161; 526/170; 526/281; 526/943
[58] Field of Search .................... 526/160, 170, 526/281, 943, 127, 161

[56] References Cited

U.S. PATENT DOCUMENTS

| 4,931,417 | 6/1990 | Miya et al. . | |
| 5,003,019 | 3/1991 | Ishimaru et al. | 526/281 |
| 5,008,228 | 4/1991 | Chang | 502/111 |
| 5,087,677 | 2/1992 | Brekner et al. | 526/160 |
| 5,122,583 | 6/1992 | Ewen et al. | 526/125 |
| 5,145,819 | 9/1992 | Winter et al. . | |
| 5,268,495 | 12/1993 | Riepl et al. | 556/11 |
| 5,278,264 | 1/1994 | Spaleck et al. . | |
| 5,308,811 | 5/1994 | Suga et al. | 502/62 |
| 5,331,057 | 7/1994 | Brekner et al. | 525/289 |
| 5,359,001 | 10/1994 | Epple et al. | 525/97 |
| 5,376,725 | 12/1994 | Epple et al. | 526/281 X |
| 5,442,020 | 8/1995 | Davis et al. | 526/127 |
| 5,491,205 | 2/1996 | Langhauser et al. | 526/121 |

FOREIGN PATENT DOCUMENTS

| 1317411 | 5/1993 | Canada . |
| 2095100 | 10/1993 | Canada . |
| 0 490 256 | 6/1972 | European Pat. Off. . |
| 0 129 368 | 12/1984 | European Pat. Off. . |
| 0 277 003 | 8/1988 | European Pat. Off. . |
| 0 277 004 | 8/1988 | European Pat. Off. . |
| 0 283 164 | 9/1988 | European Pat. Off. . |
| 0 302 424 | 2/1989 | European Pat. Off. . |
| 0 316 155 | 5/1989 | European Pat. Off. . |
| 0 351 392 | 1/1990 | European Pat. Off. . |
| 0 407 870 A2 | 1/1991 | European Pat. Off. . |
| 0 426 638 | 5/1991 | European Pat. Off. . |
| 0 427 697 | 5/1991 | European Pat. Off. . |
| 0 485 823 | 5/1992 | European Pat. Off. . |
| 0528287 | 2/1993 | European Pat. Off. . |
| 528 041 | 2/1993 | European Pat. Off. . |
| 0 530 647 | 3/1993 | European Pat. Off. . |
| 0 560 090 A1 | 9/1993 | European Pat. Off. . |
| 0 566 988 A1 | 10/1993 | European Pat. Off. . |
| 0 578 838 | 1/1994 | European Pat. Off. . |
| 0 610 851 A1 | 8/1994 | European Pat. Off. . |
| 0 650 981 | 10/1994 | European Pat. Off. . |
| 0 650 973 | 5/1995 | European Pat. Off. . |
| 721954 | 7/1996 | European Pat. Off. . |
| 93/20113 | 10/1993 | WIPO . |

OTHER PUBLICATIONS

Erickson et al, "Syntheses of Dipentafulvenes: Bichromophoric Effects Correlated with Structure", J. Org. Chem., vol. 57, No. 8, pp. 2504–2508 (1992).

S. Pasynkiewicz, "Alumoxanes: Synthesis, structures, complexes and reactions", Polyhedron, vol. 9, No. 23, pp. 429–453, (1990).

Keith J. Stone and R. Daniel Little, "An Exceptionally Simple and Efficient Method for the Preparation of a Wide Variety of Fulvenes", The Journal of Organic Chemistry, vol. 49, No. 11, pp. 1849–1853 (Jun. 1, 1984).

H. Stetter and H.J. Bender, "Addition von Aldehyden an aktivierte Doppelbindungen, XXIX, Neue Methode zur Darstellung symmetrischer 1,4–Diketone", Chem. Ber. 114, pp. 1226–1233, (1981).

Shaochun You and Markus Neuenschwander, "Oxidative Coupling of 6,6–Dimethylfulvenyl Anion", Forschung, Chimia 46, pp. 377–380, (1992).

H. Stetter und H. Kuhlmann, "Addition von Aldehyden an aktivierte Doppelbindungen, XI", Chem. Ber. 109, pp. 3426–3431, (1976).

H. Stetter und M. Schreckenberg, "Eine neue Methode zur Addition von Aldehyden an aktivierte Doppel–bindungen, IV1)", Chem. Ber. 107, pp. 2453–2458, (1974).

M. Neuenschwander, "Novel–Chiral Ansa–Metallocene Complexes with Semi–Rigid Condensed Cyclic Bridge", Makromol. Chem. 183, p. 359, (1982).

Erker, Gerhard, et. al. "Synthesis of a Novel Annulated $C_1$–Bridged ansa–Metallocene System", Chem. Ber. 127 pp. 1551–1553 (1994).

European Search Report No. 94120162.6, Feb. 27, 1995.

Mise et al., "Excellent Stereoregular Isotactic Polymerizations of Propylene with $C_2$–Symmetric Silylene–Bridged Metallocene Catalysts" Chemistry Letters pp. 1853–1856 (1989).

Tagungsband der 1st Journal of Organometallic Chemistry Conference on Applied Organometallic Chemistry, "Novel – Chiral Ansa–Metallocene Complexes with Semi–rigid Condensed Cyclic Bridge" Seite 136 (1982).

*Primary Examiner*—Fred Teskin
*Attorney, Agent, or Firm*—Connolly Bove Lodge & Hutz LLP

[57] ABSTRACT

The present invention relates to a stereorigid metallocene compound containing, as ligands, at least two substituted or unsubstituted cyclopentadienyl groups which are bonded to one another via a monocyclic or polycyclic ring system, where at least one cyclopentadienyl group is fused to the monocyclic or polycyclic ring system, and to a process for the preparation of a cycloolefin copolymer. The cycloolefin copolymers obtained in this way have high tear strengths and are suitable for the production of extrusion parts and injection moldings.

19 Claims, No Drawings

METALLOCENES AS CATALYSTS IN THE PREPARATION OF CYCLOOLEFIN COPOLYMERS

This application is a divisional of application Ser. No. 08/712,681 filed Sep. 13, 1996, now U.S. Pat. No. 5,710,297, which is a continuation of Ser. No. 08/361,423, now abandoned, filed Dec. 21, 1994 now abandoned.

The present invention relates to a stereorigid metallocene compound whose ligands are bonded to one another in a specific manner. The novel compound can advantageously be employed as catalyst component in the preparation of transparent cycloolefin copolymers having high tear strengths.

The literature discloses the preparation of polyolefins using soluble metallocene compounds in combination with aluminoxanes or other cocatalysts which, due to their Lewis acidity, are able to convert neutral metallocene into a cation and stabilize it (EP 129 368, EP 351 392).

In the published proceedings of the 1st Journal of Organometallic Chemistry Conference on Applied Organometallic Chemistry, page 136, ansa-metallocene complexes are described which contain, as ligand system, a substituted tricyclic hydrocarbon.

It is known from the literature that cycloolefin homopolymers and copolymers can be prepared using metallocene/aluminoxane catalyst systems (EP 283 164 and EP 407 870). The polymerization of cycloolefins proceeds with retention of the rings and can be carried out in solvents or in bulk. Examples of solvents employed are hydrocarbons.

Cycloolefin copolymers can be prepared with a high content of cycloolefin and then have a high glass transition temperature, and consequently high heat distortion resistance, making these polymers suitable for use as thermoplastic molding compositions.

Cycloolefin copolymers prepared by means of metallocene technology can have two distinct series of properties. Cycloolefin copolymers prepared using mirror-symmetrical metallocenes have relatively low yield stresses. By comparison, cycloolefin copolymers prepared using $C_2$-symmetrical or asymmetrical metallocenes are distinguished by high yield stresses. However, all metallocenes known hitherto which are suitable for the preparation of cycloolefin copolymers having high yield stresses have unsatisfactory polymerization activity (EP 610 851). Accordingly, large amounts of catalyst must be employed in the polymerization, causing high preparation costs for the target cycloolefin copolymers. In addition, the use of ethylene as comonomer frequently results in the formation, as byproducts, of partially crystalline ethylene polymers, which can significantly impair the transparency of the cycloolefin copolymers.

The object of the invention was therefore to provide a metallocene compound which avoids the disadvantages of the prior art and which gives, in particular with high catalyst activity, cycloolefin copolymers which have high tear strengths and in addition are transparent.

It has been found that the use of a specifically bridged metallocene compound allows this object to be achieved.

The present invention relates to a stereorigid metallocene compound which contains, as ligands, at least two substituted or unsubstituted cyclopentadienyl groups which are bonded to one another via a monocyclic or polycyclic ring system, where at least one cyclopentadienyl group is fused to the monocyclic or polycyclic ring system, and where metallocenes containing a 4-($\eta^5$-3'-alkylcyclopentadienyl)-4,6,6-trimethyl($\eta^5$-2-alkyl-4,5-tetrahydropentalene) as ligand system are excluded.

When determining the number of ring atoms in the monocyclic or polycyclic ring system, the carbon atoms of the cyclopentadienyl group(s) fused to the ring system which, due to the fusing, are parts of the ring system are also counted. Substituents on the monocyclic or polycyclic ring system are not counted.

In a preferred embodiment, one cyclopentadienyl group is a substitutent on the monocyclic or polycyclic ring system (ie. the cyclopentadienyl group is bonded to the ring system via a covalent bond), while a further cyclopentadienyl group is fused to the monocyclic or polycyclic ring system.

The monocyclic or polycyclic ring system may be aromatic, aliphatic or mixed aromatic and aliphatic and may also contain heteroatoms, such as nitrogen, oxygen, sulfur, silicon or germanium. It preferably contains 6–40, particularly preferably 6–20, ring atoms, in particular carbon ring atoms. The monocyclic or polycyclic ring system may also carry substituents, such as a $C_1$–$C_{40}$-hydrocarbon-containing group.

Fused cyclopentadienyl groups are monofused (for example via the 1,2- or 1,3-position of the cyclopentadienyl ring) or polyfused (for example via the 1,2,3- or 1,2,3,4-position of the cyclopentadienyl ring), preferably monofused, to the mono- or polycyclic ring system.

The central unit $M^1R^x_n$ of the metallocene compound according to the invention preferably comprises a transition-metal atom $M^1$, in particular from group IIIb, IVb, Vb or VIb of the Periodic Table of the Elements, which carries n substituents $R^x$, which are identical or different and are preferably a $C_1$–$C_{40}$-hydrocarbon-containing group, a halogen atom, an OH group or a hydrogen atom. The total of the number of substituents $R^x$ and the number of substituted or unsubstituted cyclopentadienyl groups (ligands) corresponds to the valency of the transition-metal atom $M^1$.

Preference is given to compounds of the formula I

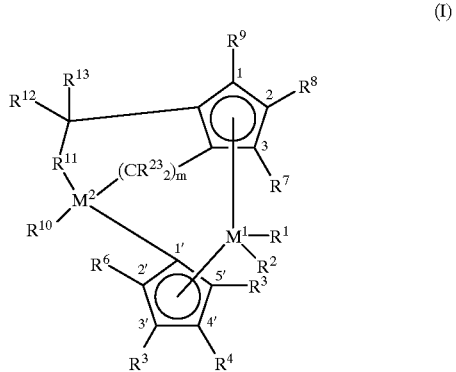

(I)

in which $M^1$ is a metal from group IIIb, IVb, Vb or VIb of the Periodic Table, $M^2$ is carbon, silicon, or germanium, $R^1$ and $R^2$ are identical or different and are a hydrogen atom, a $C_1$–$C_{40}$-hydrocarbon-containing group, such as a $C_1$–$C_{10}$-alkyl group, a $C_1$–$C_{10}$-alkoxy group, a $C_6$–$C_{10}$-aryl group, a $C_6$–$C_{25}$-aryloxy group, a $C_2$–$C_{10}$-alkenyl group, a $C_7$–$C_{40}$-arylalkyl group or a $C_7$–$C_{40}$-arylalkenyl group, an OH group, a halogen atom or $NR^{14}_2$, in which $R^{14}$ is a halogen atom, a $C_1$–$C_{10}$-alkyl group or a $C_6$–$C_{10}$-aryl group, or $R^1$ and $R^2$ together with the atoms connecting them, form a ring system, $R^3$, $R^4$, $R^5$, $R^6$, $R^7$, $R^8$ and $R^9$ are identical or different and are a hydrogen atom, a halogen atom, a $C_1$–$C_{20}$-hydrocarbon-containing group, such as a $C_1$–$C_{10}$-alkyl group, which may be halogenated, a $C_6$–$C_{20}$-aryl group, a $C_6$–$C_{20}$-aryloxy group, a $C_2$–$C_{12}$-alkenyl group, a $C_7$–$C_{40}$-arylalkyl group, a $C_7$–$C_{40}$-alkylaryl group or a $C_8$–$C_{40}$-arylalkenyl group, a —$SiR^{14}_3$, —$NR^{14}_2$, —$SiOR^{14}_3$, —SiSR$^{14}_3$, or —PR$^{14}_2$ radical, in which R$^{14}$ is a halogen atom, a C$_1$–C$_{10}$-alkyl group or a C$_6$–C$_{10}$-aryl group, or two or more adjacent radicals R$^3$, R$^4$, R$^5$, R$^6$, R$^7$, R$^8$ and R$^9$, together with the atoms connecting them, form a ring system preferably containing 4–40, particularly preferably 6–15, carbon atoms, R$^{10}$ is a hydrogen atom, a C$_1$–C$_{40}$-hydrocarbon-containing group, such as a C$_1$–C$_{20}$ alkyl group, a C$_1$–C$_{10}$-alkoxy group, a C$_6$–C$_{20}$-aryl group, a C$_6$–C$_{20}$-aryloxy group, a C$_2$–C$_{12}$-alkenyl group, a C$_7$–C$_{40}$-arylalkyl group, a C$_7$–C$_{40}$-alkylaryl group or a C$_8$–C$_{40}$-arylalkenyl group, each of which may carry —NR$^{14}_3$, —SiR$^{14}_3$, —SR$^{14}_2$ or —OSiR$^{14}_3$ radicals, in which R$^{14}$ is a halogen atom, a C$_1$–C$_{10}$-alkyl group or a C$_6$–C$_{10}$-aryl group, or R$^{10}$ is connected to one or more of the radicals R$^3$, R$^4$, R$^5$ and R$^6$, R$^{11}$ is

[structural formulas]

wherein n is an integer from 1 to 20, l is an integer from 0 to 20, X is O, =NR$^{14}$, =CO, =PR$^{14}$, =P(O)R$^{14}$, =SO, =SO$_2$ or —S—, in which R$^{14}$ is a halogen atom, a C$_1$–C$_{10}$-alkyl group or a C$_6$–C$_{10}$-aryl group, R$^{15}$ and R$^{16}$ are identical or different and are a hydrogen atom, a halogen atom or a C$_1$–C$_{40}$-hydrocarbon-containing group, such as a C$_1$–C$_{10}$-alkyl group, a C$_1$–C$_{10}$-fluoroalkyl group, a C$_1$–C$_{10}$-alkoxy group, a C$_6$–C$_{10}$-aryl group, a C$_6$–C$_{10}$-fluoroaryl group, a C$_6$–C$_{10}$-aryloxy group, a C$_2$–C$_{10}$-alkenyl group, a C$_7$–C$_{10}$-arylalkyl group, a C$_7$–C$_{40}$-alkylaryl group, or a C$_8$–C$_{40}$-arylalkenyl group or two radicals R$^{15}$, two radicals R$^{16}$ or R$^{15}$ and R$^{16}$, in each case together with the atoms connecting them, form one or more rings, and M$^3$ is silicon, germanium or tin, R$^{12}$ and R$^{13}$ are identical or different and are a hydrogen atom, a C$_1$–C$_{40}$-hydrocarbon-containing group, such as a C$_1$–C$_{20}$-alkyl group, a C$_1$–C$_{10}$-alkoxy group, a C$_6$–C$_{20}$-aryl group, a C$_6$–C$_{20}$-aryloxy group, a C$_2$–C$_{12}$-alkenyl group, a C$_7$–C$_{40}$-arylalkyl group, a C$_7$–C$_{40}$-alkylaryl group or a C$_8$–C$_{40}$-arylalkenyl group, each of which may carry —NR$^{14}_3$, —SR$^{14}_2$, —SiR$^{14}_3$ or —OSiR$^{14}_3$ radicals, in which R$^{14}$ is a halogen atom, a C$_1$–C$_{10}$-alkyl group or a C$_6$–C$_{10}$-aryl group, or may carry halogen, R$^{23}$ is identical or different and is a hydrogen atom, a halogen atom or a C$_1$–C$_{40}$-hydrocarbon-containing group, such as a C$_1$–C$_{10}$-alkyl group, a C$_1$–C$_{10}$-alkoxy group, a C$_6$–C$_{10}$-aryl group, a C$_6$–C$_{25}$-aryloxy group, a C$_2$–C$_{10}$-alkenyl group, a C$_7$–C$_{40}$-arylalkyl group or a C$_7$–C$_{40}$-arylalkenyl group, or one or more radicals R$^{23}$ are bonded to one or both radicals R$^{15}$ and R$^{16}$ and/or to one or more radicals R$^{10}$, R$^{11}$, R$^{12}$ and R$^{13}$, and m is an integer from 0 to 24, where, in the case where M$^2$ is C, m is 0 and R$^{11}$ is CH$_2$, at least one of the radicals R$^4$, R$^8$, R$^{10}$, R$^{12}$ and R$^{13}$ is not alkyl and/or at least one of the radicals R$^3$, R$^5$, R$^6$, R$^7$ and R$^9$ is not hydrogen.

For compounds of the formula I, it is preferred that

M$^1$ is zirconium or hafnium, in particular zirconium,

R$^1$ and R$^2$ are identical and are a C$_1$–C$_3$-alkyl group or a halogen atom, in particular chlorine, R$^3$, R$^4$, R$^5$, R$^6$, R$^7$, R$^8$ and R$^9$ are identical or different and are a hydrogen atom, a C$_1$–C$_{10}$-alkyl group or a C$_6$–C$_{24}$-aryl group, or two or more adjacent radicals, together with the atoms connecting them, form an aromatic or aliphatic hydrocarbon ring system, R$^{10}$ is a hydrogen atom, a C$_6$–C$_{24}$-aryl group or a C$_1$–C$_{10}$-alkyl group, in particular a C$_1$–C$_4$-alkyl group, R$^{11}$ is

R$^{11}$

[structural formula]

wherein n is an integer from 1 to 8, in particular from 2 to 4,

R$^{15}$ and R$^{16}$ are identical or different and are hydrogen or a C$_1$–C$_{10}$-alkyl group, or two radicals R$^{15}$, two radicals R$^{16}$ or R$^{15}$ and R$^{16}$, together with the atoms connecting them, form a hydrocarbon ring system, M$^2$ is carbon, R$^{12}$ and R$^{13}$ are identical or different and are a hydrogen atom, a C$_1$–C$_{10}$-alkyl group, in particular a C$_1$–C$_4$-alkyl group, or a C$_6$–C$_{10}$-aryl group, and m is 0.

Particular preference is given to compounds of the formula I in which

M$^1$ is zirconium,

R$^1$ and R$^2$ are identical and are a halogen atom, in particular chlorine,

R$^3$, R$^4$, R$^5$, R$^6$, R$^7$, R$^8$ and R$^9$ are identical or different and are hydrogen or a C$_1$–C$_4$-alkyl group, such as methyl, ethyl, propyl, isopropyl, butyl or isobutyl, or a C$_6$–C$_{14}$-aryl group, such as phenyl or naphthyl or R$^8$ and R$^9$ and R$^3$ and R$^4$ and/or R$^5$ and R$^6$, together with the atoms connecting them, form an aromatic hydrocarbon ring system, in particular a six-membered ring, which may itself be substituted, M$^2$ is a carbon atom, R$^{10}$ is a C$_1$–C$_6$-alkyl group, in particular methyl, R$^{11}$ is —CH$_2$—CH$_2$—, R$^{12}$ and R$^{13}$ are identical or different and are a methyl or phenyl group, and m is 0.

Preferably, at least one of the radicals R$^3$ to R$^9$, in particular at least one of the radicals R$^4$, R$^5$ and R$^8$, is other than hydrogen, in particular if R$^{11}$ is —CH$_2$—CH$_2$—.

Examples of metallocene compounds according to the invention are:

[4-($\eta^5$-cyclopentadienyl)-4,7,7-trimethyl($\eta^5$-4,5,6,7-tetrahydroindenyl)]dichlorotitanium,

[4-($\eta^5$-cyclopentadienyl)-4,7,7-trimethyl($\eta^5$-4,5,6,7-tetrahydroindenyl)]dichlorozirconium,

[4-($\eta^5$-cyclopentadienyl)-4,7,7-trimethyl($\eta^5$-4,5,6,7-tetrahydroindenyl)]dichlorohafnium,

[4-($\eta^5$-cyclopentadienyl)-4,7,7-trimethyl($\eta^5$-4,5,6,7-tetrahydroindenyl)]dichlorotitanium,

[4-($\eta^5$-cyclopentadienyl)-4,7,7-trimethyl($\eta^5$-4,5,6,7-tetrahydroindenyl)]dichlorozirconium,

[4-($\eta^5$-cyclopentadienyl)-4,7-dimethyl-7-phenyl($\eta^5$-4,5,6,7-tetrahydroindenyl)]dichlorotitanium,
[4-($\eta^5$-cyclopentadienyl)-4,7-dimethyl-7-phenyl($\eta^5$-4,5,6,7-tetrahydroindenyl)]dichlorozirconium,
[4-($\eta^5$-cyclopentadienyl)-4,7-dimethyl-7-naphthyl($\eta^5$-4,5,6,7-tetrahydroindenyl)]dichlorotitanium,
[4-($\eta^5$-cyclopentadienyl)-4,7-dimethyl-7-naphthyl($\eta^5$-4,5,6,7-tetrahydroindenyl)]dichlorozirconium,
[4-($\eta^5$-cyclopentadienyl)-4,7-dimethyl-7-butyl($\eta^5$-4,5,6,7-tetrahydroindenyl)]dichlorotitanium,
[4-($\eta^5$-cyclopentadienyl)-4,7-dimethyl-7-butyl($\eta^5$-4,5,6,7-tetrahydroindenyl)]dichlorozirconium,
[4-($\eta^5$-3'-tert-butylcyclopentadienyl)-4,7,7,-trimethyl($\eta^5$-4,5,6,7-tetrahydroindenyl)]dichlorotitanium,
[4-($\eta^5$-3'-tert-butylcyclopentadienyl)-4,7,7,-trimethyl($\eta^5$-4,5,6,7-tetrahydroindenyl)]dichlorozirconium,
[4-($\eta^5$-3'-tert-butylcyclopentadienyl)-4,7,7,-triphenyl($\eta^5$-4,5,6,7-tetrahydroindenyl)]dichlorotitanium,
[4-($\eta^5$-3'-tert-butylcyclopentadienyl)-4,7,7,-triphenyl($\eta^5$-4,5,6,7-tetrahydroindenyl)]dichlorozirconium,
[4-($\eta^5$-3'-tert-butylcyclopentadienyl)-4,7-dimethyl-7-phenyl($\eta^5$-4,5,6,7-tetrahydroindenyl)]dichlorotitanium,
[4-($\eta^5$-3'-tert-butylcyclopentadienyl)-4,7-dimethyl-7-phenyl($\eta^5$-4,5,6,7-tetrahydroindenyl)]dichlorozirconium,
[4-($\eta^5$-3'-tert-butylcyclopentadienyl)-4,7-dimethyl-7-naphthyl($\eta^5$-4,5,6,7-tetrahydroindenyl)]dichlorotitanium,
[4-($\eta^5$-3'-tert-butylcyclopentadienyl)-4,7-dimethyl-7-naphthyl($\eta^5$-4,5,6,7-tetrahydroindenyl)]dichlorozirconium,
[4-($\eta^5$-3'-tert-butylcyclopentadienyl)-4,7-dimethyl-7-butyl($\eta^5$-4,5,6,7-tetrahydroindenyl)]dichlorotitanium,
[4-($\eta^5$-3'-tert-butylcyclopentadienyl)-4,7-dimethyl-7-butyl($\eta^5$-4,5,6,7-tetrahydroindenyl)]dichlorozirconium,
[4-($\eta^5$-indenyl)-4,7,7-trimethyl($\eta^5$-4,5,6,7-tetrahydroindenyl)]dichlorotitanium,
[4-($\eta^5$-indenyl)-4,7,7-trimethyl($\eta^5$-4,5,6,7-tetrahydroindenyl)]dichlorozirconium,
[4-($\eta^5$-indenyl)-4,7,7-triphenyl($\eta^5$-4,5,6,7-tetrahydroindenyl)]dichlorotitanium,
[4-($\eta^5$-indenyl)-4,7,7-triphenyl($\eta^5$-4,5,6,7-tetrahydroindenyl)]dichlorozirconium,
[4-($\eta^5$-indenyl)-4,7-dimethyl-7-phenyl($\eta^5$-4,5,6,7-tetrahydroindenyl)]dichlorotitanium,
[4-($\eta^5$-indenyl)-4,7-dimethyl-7-phenyl($\eta^5$-4,5,6,7-tetrahydroindenyl)]dichlorozirconium,
[4-($\eta^5$-indenyl)-4,7-dimethyl-7-naphthyl($\eta^5$-4,5,6,7-tetrahydroindenyl)]dichlorotitanium,
[4-($\eta^5$-indenyl)-4,7-dimethyl-7-naphthyl($\eta^5$-4,5,6,7-tetrahydroindenyl)]dichlorozirconium,
[4-($\eta^5$-indenyl)-4,7-dimethyl-7-butyl($\eta^5$-4,5,6,7-tetrahydroindenyl)]dichlorotitanium,
[4-($\eta^5$-indenyl)-4,7-dimethyl-7-butyl($\eta^5$-4,5,6,7-tetrahydroindenyl)]dichlorozirconium,
[4-($\eta^5$-cyclopentadienyl)-4,7,7,-trimethyl($\eta^5$-4,5,6,7-tetrahydrofluorenyl)]dichlorotitanium,
[4-($\eta^5$-cyclopentadienyl)-4,7,7,-trimethyl($\eta^5$-4,5,6,7-tetrahydrofluorenyl)]dichlorozirconium,
[4-($\eta^5$-cyclopentadienyl)-4,7,7,-triphenyl($\eta^5$-4,5,6,7-tetrahydrofluorenyl)]dichlorotitanium,
[4-($\eta^5$-cyclopentadienyl)-4,7,7,-triphenyl($\eta^5$-4,5,6,7-tetrahydrofluorenyl)]dichlorozirconium,
[4-($\eta^5$-cyclopentadienyl)-4,7,-dimethyl-7-phenyl($\eta^5$-4,5,6,7-tetrahydrofluorenyl)]dichlorotitanium,
[4-($\eta^5$-cyclopentadienyl)-4,7,-dimethyl-7-phenyl($\eta^5$-4,5,6,7-tetrahydrofluorenyl)]dichlorozirconium,
[4-($\eta^5$-cyclopentadienyl)-4,7,-dimethyl-7-naphthyl($\eta^5$-4,5,6,7-tetrahydrofluorenyl)]dichlorotitanium,
[4-($\eta^5$-cyclopentadienyl)-4,7,-dimethyl-7-naphthyl($\eta^5$-4,5,6,7-tetrahydrofluorenyl)]dichlorozirconium,
[4-($\eta^5$-cyclopentadienyl)-4,7,-dimethyl-7-butyl($\eta^5$-4,5,6,7-tetrahydrofluorenyl)]dichlorotitanium,
[4-($\eta^5$-cyclopentadienyl)-4,7,-dimethyl-7-butyl($\eta^5$-4,5,6,7-tetrahydrofluorenyl)]dichlorozirconium,
[4-($\eta^5$-3'-methylcyclopentadienyl)-4,7,7-trimethyl($\eta^5$-4,5,6,7-tetrahydroindenyl)]dichlorotitanium,
[4-($\eta^5$-3'-methylcyclopentadienyl)-4,7,7-trimethyl($\eta^5$-4,5,6,7-tetrahydroindenyl)]dichlorozirconium,
[4-($\eta^5$-3'-methylcyclopentadienyl)-4,7,7-triphenyl($\eta^5$-4,5,6,7-tetrahydroindenyl)]dichlorotitanium,
[4-($\eta^5$-3'-methylcyclopentadienyl)-4,7,7-triphenyl($\eta^5$-4,5,6,7-tetrahydroindenyl)]dichlorozirconium,
[4-($\eta^5$-3'-methylcyclopentadienyl)-4,7-dimethyl-7-phenyl($\eta^5$-4,5,6,7-tetrahydroindenyl)]dichlorotitanium,
[4-($\eta^5$-3'-methylcyclopentadienyl)-4,7-dimethyl-7-phenyl($\eta^5$-4,5,6,7-tetrahydroindenyl)]dichlorozirconium,
[4-($\eta^5$-3'-methylcyclopentadienyl)-4,7-dimethyl-7-naphthyl($\eta^5$-4,5,6,7-tetrahydroindenyl)]dichlorotitanium,
[4-($\eta^5$-3'-methylcyclopentadienyl)-4,7-dimethyl-7-naphthyl($\eta^5$-4,5,6,7-tetrahydroindenyl)]dichlorozirconium,
[4-($\eta^5$-3'-methylcyclopentadienyl)-4,7-dimethyl-7-butyl($\eta^5$-4,5,6,7-tetrahydroindenyl)]dichlorotitanium,
[4-($\eta^5$-3'-methylcyclopentadienyl)-4,7-dimethyl-7-butyl($\eta^5$-4,5,6,7-tetrahydroindenyl)]dichlorozirconium,
[4-($\eta^5$-cyclopentadienyl)-4,7,7-trimethyl-($\eta^5$-2-methyl-4,5,6,7-tetrahydroindenyl)]dichlorotitanium,
[4-($\eta^5$-cyclopentadienyl)-4,7,7-trimethyl-($\eta^5$-2-methyl-4,5,6,7-tetrahydroindenyl)]dichlorozirconium,
[4-($\eta^5$-cyclopentadienyl)-4,7,7-triphenyl-($\eta^5$-2-methyl-4,5,6,7-tetrahydroindenyl)]dichlorotitanium,
[4-($\eta^5$-cyclopentadienyl)-4,7,7-triphenyl-($\eta^5$-2-methyl-4,5,6,7-tetrahydroindenyl)]dichlorozirconium,
[4-($\eta^5$-cyclopentadienyl)-4,7-dimethyl-7-phenyl($\eta^5$-2-methyl-4,5,6,7-tetrahydroindenyl)]dichlorotitanium,
[4-($\eta^5$-cyclopentadienyl)-4,7-dimethyl-7-phenyl($\eta^5$-2-methyl-4,5,6,7-tetrahydroindenyl)]dichlorozirconium,
[4-($\eta^5$-cyclopentadienyl)-4,7-dimethyl-7-naphthyl($\eta^5$-2-methyl-4,5,6,7-tetrahydroindenyl)]dichlorotitanium,
[4-($\eta^5$-cyclopentadienyl)-4,7-dimethyl-7-naphthyl($\eta^5$-2-methyl-4,5,6,7-tetrahydroindenyl)]dichlorozirconium,
[4-($\eta^5$-cyclopentadienyl)-4,7-dimethyl-7-butyl($\eta^5$-2-methyl-4,5,6,7-tetrahydroindenyl)]dichlorotitanium,
[4-($\eta^5$-cyclopentadienyl)-4,7-dimethyl-7-butyl($\eta^5$-2-methyl-4,5,6,7-tetrahydroindenyl)]dichlorozirconium,
[4-($\eta^5$-3'-methylcyclopentadienyl)-4,7,7-trimethyl($\eta^5$-2-methyl-4,5,6,7-tetrahydroindenyl)]dichlorotitanium,
[4-($\eta^5$-3'-methylcyclopentadienyl)-4,7,7-trimethyl($\eta^5$-2-methyl-4,5,6,7-tetrahydroindenyl)]dichlorozirconium,
[4-($\eta^5$-3'-methylcyclopentadienyl)-4,7,7-triphenyl($\eta^5$-2-methyl-4,5,6,7-tetrahydroindenyl)]dichlorotitanium,
[4-($\eta^5$-3'-methylcyclopentadienyl)-4,7,7-triphenyl($\eta^5$-2-methyl-4,5,6,7-tetrahydroindenyl)]dichlorozirconium,
[4-($\eta^5$-3'-methylcyclopentadienyl)-4,7-dimethyl-7-phenyl($\eta^5$-2-methyl-4,5,6,7-tetrahydroindenyl)]dichlorotitanium,
[4-($\eta^5$-3'-methylcyclopentadienyl)-4,7-dimethyl-7-phenyl($\eta^5$-2-methyl-4,5,6,7-tetrahydroindenyl)]dichlorozirconium,
[4-($\eta^5$-3'-methylcyclopentadienyl)-4,7-dimethyl-7-naphthyl($\eta^5$-2-methyl-4,5,6,7-tetrahydroindenyl)]dichlorotitanium,
[4-($\eta^5$-3'-methylcyclopentadienyl)-4,7-dimethyl-7-naphthyl($\eta^5$-2-methyl-4,5,6,7-tetrahydroindenyl)]dichlorozirconium,
[4-($\eta^5$-3'-methylcyclopentadienyl)-4,7-dimethyl-7-butyl($\eta^5$-2-methyl-4,5,6,7-tetrahydroindenyl)]dichlorotitanium,

[4-(η⁵-3'-methylcyclopentadienyl)-4,7-dimethyl-7-butyl(η⁵-2-methyl-4,5,6,7-tetrahydroindenyl)]dichlorozirconium,
[4-(η⁵-fluorenyl)-4,7,7-trimethyl(η⁵-4,5,6,7-tetrahydroindenyl)]dichlorotitanium,
[4-(η⁵-fluorenyl)-4,7,7-trimethyl(η⁵-4,5,6,7-tetrahydroindenyl)]dichlorozirconium,
[4-(η⁵-fluorenyl)-4,7,7-triphenyl(η⁵-4,5,6,7-tetrahydroindenyl)]dichlorotitanium,
[4-(η⁵-fluorenyl)-4,7,7-triphenyl(η⁵-4,5,6,7-tetrahydroindenyl)]dichlorozirconium,
[4-(η⁵-fluorenyl)-4,7-dimethyl-7-phenyl(η⁵-4,5,6,7-tetrahydroindenyl)]dichlorotitanium,
[4-(η⁵-fluorenyl)-4,7-dimethyl-7-phenyl(η⁵-4,5,6,7-tetrahydroindenyl)]dichlorozirconium,
[4-(η⁵-fluorenyl)-4,7-dimethyl-7-naphthyl(η⁵-4,5,6,7-tetrahydroindenyl)]dichlorotitanium,
[4-(η⁵-fluorenyl)-4,7-dimethyl-7-naphthyl(η⁵-4,5,6,7-tetrahydroindenyl)]dichlorozirconium,
[4-(η⁵-fluorenyl)-4,7-dimethyl-7-butyl(η⁵-4,5,6,7-tetrahydroindenyl)]dichlorotitanium,
[4-(η⁵-fluorenyl)-4,7-dimethyl-7-butyl(η⁵-4,5,6,7-tetrahydroindenyl)]dichlorozirconium,
[4-(η⁵-cyclopentadienyl)-4,7,7-trimethyl-4,5,6,7,10,11,12,13-octahydro-5,6-benzoindenyl)dichlorozirconium,
[5-(η⁵-cyclopentadienyl)-4,7,7-trimethyl(η⁵-4,5,6,7-tetrahydroindenyl)]dichlorotitanium,
[5-(η⁵-cyclopentadienyl)-4,7,7-trimethyl(η⁵-4,5,6,7-tetrahydroindenyl)]dichlorozirconium,
[5-(η⁵-cyclopentadienyl)-4,7,7-triphenyl(η⁵-4,5,6,7-tetrahydroindenyl)]dichlorotitanium,
[5-(η⁵-cyclopentadienyl)-4,7,7-triphenyl(η⁵-4,5,6,7-tetrahydroindenyl)]dichlorozirconium,
[5-(η⁵-cyclopentadienyl)-4,7-dimethyl-7-phenyl(η⁵-4,5,6,7-tetrahydroindenyl)]dichlorotitanium,
[5-(η⁵-cyclopentadienyl)-4,7-dimethyl-7-phenyl(η⁵-4,5,6,7-tetrahydroindenyl)]dichlorozirconium,
[5-(η⁵-cyclopentadienyl)-4,7-dimethyl-7-naphthyl(η⁵-4,5,6,7-tetrahydroindenyl)]dichlorotitanium,
[5-(η⁵-cyclopentadienyl)-4,7-dimethyl-7-naphthyl(η⁵-4,5,6,7-tetrahydroindenyl)]dichlorozirconium,
[5-(η⁵-cyclopentadienyl)-4,7-dimethyl-7-butyl(η⁵-4,5,6,7-tetrahydroindenyl)]dichlorotitanium,
[5-(η⁵-cyclopentadienyl)-4,7-dimethyl-7-butyl(η⁵-4,5,6,7-tetrahydroindenyl)]dichlorozirconium,
[5-(η⁵-3'-tert-butylcyclopentadienyl)-4,7,7-trimethyl(η⁵-4,5,6,7-tetrahydroindenyl)]dichlorotitanium,
[5-(η⁵-3'-tert-butylcyclopentadienyl)-4,7,7-trimethyl(η⁵-4,5,6,7-tetrahydroindenyl)]dichlorozirconium,
[5-(η⁵-3'-tert-butylcyclopentadienyl)-4,7,7-triphenyl(η⁵-4,5,6,7-tetrahydroindenyl)]dichlorotitanium,
[5-(η⁵-3'-tert-butylcyclopentadienyl)-4,7,7-triphenyl(η⁵-4,5,6,7-tetrahydroindenyl)]dichlorozirconium,
[5-(η⁵-3'-tert-butylcyclopentadienyl)-4,7-dimethyl-7-phenyl(η⁵-4,5,6,7-tetrahydroindenyl)]dichlorotitanium,
[5-(η⁵-3'-tert-butylcyclopentadienyl)-4,7-dimethyl-7-phenyl(η⁵-4,5,6,7-tetrahydroindenyl)]dichlorozirconium,
[5-(η⁵-3'-tert-butylcyclopentadienyl)-4,7-dimethyl-7-naphthyl(η⁵-4,5,6,7-tetrahydroindenyl)]dichlorotitanium,
[5-(η⁵-3'-tert-butylcyclopentadienyl)-4,7-dimethyl-7-naphthyl(η⁵-4,5,6,7-tetrahydroindenyl)]dichlorozirconium,
[5-(η⁵-3'-tert-butylcyclopentadienyl)-4,7-dimethyl-7-butyl(η⁵-4,5,6,7-tetrahydroindenyl)]dichlorotitanium,
[5-(η⁵-3'-tert-butylcyclopentadienyl)-4,7-dimethyl-7-butyl(η⁵-4,5,6,7-tetrahydroindenyl)]dichlorozirconium,
[5-(η⁵-indenyl)-4,7,7-trimethyl-(η⁵-4,5,6,7-tetrahydroindenyl)]dichlorotitanium,
[5-(η⁵-indenyl)-4,7,7-trimethyl-(η⁵-4,5,6,7-tetrahydroindenyl)]dichlorozirconium,
[5-(η⁵-indenyl)-4,7,7-triphenyl-(η⁵-4,5,6,7-tetrahydroindenyl)]dichlorotitanium,
[5-(η⁵-indenyl)-4,7,7-triphenyl-(η⁵-4,5,6,7-tetrahydroindenyl)]dichlorozirconium,
[5-(η⁵-indenyl)-4,7-dimethyl-7-phenyl(η⁵-4,5,6,7-tetrahydroindenyl)]dichlorotitanium,
[5-(η⁵-indenyl)-4,7-dimethyl-7-phenyl(η⁵-4,5,6,7-tetrahydroindenyl)]dichlorozirconium,
[5-(η⁵-indenyl)-4,7-dimethyl-7-naphthyl(η⁵-4,5,6,7-tetrahydroindenyl)]dichlorotitanium,
[5-(η⁵-indenyl)-4,7-dimethyl-7-naphthyl(η⁵-4,5,6,7-tetrahydroindenyl)]dichlorozirconium,
[5-(η⁵-indenyl)-4,7-dimethyl-7-butyl(η⁵-4,5,6,7-tetrahydroindenyl)]dichlorotitanium,
[5-(η⁵-indenyl)-4,7-dimethyl-7-butyl(η⁵-4,5,6,7-tetrahydroindenyl)]dichlorozirconium,
[5-(η⁵-cyclopentadienyl)-4,7,7-trimethyl(η⁵-4,5,6,7-tetrahydroindenyl)]dichlorotitanium,
[5-(η⁵-cyclopentadienyl)-4,7,7-trimethyl(η⁵-4,5,6,7-tetrahydroindenyl)]dichlorozirconium,
[5-(η⁵-cyclopentadienyl)-4,7,7-triphenyl(η⁵-4,5,6,7-tetrahydroindenyl)]dichlorotitanium,
[5-(η⁵-cyclopentadienyl)-4,7,7-triphenyl(η⁵-4,5,6,7-tetrahydroindenyl)]dichlorozirconium,
[5-(η⁵-cyclopentadienyl)-4,7-dimethyl-7-phenyl(η⁵-4,5,6,7-tetrahydroindenyl)]dichlorotitanium,
[5-(η⁵-cyclopentadienyl)-4,7-dimethyl-7-phenyl(η⁵-4,5,6,7-tetrahydroindenyl)]dichlorozirconium,
[5-(η⁵-cyclopentadienyl)-4,7-dimethyl-7-naphthyl(η⁵-4,5,6,7-tetrahydroindenyl)]dichlorotitanium,
[5-(η⁵-cyclopentadienyl)-4,7-dimethyl-7-naphthyl(η⁵-4,5,6,7-tetrahydroindenyl)]dichlorozirconium,
[5-(η⁵-cyclopentadienyl)-4,7-dimethyl-7-butyl(η⁵-4,5,6,7-tetrahydroindenyl)]dichlorotitanium,
[5-(η⁵-cyclopentadienyl)-4,7-dimethyl-7-butyl(η⁵-4,5,6,7-tetrahydroindenyl)]dichlorozirconium,
[5-(η⁵-fluorenyl)-4,7,7-trimethyl(η⁵-4,5,6,7-tetrahydroindenyl)]dichlorotitanium,
[5-(η⁵-fluorenyl)-4,7,7-trimethyl(η⁵-4,5,6,7-tetrahydroindenyl)]dichlorozirconium,
[5-(η⁵-fluorenyl)-4,7,7-triphenyl(η⁵-4,5,6,7-tetrahydroindenyl)]dichlorotitanium,
[5-(η⁵-fluorenyl)-4,7,7-triphenyl(η⁵-4,5,6,7-tetrahydroindenyl)]dichlorozirconium,
[5-(η⁵-fluorenyl)-4,7-dimethyl-7-phenyl(η⁵-4,5,6,7-tetrahydroindenyl)]dichlorotitanium,
[5-(η⁵-fluorenyl)-4,7-dimethyl-7-phenyl(η⁵-4,5,6,7-tetrahydroindenyl)]dichlorozirconium,
[4-(η⁵-3'-isopropylcyclopentadienyl)-4,7,7-trimethyl-η⁵-4,5,6,7-tetrahydroindenyl]dichlorozirconium
[4-(η⁵-4'-isopropylcyclopentadienyl)-4,7,7-trimethyl-η⁵-4,5,6,7-tetrahydroindenyl]dichlorozirconium
[4-(η⁵-3'-isopropylcyclopentadienyl)-2-isopropyl-4,7,7-trimethyl-η⁵-4,5,6,7-tetrahydroindenyl]dichlorozirconium
[4-(η⁵-4'-isopropylcyclopentadienyl)-2-isopropyl-4,7,7-trimethyl-η⁵-4,5,6,7-tetrahydroindenyl]dichlorozirconium
[4-(η⁵-3'-isopropylcyclopentadienyl)-4,7-dimethyl-7-phenyl-η⁵-4,5,6,7-tetrahydroindenyl]dichlorozirconium
[4-(η⁵-4'-isopropyl-cyclopentadienyl)-4,7-dimethyl-7-phenyl-η⁵-4,5,6,7-tetrahydroindenyl]dichlorozirconium
[4-(η⁵-3'-isopropylcyclopentadienyl)-2-isopropyl-4,7-dimethyl-7-phenyl-η⁵-4,5,6,7-tetrahydroindenyl]dichlorozirconium

[4-($\eta^5$-4'-isopropylcyclopentadienyl)-2-isopropyl-4,7-dimethyl-7-phenyl-$\eta^5$-4,5,6,7-tetrahydroindenyl]dichlorozirconium

[4-($\eta^5$-3'-trimethylsilylcyclopentadienyl)-4,7,7-trimethyl-$\eta^5$-4,5,6,7-tetrahydroindenyl]dichlorozirconium

[4-($\eta^5$-4'-trimethylsilylcyclopentadienyl)-4,7,7-trimethyl-$\eta^5$-4,5,6,7-tetrahydroindenyl]dichlorozirconium

[4-($\eta^5$-3'-trimethylsilylcyclopentadienyl)-2-trimethylsilyl-4,7,7-trimethyl-$\eta^5$-4,5,6,7-tetrahydroindenyl]dichlorozirconium

[4-($\eta^5$-4'-trimethylsilylcyclopentadienyl)-2-trimethylsilyl-4,7,7-trimethyl-$\eta^5$-4,5,6,7-tetrahydroindenyl]dichlorozirconium

[4-($\eta^5$-3'-(tert-butyldimethylsilyl)cyclopentadienyl)-4,7,7-trimethyl-$\eta^5$-4,5,6,7-tetrahydroindenyl]dichlorozirconium

[4-($\eta^5$-4'-(tert-butyldimethylsilyl)cyclopentadienyl)-4,7,7-trimethyl-$\eta^5$-4,5,6,7-tetrahydroindenyl]dichlorozirconium

[4-($\eta^5$-3'-(tert-butyldimethylsilyl)cyclopentadienyl)-2-(tert-butyldimethylsilyl)-4,7,7-trimethyl-$\eta^5$-4,5,6,7-tetrahydroindenyl]dichlorozirconium

[4-($\eta^5$-4'-(tert-butyldimethylsilyl)cyclopentadienyl)-2-(tert-butyldimethylsilyl)-4,7,7-trimethyl-$\eta^5$-4,5,6,7-tetrahydroindenyl]dichlorozirconium

[4-($\eta^5$-3'-trimethylsilylcyclopentadienyl)-4,7-dimethyl-7-phenyl-$\eta^5$-4,5,6,7-tetrahydroindenyl]dichlorozirconium

[4-($\eta^5$-4'-trimethylsilylcyclopentadienyl)-4,7-dimethyl-7-phenyl-$\eta^5$-4,5,6,7-tetrahydroindenyl]dichlorozirconium

[4-($\eta^5$-3'-trimethylsilylcyclopentadienyl)-2-trimethylsilyl-4,7-dimethyl-7-phenyl-$\eta^5$-4,5,6,7-tetrahydroindenyl]dichlorozirconium

[4-($\eta^5$-4'-trimethylsilylcyclopentadienyl)-2-trimethylsilyl-4,7-dimethyl-7-phenyl-$\eta^5$-4,5,6,7-tetrahydroindenyl]dichlorozirconium

[4-($\eta^5$-3'-phenylcyclopentadienyl)-4,7,7-trimethyl-$\eta^5$-4,5,6,7-tetrahydroindenyl]dichlorozirconium

[4-($\eta^5$-4'-phenylcyclopentadienyl)-4,7,7-trimethyl-$\eta^5$-4,5,6,7-tetrahydroindenyl]dichlorozirconium

[4-($\eta^5$-3'-phenylcyclopentadienyl)-2-phenyl-4,7,7-trimethyl-$\eta^5$-4,5,6,7-tetrahydroindenyl]dichlorozirconium

[4-($\eta^5$-4'-phenylcyclopentadienyl)-2-phenyl-4,7,7-trimethyl-$\eta^5$-4,5,6,7-tetrahydroindenyl]dichlorozirconium

[4-($\eta^5$-3'-phenylcyclopentadienyl)-4,7-dimethyl-7-phenyl-$\eta^5$-4,5,6,7-tetrahydroindenyl]dichlorozirconium

[4-($\eta^5$-4'-phenylcyclopentadienyl)-4,7-dimethyl-7-phenyl-$\eta^5$-4,5,6,7-tetrahydroindenyl]dichlorozirconium

[4-($\eta^5$-3'-phenylcyclopentadienyl)-2-phenyl-4,7-dimethyl-7-phenyl-$\eta^5$-4,5,6,7-tetrahydroindenyl]dichlorozirconium

[4-($\eta^5$-4'-phenylcyclopentadienyl)-2-phenyl-4,7-dimethyl-7-phenyl-$\eta^5$-4,5,6,7-tetrahydroindenyl]dichlorozirconium

[4-($\eta^5$-4'-methylcyclopentadienyl)-4,7,7-trimethyl-$\eta^5$-4,5,6,7-tetrahydroindenyl]dichlorozirconium

[4-($\eta^5$-4'-methylcyclopentadienyl)-2-methyl-4,7,7-trimethyl-$\eta^5$-4,5,6,7-tetrahydroindenyl]dichlorozirconium

[4-($\eta^5$-4'-methylcyclopentadienyl)-2-methyl-4,7-dimethyl-7-phenyl-$\eta^5$-4,5,6,7-tetrahydroindenyl]dichlorozirconium

[4-($\eta^5$-4'-tert-butylcyclopentadienyl)-2-tert-butyl-4,7,7-trimethyl-$\eta^5$-4,5,6,7-tetrahydroindenyl]dichlorozirconium

[4-($\eta^5$-3'-tert-butylcyclopentadienyl)-2-tert-butyl-4,7,7-trimethyl-$\eta^5$-4,5,6,7-tetrahydroindenyl]dichlorozirconium

[4-($\eta^5$-4'-tert-butylcyclopentadienyl)-4,7,7-trimethyl-$\eta^5$-4,5,6,7-tetrahydroindenyl]dichlorozirconium

[4-($\eta^5$-3'-benzylcyclopentadienyl)-4,7,7-trimethyl-$\eta^5$-4,5,6,7-tetrahydroindenyl]dichlorozirconium

[4-($\eta^5$-4'-benzylcyclopentadienyl)-4,7,7-trimethyl-$\eta^5$-4,5,6,7-tetrahydroindenyl]dichlorozirconium

[4-($\eta^5$-3'-benzylcyclopentadienyl)-2-benzyl-4,7,7-trimethyl-$\eta^5$-4,5,6,7-tetrahydroindenyl]dichlorozirconium

[4-($\eta^5$-4'-benzylcyclopentadienyl)-2-benzyl-4,7,7-trimethyl-$\eta^5$-4,5,6,7-tetrahydroindenyl]dichlorozirconium

[4-($\eta^5$-cyclopentadienyl)-4-butyl-7,7-dimethyl-$\eta^5$-4,5,6,7-tetrahydroindenyl]dichlorozirconium

[4-($\eta^5$-cyclopentadienyl)-4-butyl-7-methyl-7-butyl-$\eta^5$-4,5,6,7-tetrahydroindenyl]dichlorozirconium

[4-($\eta^5$-cyclopentadienyl)-4-methyl-7,7-dibutyl-$\eta^5$-4,5,6,7-tetrahydroindenyl]dichlorozirconium

[4-($\eta^5$-cyclopentadienyl)-4-methyl-7-butyl-7-phenyl-$\eta^5$-4,5,6,7-tetrahydroindenyl]dichlorozirconium

[4-($\eta^5$-cyclopentadienyl)-4-butyl-7-methyl-7-phenyl-$\eta^5$-4,5,6,7-tetrahydroindenyl]dichlorozirconium

[4-($\eta^5$-3'-isopropylcyclopentadienyl)-2-isopropyl-4-butyl-7,7-dimethyl-$\eta^5$-4,5,6,7-tetrahydroindenyl]dichlorozirconium

[4-($\eta^5$-4'-isopropylcyclopentadienyl)-2-isopropyl-4-butyl-7,7-dimethyl-$\eta^5$-4,5,6,7-tetrahydroindenyl]dichlorozirconium

[4-($\eta^5$-3'-isopropylcyclopentadienyl)-2-isopropyl-4-butyl-7-butyl-7-methyl-$\eta^5$-4,5,6,7-tetrahydroindenyl]dichlorozirconium

[4-($\eta^5$-4'-isopropylcyclopentadienyl)-2-isopropyl-4-butyl-7-methyl-7-phenyl-$\eta^5$-4,5,6,7-tetrahydroindenyl]dichlorozirconium

[4-($\eta^5$-3'-isopropylcyclopentadienyl)-4-butyl-7-butyl-7-methyl-$\eta^5$-4,5,6,7-tetrahydroindenyl]dichlorozirconium

[4-($\eta^5$-4'-isopropylcyclopentadienyl)-4-butyl-7-7-methyl-7-phenyl-$\eta^5$-4,5,6,7-tetrahydroindenyl]dichlorozirconium

[4-($\eta^5$-cyclopentadienyl)-4,7-dimethyl-7-(2-propan-1-yl)-($\eta^5$-4,5,6,7-tetrahydroindenyl]dichlorozirconium

[4-($\eta^5$-3'-isopropylcyclopentadienyl)-4,7-dimethyl-7-(2-propan-1-yl)-($\eta^5$-4,5,6,7-tetrahydroindenyl]dichlorozirconium

[4-($\eta^5$-cyclopentadienyl)-4,7-dimethyl-7-(3-(9-borabicyclo{3,3,1}nonyl-$\beta$)propyl)-($\eta^5$-4,5,6,7-tetrahydroindenyl]dichlorozirconium

[4-($\eta^5$-3'-isopropylcyclopentadienyl)-4,7-dimethyl-7-(3-(9-borabicyclo{3,3,1}nonyl-$\beta$)propyl)-($\eta^5$-4,5,6,7-tetrahydroindenyl]dichlorozirconium

[4-($\eta^5$-4'-isopropylcyclopentadienyl)-4,7-dimethyl-7-(3-(9-borabicyclo{3,3,1}nonyl-$\beta$)propyl)-($\eta^5$-4,5,6,7-tetrahydroindenyl]dichlorozirconium

[4-($\eta^5$-3'-tert-butylcyclopentadienyl)-4,7-dimethyl-7-(3-(9-borabicyclo{3,3,1}nonyl-$\beta$)propyl)-($\eta^5$-4,5,6,7-tetrahydroindenyl]dichlorozirconium

[4-($\eta^5$-4'-tert-butylcyclopentadienyl)-4,7-dimethyl-7-(3-(9-borabicyclo{3,3,1}nonyl-$\beta$)propyl)-($\eta^5$-4,5,6,7-tetrahydroindenyl]dichlorozirconium

[4-($\eta^5$-3'-methylcyclopentadienyl)-4,7-dimethyl-7-(3-(9-borabicyclo{3,3,1}nonyl-$\beta$)propyl)-($\eta^5$-4,5,6,7-tetrahydroindenyl]dichlorozirconium

[4-($\eta^5$-3'-isopropylcyclopentadienyl)-2-isopropyl-4,7-dimethyl-7-(3-(9-borabicyclo{3,3,1}nonyl-$\beta$)propyl)-($\eta^5$-4,5,6,7-tetrahydroindenyl]dichlorozirconium

[4-($h^5$-4'-isopropylcyclopentadienyl)-2-isopropyl-4,7-dimethyl-7-(3-(9-borabicyclo{3,3,1}nonyl-$\beta$)propyl)-($\eta^5$-4,5,6,7-tetrahydroindenyl]dichlorozirconium

[4-($\eta^5$-3'-ethylcyclopentadienyl)-4,7,7-trimethyl-$\eta^5$-4,5,6,7-tetrahydroindenyl]dichlorozirconium

[4-($\eta^5$-4'-ethylcyclopentadienyl)-4,7,7-trimethyl-$\eta^5$-4,5,6,7-tetrahydroindenyl]dichlorozirconium

[4-($\eta^5$-3'-ethylcyclopentadienyl)-2-ethyl-4,7,7-trimethyl-$\eta^5$-4,5,6,7-tetrahydroindenyl]dichlorozirconium

[4-($\eta^5$-3'-ethylcyclopentadienyl)-2-ethyl-4,7,7-trimethyl-$\eta^5$-4,5,6,7-tetrahydroindenyl]dichlorozirconium

[4-($\eta^5$-3'-isopropylcyclopentadienyl)-2-phenyl-4,7,7-trimethyl-$\eta^5$-4,5,6,7-tetrahydroindenyl]dichlorozirconium

[4-($\eta^5$-4'-isopropylcyclopentadienyl)-2-phenyl-4,7,7-trimethyl-$\eta^5$-4,5,6,7-tetrahydroindenyl]dichlorozirconium

[4-($\eta^5$-3'-isopropylcyclopentadienyl)-2-methyl-4,7,7-trimethyl-$\eta^5$-4,5,6,7-tetrahydroindenyl]dichlorozirconium

[4-($\eta^5$-4'-isopropylcyclopentadienyl)-2-methyl-4,7,7-trimethyl-$\eta^5$-4,5,6,7-tetrahydroindenyl]dichlorozirconium

[4-($\eta^5$-3'-isopropylcyclopentadienyl)-2-phenyl-4,7,7-trimethyl-$\eta^5$-4,5,6,7-tetrahydroindenyl]dichlorozirconium

[4-($\eta^5$-4'-isopropylcyclopentadienyl)-2-phenyl-4,7,7-trimethyl-$\eta^5$-4,5,6,7-tetrahydroindenyl]dichlorozirconium

[4-($\eta^5$-2-indenyl)-4,7,7-trimethyl-$\eta^5$-4,5,6,7-tetrahydroindenyl]dichlorozirconium

[4-($\eta^5$-2-(4,5,6,7-tetrahydro)indenyl)-4,7,7-trimethyl-$\eta^5$-4,5,6,7-tetrahydroindenyl]dichlorozirconium

[4-($\eta^5$-2-indenyl)-2-methyl-4,7,7-trimethyl-$\eta^5$-4,5,6,7-tetrahydroindenyl]dichlorozirconium

[4-($\eta^5$-2-(4,5,6,7-tetrahydro)indenyl)-2-isopropyl-4,7,7-trimethyl-$\eta^5$-4,5,6,7-tetrahydroindenyl]dichlorozirconium

[4-($\eta^5$-2-indenyl)-2-phenyl-4,7,7-trimethyl-$\eta^5$-4,5,6,7-tetrahydroindenyl]dichlorozirconium

[4-($\eta^5$-2-(4,5,6,7-tetrahydro)indenyl)-2-butyl-4,7,7-trimethyl-$\eta^5$-4,5,6,7-tetrahydroindenyl]dichlorozirconium

[4-($\eta^5$-2-indenyl)-2-trimethylsilyl-4,7,7-trimethyl-$\eta^5$-4,5,6,7-tetrahydroindenyl]dichlorozirconium

[4-($\eta^5$-2-(4,5,6,7-tetrahydro)indenyl)-2-trimethylsilyl-4,7,7-trimethyl-$\eta^5$-4,5,6,7-tetrahydroindenyl]dichlorozirconium

[4-($\eta^5$-2-indenyl)-2-isopropyl-4,7,7-trimethyl-$\eta^5$-4,5,6,7-tetrahydroindenyl]dichlorozirconium

[4-($\eta^5$-2-(4,5,6,7-tetrahydro)indenyl)-2-methyl-4,7,7-trimethyl-$\eta^5$-4,5,6,7-tetrahydroindenyl]dichlorozirconium

[4-($\eta^5$-2-indenyl)-2-butyl-4,7,7-trimethyl-$\eta^5$-4,5,6,7-tetrahydroindenyl]dichlorozirconium

[4-($\eta^5$-3'-isopropylcyclopentadienyl)-2-methyl-4,7,7-trimethyl-$\eta^5$-4,5,6,7-tetrahydroindenyl]dichlorozirconium

[4-($\eta^5$-4'-isopropylcyclopentadienyl)-2-methyl-4,7,7-trimethyl-$\eta^5$-4,5,6,7-tetrahydroindenyl]dichlorozirconium

[4-($\eta^5$-3'-isopropylcyclopentadienyl)-4,7,7-trimethyl-$\eta^5$-4,5,6,7-tetrahydroindenyl]dichlorozirconium

[4-($\eta^5$-4'-isopropylcyclopentadienyl)-4,7,7-trimethyl-$\eta^5$-4,5,6,7-tetrahydroindenyl]dichlorozirconium

[4-($\eta^5$-3'-isopropylcyclopentadienyl)-2-isopropyl-4,7,7-trimethyl-$\eta^5$-4,5,6,7-tetrahydroindenyl]dichlorozirconium

[4-($\eta^5$-3'-isopropylcyclopentadienyl)-4,7,7-trimethyl-$\eta^5$-4,5,6,7-tetrahydrofluorenyl]dichlorozirconium

[4-($\eta^5$-4'-isopropylcyclopentadienyl)-4,7,7-trimethyl-$\eta^5$-4,5,6,7-tetrahydrofluorenyl]dichlorozirconium

[4-($\eta^5$-3'-isopropylcyclopentadienyl)-2-isopropyl-4,7,7-trimethyl-$\eta^5$-4,5,6,7-tetrahydrofluorenyl]dichlorozirconium

[4-($\eta^5$-4'-isopropylcyclopentadienyl)-2-isopropyl-4,7,7-trimethyl-$\eta^5$-4,5,6,7-tetrahydrofluorenyl]dichlorozirconium

[4-($\eta^5$-3'-butylcyclopentadienyl)-4,7,7-trimethyl-$\eta^5$-4,5,6,7-tetrahydroindenyl]dichlorozirconium

[4-($\eta^5$-4'-butylcyclopentadienyl)-4,7,7-trimethyl-$\eta^5$-4,5,6,7-tetrahydroindenyl]dichlorozirconium

[4-($\eta^5$-3'-butylcyclopentadienyl)-2-isopropyl-4,7,7-trimethyl-$\eta^5$-4,5,6,7-tetrahydroindenyl]dichlorozirconium

[4-($\eta^5$-4'-butylcyclopentadienyl)-2-isopropyl-4,7,7-trimethyl-$\eta^5$-4,5,6,7-tetrahydroindenyl]dichlorozirconium

[4-($\eta^5$-3'-butylcyclopentadienyl-2-butyl-4,7,7-trimethyl-$\eta^5$-4,5,6,7-tetrahydroindenyl]dichlorozirconium

[4-($\eta^5$-4'-butylcyclopentadienyl)-2-butyl-4,7,7-trimethyl-$\eta^5$-4,5,6,7-tetrahydroindenyl]dichlorozirconium

[4-($\eta^5$-3',4'-dimethylcyclopentadienyl)-4,7,7-trimethyl-$\eta^5$-4,5,6,7-tetrahydroindenyl]dichlorozirconium

[4-($\eta^5$-3',4'-diisopropylcyclopentadienyl)-4,7,7-trimethyl-$\eta^5$-4,5,6,7-tetrahydroindenyl]dichlorozirconium

[4-($\eta^5$-3',4'-diphenylcyclopentadienyl)-2-isopropyl-4,7,7-trimethyl-$\eta^5$-4,5,6,7-tetrahydroindenyl]dichlorozirconium

[4-($\eta^5$-3',4'-diethylcyclopentadienyl)-2-isopropyl-4,7,7-trimethyl-$\eta^5$-4,5,6,7-tetrahydroindenyl]dichlorozirconium

[4-($\eta^5$-3',4'-dibutylcyclopentadienyl)-2-isopropyl-4,7,7-trimethyl-$\eta^5$-4,5,6,7-tetrahydroindenyl]dichlorozirconium

[4-($\eta^5$-3'-methyl-4'-phenylcyclopentadienyl)-4,7,7-trimethyl-$\eta^5$-4,5,6,7-tetrahydroindenyl]dichlorozirconium

[4-($\eta^5$-3'-ethyl-4'-phenylcyclopentadienyl)-4,7,7-trimethyl-$\eta^5$-4,5,6,7-tetrahydroindenyl]dichlorozirconium

[4-($\eta^5$-3'-isopropyl-4'-phenylcyclopentadienyl)-4,7,7-trimethyl-$\eta^5$-4,5,6,7-tetrahydroindenyl]dichlorozirconium

[4-($\eta^5$-3'-methyl-4'-isopropylcyclopentadienyl)-4,7,7-trimethyl-$\eta^5$-4,5,6,7-tetrahydroindenyl]dichlorozirconium

[4-($\eta^5$-3'-methyl-4'-naphthylcyclopentadienyl)-4,7,7-trimethyl-$\eta^5$-4,5,6,7-tetrahydroindenyl]dichlorozirconium

[4-($\eta^5$-3'-methyl-4'-butylcyclopentadienyl)-4,7,7-trimethyl-$\eta^5$-4,5,6,7-tetrahydroindenyl]dichlorozirconium The nomenclature of the abovementioned novel compounds is illustrated with reference to the compound [4-($\eta^5$-4'-methylcyclopentadienyl)-4,7,7-trimethyl ($\eta^5$-4,5,6,7-tetrahydroindenyl]dichlorozirconium. The ring system bridging the two cyclopentadienyl ligands of this compound contains six ring carbon atoms (C4, C5, C6, C7, C8 and C9) and three methyl substituents. One cyclopentadienyl group is simply fused to the ring system, and a second is a substituent on the ring system.

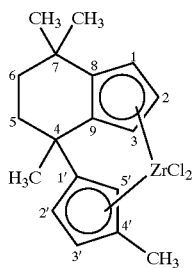

The compounds mentioned below are named in accordance with IUPAC nomenclature.

[$\eta^5$-9-($\eta^5$-cyclopentadienyl)tricyclo[6.1.1.0$^{2,6}$]deca-2,5-dienyl]dichlorotitanium,
[$\eta^5$-9-($\eta^5$-cyclopentadienyl)tricyclo[6.1.1.0$^{2,6}$]deca-2,5-dienyl]dichlorozirconium,
[$\eta^5$-7-methyl-9-($\eta^5$-cyclopentadienyl)tricyclo[6.1.1.0$^{2,6}$]deca-2,5-dienyl]dichlorotitanium,
[$\eta^5$-7-methyl-9-($\eta^5$-cyclopentadienyl)tricyclo[6.1.1.0$^{2,6}$]deca-2,5-dienyl]dichlorozirconium,
[$\eta^5$-9-methyl-9-($\eta^5$-cyclopentadienyl)tricyclo[6.1.1.0$^{2,6}$]deca-2,5-dienyl]dichlorotitanium,
[$\eta^5$-9-methyl-9-($\eta^5$-cyclopentadienyl)tricyclo[6.1.1.0$^{2,6}$]deca-2,5-dienyl]dichlorozirconium,
[$\eta^5$-10-($\eta^5$-cyclopentadienyl)tricyclo[5.2.1.0$^{2,6}$]deca-2,5-dienyl]dichlorotitanium,
[$\eta^5$-10-($\eta^5$-cyclopentadienyl)tricyclo[5.2.1.0$^{2,6}$]deca-2,5-dienyl]dichlorozirconium,
[$\eta^5$-10-methyl-10-($\eta^5$-cyclopentadienyl)tricyclo[5.2.1.0$^{2,6}$]deca-2,5-dienyl]dichlorotitanium,
[$\eta^5$-10-methyl-10-($\eta^5$-cyclopentadienyl)tricyclo[5.2.1.0$^{2,6}$]deca-2,5-dienyl]dichlorozirconium,
[$\eta^5$-9-($\eta^5$-cyclopentadienyl)tricyclo[5.2.2.0$^{2,6}$]undeca-2,5-dienyl]dichlorotitanium,
[$\eta^5$-9-($\eta^5$-cyclopentadienyl)tricyclo[5.2.2.0$^{2,6}$]undeca-2,5-dienyl]dichlorozirconium,
[$\eta^5$-9-methyl-9-($\eta^5$-cyclopentadienyl)tricyclo[5.2.2.0$^{2,6}$]undeca-2,5-dienyl]dichlorotitanium,
[$\eta^5$-9-methyl-9-($\eta^5$-cyclopentadienyl)tricyclo[5.2.2.0$^{2,6}$]undeca-2,5-dienyl]dichlorozirconium,
[$\eta^5$-10-($\eta^5$-3'-methylcyclopentadienyl)tricyclo[5.2.1.0$^{2,6}$]deca-2,5-dienyl]dichlorotitanium,
[$\eta^5$-10-($\eta^5$-3'-methylcyclopentadienyl)tricyclo[5.2.1.0$^{2,6}$]deca-2,5-dienyl]dichlorozirconium,
[$\eta^5$-10-methyl-10-($\eta^5$-3'-methylcyclopentadienyl)tricyclo[5.2.1.0$^{2,6}$]deca-2,5-dienyl]dichlorotitanium,
[$\eta^5$-10-methyl-10-($\eta^5$-3'-methylcyclopentadienyl)tricyclo[5.2.1.0$^{2,6}$]deca-2,5-dienyl]dichlorozirconium,
[$\eta^5$-4-methyl-10-($\eta^5$-3'-methylcyclopentadienyl)tricyclo[5.2.1.0$^{2,6}$]deca-2,5-dienyl]dichlorotitanium,
[$\eta^5$-4-methyl-10-($\eta^5$-3'-methylcyclopentadienyl)tricyclo[5.2.1.0$^{2,6}$]deca-2,5-dienyl]dichlorozirconium,
[$\eta^5$-4,10-dimethyl-10-($\eta^5$-3'-methylcyclopentadienyl)tricyclo[5.2.1.0$^{2,6}$]deca-2,5-dienyl]dichlorotitanium,
[$\eta^5$-4,10-dimethyl-10-($\eta^5$-3'-methylcyclopentadienyl)tricyclo[5.2.1.0$^{2,6}$]deca-2,5-dienyl]dichlorozirconium,
[$\eta^5$-5-methyl-10-($\eta^5$-3'-methylcyclopentadienyl)tricyclo[5.2.1.0$^{2,6}$]deca-2,5-dienyl]dichlorotitanium,
[$\eta^5$-5-methyl-10-($\eta^5$-3'-methylcyclopentadienyl)tricyclo[5.2.1.0$^{2,6}$]deca-2,5-dienyl]dichlorozirconium,
[$\eta^5$-5,10-dimethyl-10-($\eta^5$-3'-methylcyclopentadienyl)tricyclo[5.2.1.0$^{2,6}$]deca-2,5-dienyl]dichlorotitanium, and
[$\eta^5$-5,10-dimethyl-10-($\eta^5$-3'-methylcyclopentadienyl)tricyclo[5.2.1.0$^{2,6}$]deca-2,5-dienyl]dichlorozirconium.

The preparation of the metallocenes according to the invention is intended to be illustrated by the reaction scheme below with reference to metallocenes of the formula VI in which $M^4$ is a metal from main group Ia, IIa or IIIa.

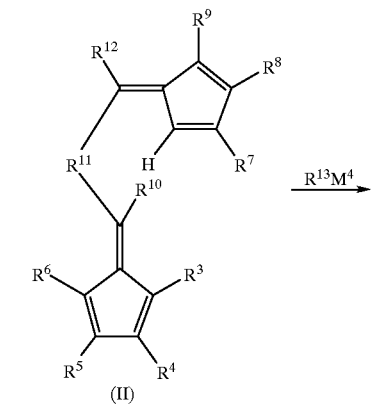

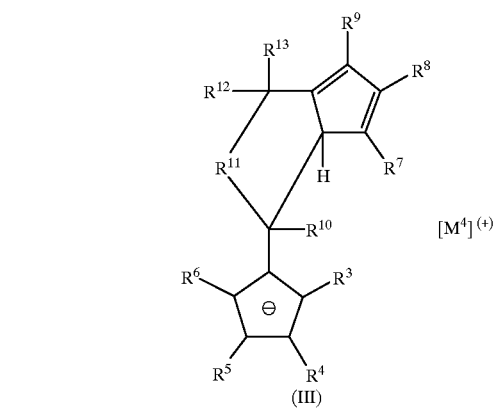

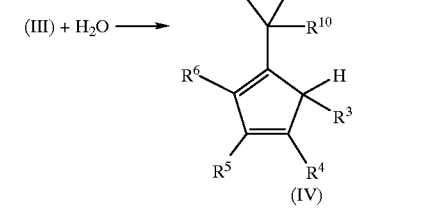

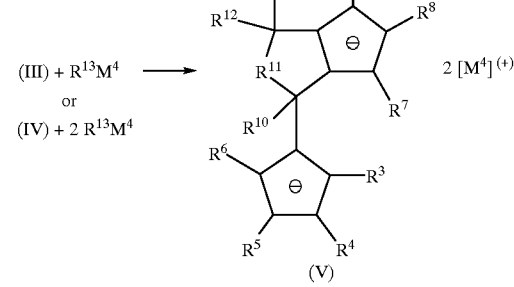

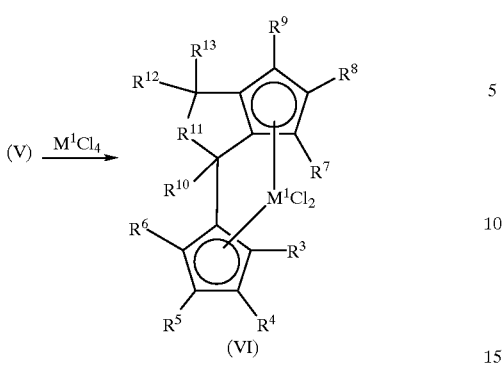

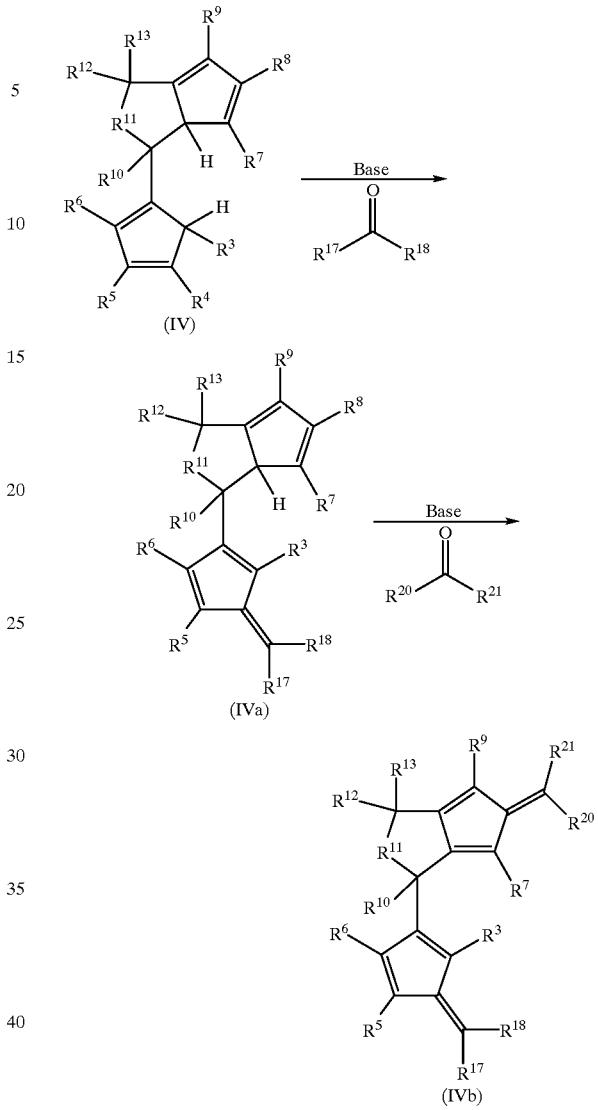

The difulvenes of the formula II are prepared from diketones (Chem. Ber. 114, 1226 (1981); ibid 109, 3426 (1976); ibid 107, 2453 (1974)) or ketoaldehydes by methods known from the literature (J. Org. Chem. 57 (1992) 2504; ibid, 49 (1984) 1849; Chimia, 46 (1992) 377).

The conversion of the difulvene II into the ligand system of the formula III is carried out by reaction with an organometallic compound (such as, for example, methyl-lithium, butyllithium or phenyllithium) or Grignard reagents. The salts of the formula III can be converted directly into the corresponding dianion compounds of the formula V by deprotonation, for example using butyllithium. Hydrolysis of compound III results in the formation of the biscyclopentadienyl compound IV, which is produced as a constitutional isomer mixture and can be purified by chromatography. Double deprotonation of IV using, for example, butyllithium gives the dianion compound of the formula V.

Conversion into the bridged metallocenes of the formula VI and isolation of the desired complexes is known in principle. To this end, the dianion of the formula V is reacted with the corresponding metal halide, such as, for example, zirconium tetrachloride, in an inert solvent. The metallocenes of the formula VI can also be synthesized directly from the difulvenes of the formula II without isolation of the intermediates.

Suitable solvents are aliphatic or aromatic solvents, such as, for example, hexane or toluene, ethereal solvents, such as, for example, tetrahydrofuran or diethyl ether, or halogenated hydrocarbons, such as, for example, methylene chloride, or halogenated aromatic hydrocarbons, such as, for example, o-dichlorobenzene.

The biscyclopentadienyl compounds of the formula IV in which at least one of the radicals $R^3$ to $R^6$ and at least one of the radicals $R^7$ to $R^9$ is hydrogen and at least one of the radicals $R^3$ to $R^9$ is not hydrogen can be converted into the fulvenes of the formula IVa or IVb by methods known from the literature. This is intended to be illustrated by the reaction scheme below, where $R^{17}$, $R^{18}$, $R^{20}$ and $R^{21}$ are identical or different and are as defined for $R^{10}$.

Reaction of the fulvene IVa with organometallic compounds of the formula $R^{19}M^5$ (where $R^{17}$, $R^{18}$, $R^{19}$, $R^{20}$ and $R^{21}$ are identical or different and are defined as for $R^{10}$; $M^5$ is as defined for $M^4$) results in the formation of the monoanion compound IIIa. Use of two equivalents of $R^{19}M^5$ results directly in the formation of the dianion compound Va.

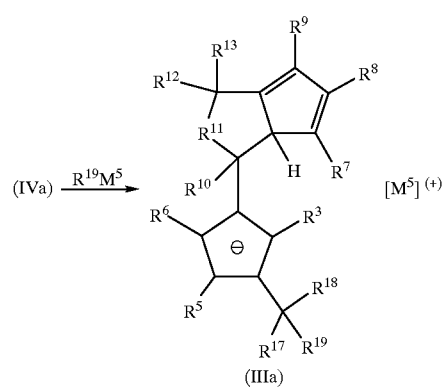

-continued

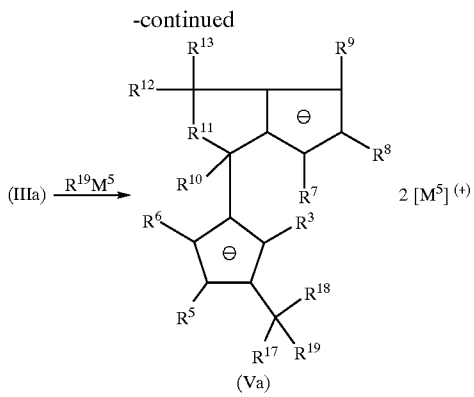

(IIIa) $\xrightarrow{R^{19}M^5}$ (Va) $2\,[M^5]^{(+)}$

The reaction of the fulvene IVb results, analogously to the reaction of IVa, in the formation of the dianion compound Vb

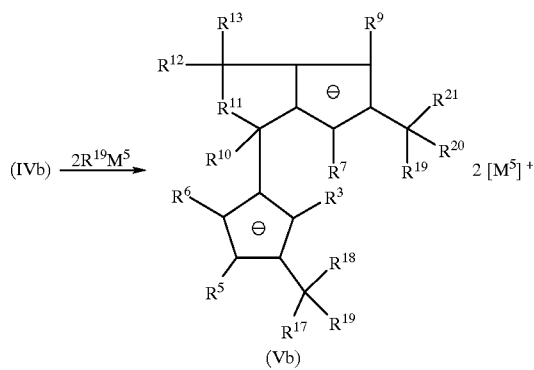

(IVb) $\xrightarrow{2R^{19}M^5}$ (Vb) $2\,[M^5]^+$

The biscyclopentadienyl anions of the formula V can be reacted with compounds $R^{22}_p M^6 X$, in which $M^6$ is an element from main group III-V, X is a leaving group, such as halogen, tosylate or triflate, $R^{22}$ is as defined for $R^{10}$, and p is an integer from 1 to 5.

This is illustrated by the reaction scheme below:

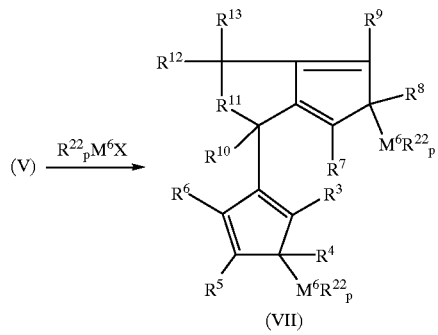

(V) $\xrightarrow{R^{22}_p M^6 X}$ (VII)

The compounds of the formula VII in which at least one of the radicals $R^3$ to $R^6$ and at least one of the radicals $R^7$ to $R^9$ is hydrogen can be converted into the metallocenes according to the invention.

The salts of the formula IIIa can be converted directly into the corresponding dianion compounds of the formula Va by deprotonation using, for example, butyllithium. Conversion into the bridged metallocenes of the formula I is carried out correspondingly to the reaction of V into VI.

Another way of forming the metallocene compounds according to the invention comprises reacting monocyclic or polycyclic ring systems to which a cyclopentadienyl group is fused and which carry functional groups which can serve as leaving groups in substitution reactions (such as, for example, bromide or tosylate) with, for example, cyclopentadienyl- or indenyllithium compounds.

The metallocene compound according to the invention is suitable as highly active catalyst component for the preparation of cycloolefin copolymers.

The present invention accordingly also relates to a process for the preparation of a cycloolefin copolymer by polymerization of at least one polycyclic olefin, at least one acyclic 1-olefin and, if desired, of one or more monocyclic olefins, in the presence of a catalyst comprising at least one cocatalyst and at least one stereorigid metallocene compound, where the stereorigid metallocene compound contains, as ligands, at least two substituted or unsubstituted cyclopentadienyl groups which are bonded to one another via a monocyclic or polycyclic ring system, where at least one cyclopentadienyl group is fused to the monocyclic or polycyclic ring system.

When determining the number of ring atoms in the monocyclic or polycyclic ring system, the carbon atoms of the cyclopentadienyl group(s) fused to the ring system which, due to the fusing, are parts of the ring system are also counted. Substituents on the monocyclic or polycyclic ring system are not counted.

In a preferred embodiment, one cyclopentadienyl group is a substitutent on the monocyclic or polycyclic ring system (ie. the cyclopentadienyl group is bonded to the ring system via a covalent bond), while a further cyclopentadienyl group is fused to the monocyclic or polycyclic ring system.

The monocyclic or polycyclic ring system may be aromatic, aliphatic or mixed aromatic and aliphatic and may also contain heteroatoms, such as nitrogen, oxygen, sulfur, silicon or germanium. It preferably contains 6–40, particularly preferably 6–20, ring atoms, in particular carbon ring atoms. The monocyclic or polycyclic ring system may also carry substituents, such as a $C_1$–$C_{40}$-hydrocarbon-containing group.

Fused cyclopentadienyl groups are monofused (for example via the 1,2- or 1,3-position of the cyclopentadienyl ring) or polyfused (for example via the 1,2,3- or 1,2,3,4-position of the cyclopentadienyl ring), preferably monofused, to the mono- or polycyclic ring system.

The central unit $M^1 R^x_n$ of the metallocene compound according to the invention preferably comprises a transition-metal atom $M^1$, in particular from group IIIb, IVb, Vb or VIb of the Periodic Table of the Elements, which carries n substituents $R^x$, which are identical or different and are preferably a $C_1$–$C_{40}$-hydrocarbon-containing group, a halogen atom, an OH group or a hydrogen atom. The total of the number of substituents $R^x$ and the number of substituted or unsubstituted cyclopentadienyl groups (ligands) corresponds to the valency of the transition-metal atom $M^1$.

Preference is given to compounds of the formula I

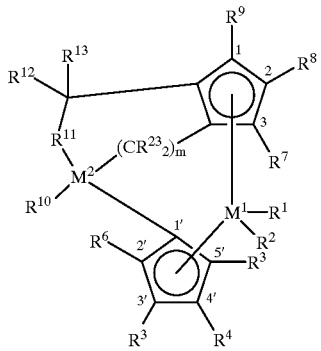

(I)

in which $M^1$ is a metal from group IIIb, IVb, Vb or VIb of the Periodic Table, $M^2$ is carbon, silicon, or germanium, $R^1$ and $R^2$ are identical or different and are a hydrogen atom, a $C_1$–$C_{40}$-hydrocarbon-containing group, such as a $C_1$–$C_{40}$-alkyl group, a $C_1$–$C_{10}$-alkoxy group, a $C_6$–$C_{10}$-aryl group, a $C_6$–$C_{25}$-aryloxy group, a $C_2$–$C_{10}$-alkenyl group, a $C_7$–$C_{40}$-arylalkyl group or a $C_7$–$C_{40}$-arylalkenyl group, an OH group, a halogen atom or $NR^{14}_2$, in which $R^{14}$ is a halogen atom, a $C_1$–$C_{10}$-alkyl group or a $C_6$–$C_{10}$-aryl group, or $R^1$ and $R^2$ together with the atoms connecting them, form a ring system, $R^3$, $R^4$, $R^5$, $R^6$, $R^7$, $R^8$ and $R^9$ are identical or different and are a hydrogen atom, a halogen atom, a $C_1$–$C_{20}$-hydrocarbon-containing group, such as a $C_1$–$C_{10}$-alkyl group, which may be halogenated, a $C_6$–$C_{20}$-aryl group, a $C_6$–$C_{20}$-aryloxy group, a $C_2$–$C_{12}$-alkenyl group, a $C_7$–$C_{40}$-arylalkyl group, a $C_7$–$C_{40}$-alkylaryl group, a $C_8$–$C_{40}$-arylalkenyl group, a —$SiR^{14}_3$, —$NR^{14}_2$, —$SiOR^{14}_3$, —$SiSR^{14}_3$, or —$PR^{14}_2$ radical, in which $R^{14}$ is a halogen atom, a $C_1$–$C_{10}$-alkyl group or a $C_6$–$C_{10}$-aryl group, or two or more adjacent radicals $R^3$, $R^4$, $R^5$, $R^6$, $R^7$, $R^8$ and $R^9$, together with the atoms connecting them, form a ring system preferably containing 4–40, particularly preferably 6–15, carbon atoms, $R^{10}$ is a hydrogen atom, a $C_1$–$C_{40}$-hydrocarbon-containing group, such as a $C_1$–$C_{20}$ alkyl group, a $C_1$–$C_{10}$-alkoxy group, a $C_6$–$C_{20}$-aryl group, a $C_6$–$C_{20}$-aryloxy group, a $C_2$–$C_{12}$-alkenyl group, a $C_7$–$C_{40}$-arylalkyl group, a $C_7$–$C_{40}$-alkylaryl group or a $C_8$–$C_{40}$-arylalkenyl group, each of which may carry —$NR^{14}_3$, —$SiR^{14}_3$, —$SR^{14}_2$ or —$OSiR^{14}_3$ radicals, in which $R^{14}$ is a halogen atom, a $C_1$–$C_{10}$-alkyl group or a $C_6$–$C_{10}$-aryl group, or $R^{10}$ is connected to one or more of the radicals $R^3$, $R^4$, $R^5$ and $R^6$.

$R^{11}$ is

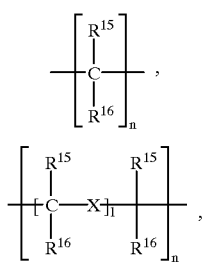

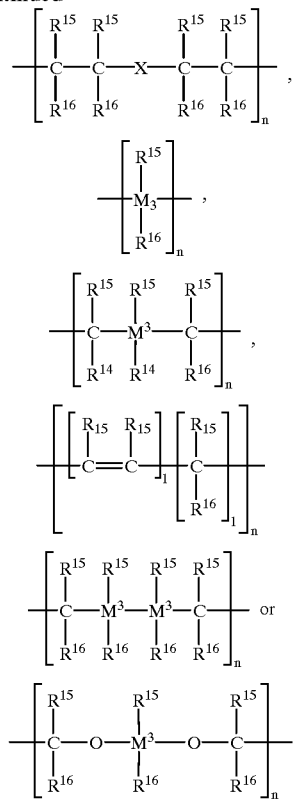

where n is an integer from 1 to 20, l is an integer from 0 to 20, X is O, $=NR^{14}$, $=CO$, $=PR^{14}$, $=P(O)R^{14}$, $=SO$, $=SO_2$ or —S—, in which $R^{14}$ is a halogen atom, a $C_1$–$C_{10}$-alkyl group or a $C_6$–$C_{10}$-aryl group, $R^{15}$ and $R^{16}$ are identical or different and are a hydrogen atom, a halogen atom or a $C_1$–$C_{40}$-hydrocarbon-containing group, such as a $C_1$–$C_{10}$-alkyl group, a $C_1$–$C_{10}$-fluoroalkyl group, a $C_1$–$C_{10}$-alkoxy group, a $C_6$–$C_{10}$-aryl group, a $C_6$–$C_{10}$-fluoroaryl group, a $C_6$–$C_{10}$-aryloxy group, a $C_2$–$C_{10}$-alkenyl group, a $C_7$–$C_{40}$-arylalkyl group, a $C_7$–$C_{40}$-alkylaryl group, or a $C_8$–$C_{40}$-arylalkenyl group or two radicals $R^{15}$, two radicals $R^{16}$ and $R^{15}$ and $R^{16}$, in each case together with the atoms connecting them, form one or more rings, and $M^3$ is silicon, germanium or tin, $R^{12}$ and $R^{13}$ are identical or different and are a hydrogen atom, a $C_1$–$C_{40}$-hydrocarbon-containing group, such as a $C_1$–$C_{20}$-alkyl group, a $C_1$–$C_{10}$-alkoxy group, a $C_6$–$C_{20}$-aryl group, a $C_6$–$C_{20}$-aryloxy group, a $C_2$–$C_{12}$-alkenyl group, a $C_7$–$C_{40}$-arylalkyl group, a $C_7$–$C_{40}$-alkylaryl group or a $C_8$–$C_{40}$-arylalkenyl group, each of which may carry —$NR^{14}_3$, —$SR^1_2$, —$SiR^{14}_3$ or —$OSiR^{14}_3$ radicals, in which $R^{14}$ is a halogen atom, a $C_1$–$C_{10}$-alkyl group or a $C_6$–$C_{10}$-aryl group, or may carry halogen, $R^{23}$ is identical or different and is a hydrogen atom, a halogen atom or a $C_1$–$C_{40}$-hydrocarbon-containing group, such as a $C_1$–$C_{10}$-alkyl group, a $C_1$–$C_{10}$-alkoxy group, a $C_6$–$C_{10}$-aryl group, a $C_6$–$C_{25}$-aryloxy group, a $C_2$–$C_{10}$-alkenyl group, a $C_7$–$C_{40}$-arylalkyl group or a $C_7$–$C_{40}$-arylalkenyl group, or one or more radicals $R^{23}$ are bonded to one or both radicals $R^{15}$ an $R^{16}$ and/or to one or more radicals $R^{10}$, $R^{11}$, $R^{12}$ and $R^{13}$, and m is an integer from 0 to 24.

In the case where $M^2$ is C, m is 0 and $R^{11}$ is $CH_2$, at least one of the radicals $R^4$, $R^8$, $R^{10}$, $R^{12}$ and $R^{13}$ is not alkyl and/or at least one of the radicals $R^3$, $R^5$, $R^6$, $R^7$ and $R^9$ is not hydrogen.

For compounds of the formula I, it is preferred that
$M^1$ is zirconium or hafnium, in particular zirconium,
$R^1$ and $R^2$ are identical and are a $C_1$–$C_3$-alkyl group or a halogen atom, in particular chlorine,
$R^3, R^4, R^5, R^6, R^7, R^8$ and $R^9$ are identical or different and are a hydrogen atom, a $C_1$–$C_{10}$-alkyl group or a $C_6$–$C_{24}$-aryl group, or two or more adjacent radicals, together with the atoms connecting them, form an aromatic or aliphatic hydrocarbon ring system,
$R^{10}$ is a hydrogen atom, a $C_6$–$C_{24}$-aryl group or a $C_1$–$C_{10}$-alkyl group, in particular a $C_1$–$C_4$-alkyl group,
$R^{11}$ is
$R^{11}$

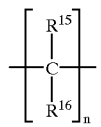

wherein
n is an integer from 1 to 8, in particular from 2 to 4,
$R^{15}$ and $R^{16}$ are identical or different and are hydrogen or a $C_1$–$C_{10}$-alkyl group, or two radicals $R^{15}$, two radicals $R^{16}$ or $R^{15}$ and $R^{16}$, together with the atoms connecting the, form a hydrocarbon ring system,
$M^2$ is carbon,
$R^{12}$ and $R^{13}$ are identical or different and are a hydrogen atom, a $C_1$–$C_{10}$-alkyl group, in particular a $C_1$–$C_4$-alkyl group, or a $C_6$–$C_{10}$-aryl group, and
m is 0.

Particular preference is given to compounds of the formula I in which
$M^1$ is zirconium,
$R^1$ and $R^2$ are identical and are a halogen atom, in particular chlorine,
$R^3, R^4, R^5, R^6, R^7, R^8$ and $R^9$ are identical or different and are hydrogen or a $C_1$–$C_4$-alkyl group, such as methyl, ethyl, propyl, ispropyl, butyl or isobutyl, or a $C_6$–$C_{14}$-aryl group, such as phenyl or naphthyl or $R^8$ and $R^9$ and $R^3$ and $R^4$ and/or $R^5$ and $R^6$, together with the atoms connecting them, form an aromatic hydrocarbon ring system, in particular a six-membered ring, which may itself be substituted,
$M^2$ is a carbon atom,
$R^{10}$ is a $C_1$–$C_6$-alkyl group, in particular methyl
$R^{11}$ is —$CH_2$—$CH_2$—,
$R^{12}$ and $R^{13}$ are identical or different and are a methyl or phenyl group, and
m is 0.

Preferably, at least one of the radicals $R^3$ to $R^9$, in particular at least one of the radicals $R^4$, $R^5$ and $R^8$, is other than hydrogen, in particular if $R^{11}$ is —$CH_2$—$CH_2$—.

Examples of metallocenes which can be employed in the process according to the invention are given in the above-mentioned list. In addition, it is also possible to employ compounds such as (4-($\eta^5$-3-t-butylcyclopentadienyl)-4,6,6-trimethyl-($\eta^5$-2-t-butyl-4,5-tetrahydropentalene)dichlorozirconium
(4-($\eta^5$-cyclopentadienyl)-4,6,6-trimethyl-($\eta^5$-4,5-tetrahydropentalene)dichlorozirconium, silicon-bis($\eta^5$-(2-propanediyl)cyclopentadienyl)dichlorozirconium, silicon-bis($\eta^5$-(2-propanediyl)cyclopentadienyl)dichlorozirconium or germanium-bis($\eta^5$-(2-propanediyl)-2-methylcyclopentadienyl)dichlorozirconium.

The metallocenes employed in the process according to the invention are highly active catalyst components for the preparation of cycloolefin copolymers.

Depending on the substitution pattern of the ligands, the metallocenes according to the invention can be formed as an isomer mixture. The metallocenes are preferably employed in isomerically pure form. The use of the racemate is in most cases sufficient.

However, it is also possible to use the pure enantiomer in the (+) or (−) form. Using the pure enantiomers, an optically active polymer can be prepared.

Cycloolefin copolymers are preferably prepared using a catalyst comprising at least one metallocene compound and a cocatalyst. It is also possible to use mixtures of two or more metallocene compounds, in particular for the preparation of reactor blends or of cycloolefin copolymers having a broad or multimodal molecular weight distribution.

The cocatalyst employed is preferably an aluminoxane, which preferably has the formula VIIIa for the linear type and/or the formula VIIIb for the cyclic type,

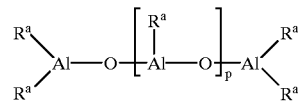 (VIIIa)

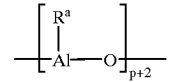 (VIIIb)

where, in the formula VIIIa and VIIIb, the radicals $R^a$ are identical or different and are a $C_1$–$C_6$-alkyl group, a $C_6$–$C_{18}$-aryl group, benzyl or hydrogen, and p is an integer from 2 to 50, preferably 10 to 35.

The radicals $R^a$ are preferably identical and are preferably methyl, isobutyl, phenyl or benzyl, particularly preferably methyl.

If the radicals $R^a$ are different, they are preferably methyl and hydrogen or alternatively methyl and isobutyl, where hydrogen or isobutyl is preferably present to the extent of 0.01–40% (number of radicals $R^a$).

The aluminoxane can be prepared in various ways by known processes. One of the methods is, for example, to react an aluminum hydrocarbon compound and/or a hydridoaluminum hydrocarbon compound with water (in gas, solid, liquid or bound form—for example as water of crystallization) in an inert solvent (such as, for example toluene). In order to prepare an aluminoxane containing different alkyl groups $R^a$, two different trialkylaluminum compounds ($AlR_3$+$AlR'_3$) according to the desired composition are reacted with water (S. Pasynkiewicz, Polyhedron 9 (1990), 429, EP-A 302 424). The precise spatial structure of the aluminoxanes is unknown.

Irrespective of the preparation method, all aluminoxane solutions have in common a varying content of unreacted aluminum starting compound, which is in free form or as an adduct.

It is also possible to apply the aluminoxane to a support and then to employ it in supported form as a suspension. A number of processes for supporting are known (EP 578 838), for example silica gel can function as support.

It is possible to preactivate the metallocene by means of a cocatalyst, in particular an aluminoxane, before use in the polymerization reaction.

The preactivation of the transition-metal compound is carried out in solution. The metallocene is preferably dissolved in a solution of the aluminoxane in an inert hydrocarbon. Suitable inert hydrocarbons are aliphatic or aromatic hydrocarbons. Toluene is preferred.

The concentration of the aluminoxane in the solution is in the range from about 1% by weight to the saturation limit, preferably from 5 t0 30% by weight, in each case based on the total amount of solution. The metallocene can be employed in the same concentration, but is preferably employed in the same concentration, but is preferably employed in an amount of from $10^{-4}$ to 1 mol per mol of aluminoxane. The preactivation is carried out for from 5 minutes to 60 hours, preferably for from 5 to 60 minutes. The temperature is −78 to 100° C., preferably from 0 to 70° C.

The metallocene can be used to carry out a prepolymerization, preferably using the (or one of the) olefin(s) employed in the polymerization.

The metallocene can also be applied to a support. Suitable supports are, for example, silica gels, aluminum oxides, solid aluminoxane or other inorganic support materials. Another suitable support material is a polyolefin powder in finely divided form.

A further possible variant of the process according to the invention comprises using a salt-like compound of the formula $BR_3$, $R_xNH_{4-x}BR'_4$ or $R_3PHBR'_4$ as cocatalyst instead of or in addition to an aluminoxane. In these formulae, x=1, 2 or 3, each R=alkyl or aryl, which preferably has 1–20 carbon atoms and is identical to or different from the others, and R'=aryl, which preferably has 1–20 carbon atoms and is identical to or different from the others and may also be fluorinated or partially fluorinated. In this case, the catalyst comprises the product of the reaction of a metallocene with one of said compounds (EP-A 277 004).

Any solvent added to the reaction mixture is a commercial inert solvent, such as, for example, an aliphatic or cycloaliphatic hydrocarbon, a petroleum or hydrogenated diesel oil fraction or toluene.

The metallocenes are preferably employed in the form of their racemates. The metallocene compound is preferably used in a concentration, based on the transition metal, of from $10^{-3}$ to $10^{-8}$, mol, preferably from $10^{-4}$ to $10^{-7}$ mol, of transition metal per $dm^3$ of reactor volume. The aluminoxane is used in a concentration of from $10^{-4}$ to $10^{-1}$ mol, preferably from $10^{-4}$ to $2*10^{-2}$ mol, per $dm^3$ of reactor volume, based on the aluminum content. In principle, however, higher concentrations are also possible.

The process according to the invention is carried out using at least one polycyclic olefin, preferably of the formulae IX, X, XI, XII, XIII or XIV,

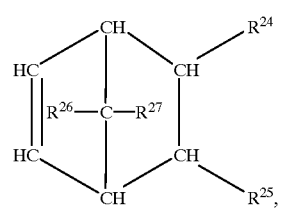
(IX)

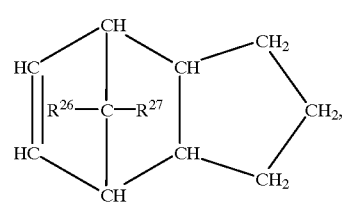
(X)

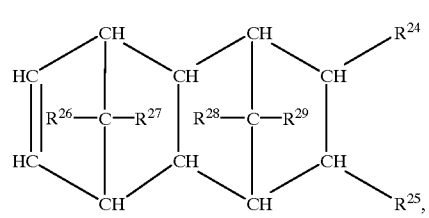
(XI)

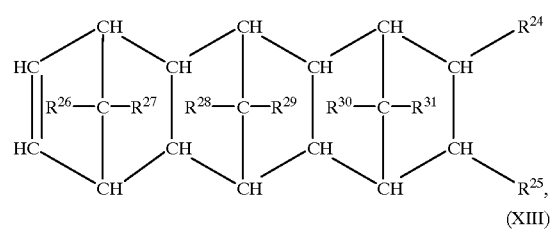
(XII)

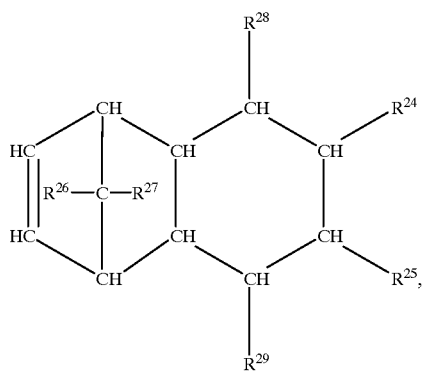
(XIII)

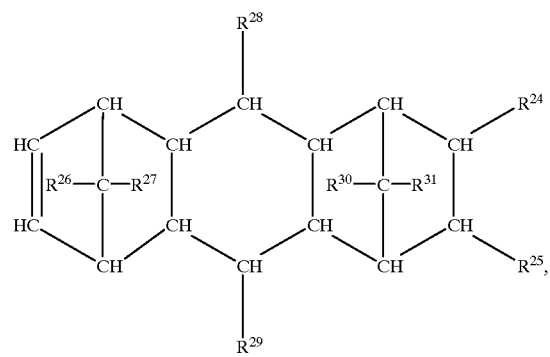
(XIV)

in which $R^{24}$, $R^{25}$, $R^{26}$, $R^{27}$, $R^{28}$, $R^{29}$, $R^{30}$ and $R^{31}$ are identical or different and are a hydrogen atom or a $C_1$–$C_{20}$-hydrocarbon radical, such as $C_1$–$C_8$-alkyl or $C_6$–$C_{10}$-aryl or two or more radicals $R^{24}$–$R^{31}$ together are a $C_4$–$C_{40}$-ring system, where identical radicals $R^{24}$–$R^{31}$ in the various formulae can have different meanings. Particular preference is given to cycloolefins of the formula VIII or X in which $R^{24}$, $R^{25}$, $R^{26}$, $R^{27}$, $R^{28}$, $R^{29}$, $R^{30}$ and $R^{31}$ are identical or different and are a hydrogen atom or a $C_1$–$C_2$-hydrocarbon radical, in particular a $C_6$–$C_{10}$-aryl radical or a $C_1$–$C_8$-alkyl radical, where identical radicals $R^{24}$–$R^{31}$ in the various formulae can have different meanings.

If desired, a monocyclic olefin of the formula XV

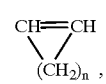
(XV)

in which n is a number from 2 to 10, is also used in the preparation of cycloolefin copolymers.

In addition one or more acyclic 1-olefins preferably of the formula XVI

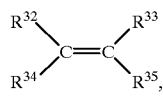

(XVI)

in which $R^{32}$, $R^{33}$, $R^{34}$ and $R^{35}$ are identical or different and are a hydrogen atom or a $C_1$–$C_{20}$-hydrocarbon radical, preferably a $C_6$–$C_{10}$-aryl radical or a $C_1$–$C_8$-alkyl radical, are employed in the preparation of cycloolefin copolymers. Preference is given to ethylene.

In particular, copolymers of polycyclic olefins, preferably of the formulae IX and XI, with ethylene are prepared.

Particularly preferred polycyclic olefins are norbornene and tetracyclododecene, it being possible for these to be substituted by ($C_1$–$C_6$)-alkyl. They are preferably copolymerized with ethylene; ethylene-norbornene copolymers are of particular importance.

The polycyclic olefin is employed in an amount of from 0.1 to 99.9% by weight, the monocyclic olefin in an amount of from 0 to 99.9% by weight, and the acyclic olefin in an amount of from 0.1 to 99.9% by weight, in each case based on the total amount of the monomers.

The concentration of the acyclic olefin employed is determined by its solubility in the reaction medium at a given pressure and temperature.

Polycyclic olefins, monocyclic olefins and acyclic olefins are also taken to mean mixtures of two or more olefins of the particular type. This means that tercopolymers and multicopolymers in addition to polycyclic bicopolymers can be prepared by the process according to the invention. Copolymers of monocyclic olefins and acyclic olefins can also be obtained by the process described.

Of the monocyclic olefins, cyclopentene, which may be substituted, is preferred.

The process according to the invention is preferably carried out at temperatures of from −78 to 150° C., in particular from 0 to 100° C., and a pressure of from 0.01 to 64 bar.

The polymerization is carried out in the liquid cycloolefin itself or in cycloolefin solution, the pressure expediently being above 1 bar.

In the preparation of copolymers, the molar ratios between the polycyclic olefin and the open-chain olefin employed can be varied within a broad range. Molar ratios between the cycloolefin and open-chain olefin of from 3:1 to 100:1 are preferred. The choice of polymerization temperature, the concentration of the catalyst components and the molar ratio employed or the pressure of the gaseous, open-chain olefin allow the incorporation rate of comonomer to be controlled virtually as desired. Preference is given to incorporation rates of between 20 and 80 mol % of the cyclic components, and particular preference is given to incorporation rates of between 40 and 60 mol % of the cyclic components.

The polymerization can also be carried out in more than one step, it also being possible for block copolymers to be formed (EP 560 090).

The mean molecular weight of the polymer formed can be further controlled in a known manner by metering in hydrogen, varying the catalyst concentration or varying the temperature.

The polydispersity $M_w/M_n$ of the cycloolefin copolymers is fairly narrow, having values of from 1.9 to 3.5. This results in a property profile which makes them particularly suitable for injection molding.

The process according to the invention can be used to prepare amorphous cycloolefin copolymers containing no partially crystalline ethylene polymers. The copolymers are transparent, rigid and thermoplastic. The yield stresses (in accordance with DIN 53457) are in the range from 50 to 100 MPa, preferably between 55 and 70 MPa. Both during extrusion and during injection molding, neither decomposition reactions nor a reduction in viscosity were found at temperatures of 300° C.

The cycloolefin copolymers prepared according to the invention are particularly suitable for the production of moldings, such as extruded parts (for example films, tubes, pipes, rods and fibers) or injection-molded articles of any desired shape and size. The films can be extruded films, calendered films, cast films, monoaxially and biaxially oriented films or multilayer films and are particularly suitable as foodstuff packaging films or blister packs. They have a high water barrier action and low gas permeability. The cycloolefin copolymers prepared according to the invention are also suitable as additives in other polymer films (in particular polyolefin films, such as polypropylene films or polyethylene films), for example for the purposes of flow improvement, paintability improvement, modification of the modulus of elasticity and the production of opaque films. An important property of the cycloolefin copolymers prepared according to the invention is their transparency. In particular, optical applications of the extruded or injection-molded parts made of cycloolefin copolymers thus have considerable importance. The refractive index, determined using an Abbe refractometer and mixed light, of the reaction products described in the examples below is in the range between 1.520 and 1.555. Since the refractive index is very close to that of crown glass (n=1.51), the products according to the invention can have various applications as glass substitutes, such as, for example, lenses, prisms, support sheets and films for optical data-storage media, for video disks, for compact disks, as cover sheets and focusing screens for solar cells, as cover sheets and diffuser screens for high-performance optics, and as optical waveguides in the form of fibers or films.

In impact-modified form, the cycloolefin copolymers prepared according to the invention can be employed as structural materials in various industrial areas (EP 566 988).

The cycloolefin copolymers obtained according to the invention can also be employed for the preparation of polymer alloys. The alloys can be prepared in the melt or in solution. Each of the alloys has a property combination of the components which is favorable for certain applications. For alloys containing the cycloolefin copolymers according to the invention, the following polymers can preferably be employed:

Polyethylene, polypropylene, ethylene-propylene copolymers, polybutylene, poly(4-methyl-1-pentene), polyisoprene, polyisobutylene, natural rubber, poly(methyl methacrylate), other polymethacrylates, polyacrylates, acrylate-methacrylate copolymers, polystyrene, styrene-acrylonitrile copolymers, bisphenol A polycarbonate, other polycarbonates, aromatic polyester carbonates, polyethylene terephthalate, polybutylene terephthalate, amorphous polyarylates, nylon 6, nylon 66, other polyamides, polyaramides, polyether ketones, polyoxymethylene, polyoxyethylene, polyurethanes, polysulfones, polyether sulfones and polyvinylidene fluoride.

The process according to the invention gives, with high activity, particularly transparent cycloolefin copolymers which have high tear strengths.

The glass transition temperatures Tg quoted in the examples below were determined by DSC (Differential Scanning Calorimetry) at a heating rate of 20° C./min. The viscosity indices quoted were determined in accordance with DIN 53728. The mechanical properties were determined in a tensile test (DIN 53457, Instron 4302).

As the measure of a catalyst activity, the yield of polymer per time unit and per mmol of metallocene is used:

$$\text{Activity} = \frac{\text{polymer [g]}}{\text{time unit [h]} \times \text{amount of metallocene [mmol]}} = A^*$$

General information: the preparation and handling of organometallic compounds were carried out in the absence of air and moisture under an argon blanket (Schlenk technique). All the solvents required were rendered absolute before use by boiling for several hours over a suitable desiccant, followed by distillation under argon.

The diketones and keto-aldehydes employed as starting compounds were prepared by methods known from the literature. Cyclopentadiene and methylcyclopentadiene were obtained by cracking the dimers and were stored at −35° C.

The Al/CH$_3$ ratio in the aluminoxane was determined by decomposing the sample using H$_2$SO$_4$ and measuring the volume of hydrolysis gas produced under standard conditions and by complexometric titration of the aluminum in the sample, which had then dissolved, by the Schwarzenbach method.

The compounds were characterized by $^1$H-NMR, $^{13}$C-NMR and IR spectroscopy.

The examples below serve to illustrate the invention, but do not represent a limitation:

A. Preparation of the Bisfulvenes II

EXAMPLE 1a

Synthesis of 2,5-Bis(2,4-cyclopentadien-1-ylidene) hexane

In a modified reaction procedure [a], 11.0 g (96.3 mmol) of 2,5-hexanedione and 12.7 g (193 mmol) of freshly cracked cyclopentadiene are dissolved in 60 ml of methanol, the solution is cooled to 0° C., and 8.60 g (121 mmol) of pyrrolidine are added. The reaction solution is stirred at 0° C. for 90 minutes, hydrolyzed using 5 ml of glacial acetic acid and 50 ml of water, and extracted twice with 70 ml of diethyl ether in each case, and the combined organic phases are washed with saturated sodium chloride solution and dried over magnesium sulfate, giving, after removal of the solvent in vacuo, 18.0 g (89%) of the difulvene as an orange-red, oily residue.

[a]=M. S. Erickson, J. M. Cronan, J. G. Garcia, M. L. McLaughlin, J. Org. Chem. 57 (1992) 2504–2508. K. J. Stone, R. D. Little, J. Org. Chem. 49 (1984) 1849–1853.

EXAMPLE 1b

Synthesis of 2,5-Bis(cyclopenta-2,4-dien-1-ylidene) undecane

A solution of 3.50 g (19.9 mmol) of 2,5-undecanedione in 100 ml of methanol and 10 ml of tetrahydrofuran is cooled to 0° C., and 3.92 ml (3.14 g, 47.5 mmol) of freshly cracked cyclopentadiene are added. 6.28 ml (5.40 g, 76.0 mmol) of freshly distilled pyrrolidine are then added dropwise to the orange-red, clear reaction solution over the course of 10 minutes. The reaction solution changes color to dark red within 10 minutes. The mixture is then allowed to warm to room temperature and stirred for a further 3 days in order to complete the reaction. For work-up, the pyrrolidine is neutralized using 4 ml of glacial acetic acid and hydrolyzed using 100 ml of water. The mixture is extracted twice with 100 ml of pentane in each case, the combined organic phases are washed a number of times with saturated, aqueous sodium chloride solution and dried over magnesium sulfate. Removal of the solvent in vacuo gives the cyclopentadienylidene (2) as a dark red oil in a crude yield of 78% (4.16 g).

Purification by column chromatography over silica gel acid deactivated by means of triethylamine, and pentane:diethyl ether (100:1) as eluting solvent mixture gives the difulvene (2) as an orange oil.

B. Synthesis of the Bridged Biscyclopentadienyl Anions V

EXAMPLE 2

Synthesis of [4-($\eta^5$-Cyclopentadienyl)-4,7,7-trimethyl($\eta^5$-4,5,6,7-tetrahydroindenyl)]dilithium 62.4 ml (99.8 mmol) of an ethereal 1.60 M methyllithium solution are slowly added dropwise at 0° C. with vigorous stirring to a solution of 10.0 g (47.5 mmol) of 2,5-bis(2,4-cyclopentadien-1-ylidene)hexane in 150 ml of diethyl ether. The mixture is allowed to warm to room temperature and is stirred for 24 hours, giving a beige precipitate. Filtration through a frit and repeated washing with pentane give 13.2 g (89%) of the dilithium salt as a beige powder coordinated with one mole-equivalent of diethyl ether.

EXAMPLE 3

Synthesis of 4-($\eta^5$-Cyclopentadienyl)-4,7-dimethyl-7-phenyl($\eta^5$-4,5,6,7-tetrahydroindenyl)dilithium An ethereal solution of phenyllithium (83.4 ml, 74.3 mol, 0.89 M diethyl ether solution) is added dropwise at 0° C. to a solution of 7.10 g (33.7 mmol) of difulvene (Example 1) in 100 ml of diethyl ether. After about 5 minutes, a beige precipitate stars to deposit. The mixture is allowed to warm to room temperature, and is then stirred for a further 12 hours at 25° C. Filtration through a frit, repeated washing with pentane and drying in an oil-pump vacuum give the dilithium salt as a beige, very hydrolysis-sensitive powder in a yield of 82% (10.3 g).

EXAMPLE 4

Synthesis of 4-($\eta^5$-Cyclopentadienyl)-4,7-dimethyl-7-butyl($\eta^5$-4,5,6,7-tetrahydroindenyl)dilithium A solution of 15.0 g (71.3 mmol) of difulvene (Example 1), dissolved in 100 ml of diethyl ether, is cooled to −30° C., and 94 ml (150 mmol) of a 1.60 M solution of n-butyllithium in hexane is added slowly with vigorous stirring. A lemon-yellow precipitate forms. The mixture is allowed to warm to room temperature, and is stirred for a further 24 hours in order to complete the reaction. The resultant precipitate is then filtered off, washed several times with pentane and dried in an oil-pump vacuum, giving 23.0 g (91%) of the dilithium salt as a beige, very hydrolysis-sensitive powder to which one mole-equivalent of diethyl ether is coordinated.

C. Synthesis of the Bridged Cyclopentadiene IV

EXAMPLE 5

Synthesis of 7-Cyclopentadienyl-4,4,7-trimethyl-4,5,6,7-tetrahydro-1H-indene 50 ml of degased water are added dropwise at 0° C. to a suspension of 7.35 g (23.5 mmol) of the dilithium salt (Example 2) in 50 ml of diethyl ether. During this addition, the beige suspension disappears immediately, giving a clear, orange diethyl ether phase. The phases are subsequently separated in a separating funnel, the aqueous phase is extracted twice with 25 ml of diethyl ether in each case, and the combined organic phases are washed with 20 ml of a saturated sodium chloride solution. Drying over magnesium sulfate and removal of the solvent in vacuo give 5.1 g (96%) of the hydrolyzed product as an orange-red oil.

EXAMPLE 6

Preparation of 7-Cyclopentadienyl-4,7-dimethyl-4-phenyl-4,5,6,7-tetrahydro-1H-indene A yellow suspension, cooled to 0° C., of 3.64 g (9.72 mmol) of the dilithium salt (Example 3) in 50 ml of diethyl ether is hydrolyzed by slow addition of 20 ml of degased water. During this addition, the suspension disappears, giving an orange, clear reaction solution. After the mixture has been extracted twice with 20 ml of diethyl ether in each case, the combined organic phases are washed several times with saturated, aqueous sodium chloride solution and dried over magnesium sulfate. Subsequent removal of the solvent in vacuo gives the hydrolyzed product as an orange oil in a yield of 94% (2.62 g).

EXAMPLE 7

Preparation of 7-Cyclopentadienyl-4,7-dimethyl-4-butyl-4,5,6,7-tetrahydro-1H-indene A yellow suspension, cooled to 0° C., of 5.00 g (17.33 mmol) of the dilithium salt (Example 4) in 50 ml of diethyl ether is hydrolyzed by slow addition of 20 ml of degased water. During this addition, the suspension disappears, giving an orange, clear reaction solution. After the mixture has been extracted twice with 20 ml of diethyl ether in each case, the combined organic phases are washed several times with saturated, aqueous sodium chloride solution and dried over magnesium sulfate. Subsequent removal of the solvent in vacuo gives the hydrolyzed product as an orange oil in a yield of 96% (4.59 g).

D. Synthesis of Bridged Cyclopentadiene-Fulvene Ligands IVa by Subsequent Introduction of Substituents (Introduction of Various Radicals $R^{13}$, $R^{17}$, $R^{18}$, $R^{20}$ and $R^{21}$)

EXAMPLE 8a

Synthesis of 7-(3'-Isopropylidenecyclopenta-1,4-dienyl)-4,4,7-trimethyl-4,5,6,7-tetrahydro-1H-indene 7.70 g (34.0 mmol) of the cyclopentadienyltetrahydroindene (Example 5) are dissolved in 70 ml of methanol and cooled to 0° C. The orange-red reaction solution is subsequently treated successively with 2.96 g (51.0 mmol) of acetone and 4.83 g (68.0 mmol) of pyrrolidine. The mixture is stirred at 0° C. for 5 hours and then, in order to complete the reaction, at room temperature for a further 2 hours, before the reaction is terminated by addition of 4 ml of glacial acetic acid. The red, clear reaction solution is hydrolyzed by means of 200 ml of water, and the yellow suspension is extracted 3× with 50 ml of diethyl ether in each case. Repeated washing of the combined organic phases with saturated, aqueous sodium chloride solution and drying over magnesium sulfate give the fulvene as an orange-red, wax-like residue in a yield of 88% (8.00 g).

EXAMPLE 8b

Preparation of 4-Cyclopentadienyl-4,7-dimethyl-7-allyl-4,5,6,7-tetrahydro-1H-indene 293 ml of a 0.60 M solution of the allyl Grignard reagent (175 mmol) in diethyl ether are added dropwise over the course of 1 hour with vigorous stirring to a solution of 16.8 g (79.8 mmol) of 2,5-bis(2,4-cyclopentadien-1-ylidene) hexane (Example 1) dissolved in 100 ml of diethyl ether and 50 ml of tetrahydrofuran. When the addition is complete, the mixture is stirred overnight at room temperature, before the yellow-orange suspension is cooled to 0° C. and carefully hydrolyzed by means of aqueous, saturated ammonium chloride solution. The organic phase is separated off, washed three times with 50 ml of saturated, aqueous sodium chloride solution in each case and subsequently dried over magnesium sulfate. Removal of the solvent in an oil-pump vacuum gives 17.5 g of the product as an orange oil (87%).

E. Synthesis of the Dianion Complexes Va

EXAMPLE 9a

Synthesis of 4-[3'-t-Bu-($\eta^5$-cyclopentadienyl)]-4,7,7,-trimethyl($\eta^5$-tetrahydroindenyl)dilithium During the reaction of the tetrahydroindenylfulvene (Example 8) with an ethereal solution of methyllithium (2 equivalents) at 0° C., an intense yellow precipitate is obtained after only a few seconds. The mixture is stirred at room temperature for a further 12 hours, filtered through a frit, washed with pentane and dried in an oil-pump vacuum, giving a dilithium salt, which is further reacted directly without further characterization.

EXAMPLE 9b

Synthesis of [4-$\eta^5$-Cyclopentadienyl)-4,7-dimethyl-7-allyl($\eta^5$-4,5,6,7-tetrahydroindenyl)]dilithium 10.5 of the allyl Grignard product (Example 10) are dissolved in 100 ml of diethyl ether, the solution is cooled to 0° C., and 57.6 ml of n-butyllithium solution (1.60 M in hexane, 92.0 mmol) are added dropwise. After the mixture has been stirred at room temperature for 18 hours, the yellow-beige residue is filtered off, washed several times with pentane and dried in an oil-pump vacuum. The dilithium salt is isolated in qualitative yield as a beige solid and is coordinated with one mole-equivalent of diethyl ether.

F. Synthesis of the Metallocenes of Formula I

EXAMPLE 10

Synthesis of 4-($\eta^5$-Cyclopentadienyl)-4,7,7,-trimethyl($\eta^5$-4,5,6,7-tetrahydroindenyl)] dichlorozirconium 7.50 g (32.2 mmol) of zirconium tetrachloride are added in portions over the course of 10 minutes to a suspension, cooled to −78° C., of 9.58 g (30.7 mmol) of the dilithium compound (Example 2) in 200 ml of toluene. After the mixture has been stirred at room temperature for 50 hours, the precipitate is filtered off via a frit, and the orange filtrate is evaporated to dryness in vacuo. Repeated washing with pentane gives 4.38 g of the zirconocene dichloride as an orange-yellow powder in a crude yield of 37%.

For purification, the orange-yellow powder is extracted for several days with pentane in a circulation frit, giving, after removal of the solvent in an oil-pump vacuum, 1.70 g (14%) of the zirconocene dichloride as a yellow powder: m.p. 223° C. (decomp., DSC).

EXAMPLE 11

Synthesis of 4-($\eta^5$-Cyclopentadienyl)-4,7,7,-trimethyl($\eta^5$-4,5,6,7-tetrahydroindenyl) dichlorotitanium A suspension of 5.46 g (17.5 mmol) of the dilithium etherate (Example 2) in 200 ml of toluene is cooled to −78°

C., and 3.3 g (17.5 mmol) of titanium chloride are added. The reaction solution immediately becomes a dark red color. The mixture is stirred at room temperature for 30 hours, insoluble constituents are removed by filtration through a frit, and the dark-red toluene phase is evaporated to dryness in an oil-pump vacuum. Repeated washing with pentane gives 1.85 g of the titanocene dichloride as a brown-beige powder. The crude product is subsequently extracted for several days with pentane in a circulation frit, giving, after removal of the solvent, the titanocene dichloride as a brown solid in a yield of 13% (780 mg); m.p. 259° C. (decomp., DSC).

EXAMPLE 12

Synthesis of [4-($\eta^5$-Cyclopentadienyl)-4,7,7-trimethyl-($\eta^5$-4,5,6,7-tetrahydroindenyl)] dichlorozirconium from 2,5-bis(2,4-cyclopentadien-1-ylidene)hexane 62.4 ml (99.8 mmol) of an ethereal 1.60 M solution of methyllithium is slowly added at 0° C. with vigorous stirring to a solution of 10.0 g (47.5 mmol) of 2,5-bis(2,4-cyclopentadien-1-ylidene)hexane (Example 1) in 150 ml of toluene. When the addition is complete, the mixture is stirred at room temperature for 24 hours and then cooled to −30° C., and 9.32 g (40 mmol) of zirconium tetrachloride are added. After the mixture has been stirred at room temperature for 30 hours, LiCl is filtered off, and the filtrate is evaporated to dryness in vacuo. Repeated washing with pentane give 4.02 g (26%) of the zirconium dichloride.

EXAMPLE 13

Synthesis of the Two Diastereomers of 4-($\eta^5$-Cyclopentadienyl)-4,7-dimethyl-7-phenyl($\eta^5$-4,5,6,7-tetrahydroindenyl)dichlorozirconium 2.72 g (11.7 mmol) of zirconium tetrachloride are added in portions to a suspension, cooled to −78° C., of 4.37 g (11.7 mmol) of the dilithium salt (Example 3) in 200 ml of toluene. The mixture is allowed to warm to room temperature, and the orange suspension is stirred at 20° C. for a further 20 hours. The mixture is filtered, the solvent is removed from the filtrate in an oil-pump vacuum, and the orange-red, oily residue is powdered by vigorous stirring in 20 ml of pentane. Removal of the pentane in vacuum subsequently gives 2.64 g (50%) of the zirconocene dichloride as a yellow-orange powder. The $^1$H-NMR spectrum of the crude product suggests a diastereomer ratio of—8:1.

EXAMPLE 14

Synthesis of the Two Diastereomers of 4-($\eta^5$-Cyclopentadienyl)-4,7-dimethyl-7-butyl($\eta^5$-4,5,6,7-tetrahydroindenyl)dichlorozirconium A suspension of 7.80 g (22.0 mmol) of the dilithium salt (Example 4) in 200 ml of toluene is cooled to −78° C., and 5.10 g (22.0 mmol) of zirconium tetrachloride are added in portions. The mixture is allowed to warm to room temperature, and the yellow-orange suspension is stirred for a further 48 hours. Insoluble constituents are filtered off via a frit, and the solvent is removed in an oil-pump vacuum. The red-orange oil is powdered by vigorous stirring with pentane, giving the zirconocene dichloride in a crude yield of 30% (2.72 g).

Purification is effected by extracting the crude product with pentane for several days in a circulation frit. The $^1$H-NMR spectrum of the fine, yellow precipitate indicates two sets of signals in a ratio of 15:1. A few crystals can be isolated from the yellow, concentrated filtrate by storage at −30° C. These crystals of the diastereomerically pure zirconocene dichloride (pR, 4R, 7R)-4-($\eta^5$-cyclopentadienyl-4,7-dimethyl-7-butyl-($\eta^5$-4,5,6,7-tetrahydroindenyl) dichlorozirconium) enable individual sets of signals in the $^1$H-NMR to be assigned. The crystals which have crystallized from the pentane solution correspond to the diastereomer formed in the lesser amount. Crystals can also be isolated from the 1.35 g (14%) of the yellow, fine powder by dissolving approximately 100 mg of powder in a little methylene chloride and allowing extremely slow crystallization by diffusion of pentane into this solution. The major product is the other diastereomer.

EXAMPLE 15

Synthesis of 4-($\eta^5$-Cyclopentadienyl)-4,7-dimethyl-7-butyl($\eta^5$-4,5,6,7-tetrahydroindenyl) dichlorohafnium 1.81 g (5.65 mmol) of hafnium tetrachloride are added to a suspension, cooled to −78° C., of 2.00 g (5.64 mmol) of the dilithium salt (Example 4) in 150 ml of toluene. The orange suspension is allowed to warm to room temperature, and is stirred for a further 2 days in order to complete the reaction. Insoluble constituents are then filtered off via a frit, and the orange-red filtrate is evaporated to dryness on an oil pump. 30 ml of pentane are added to the orange-red residue, and the mixture is stirred vigorously overnight. Removal of the solvent in vacuo gives the hafnocene dichloride as beige powder in a crude product yield of 700 mg (24%). The $^1$H-NMR spectrum of the crude product shows only one diastereomer.

EXAMPLE 16

Synthesis of the Two Diastereomers of 4-($\eta^5$-Cyclopentadienyl)-4,7-dimethyl-7-butyl($\eta^5$-4,5,6,7-tetrahydroindenyl)dichlorotitanium Suspension of 5.95 g (16.8 mmol) of the dilithium salt (Example 4) in 120 ml of toluene and addition of 3.18 g of (16.8 mmol) of titanium tetrachloride at −78° C. causes the beige suspension immediately to change color to dark red. The suspension is stirred at room temperature for a further 36 hours, before the precipitate is separated off, and the dark red filtrate is evaporated to dryness in an oil-pump vacuum. The two diastereomers of the titanocene dichloride are obtained as a brown-red powder in a crude yield of 1.54 g (24%). The signals of the two diastereomers can be determined in the $^1$H-NMR, spectrum of the crude product in a ratio of 8:1. Extraction of the brown-red powder with pentane for several days in a circulation frit causes a brown precipitate to form from the filtrate. The $^1$H-NMR spectrum shows that the pentane solution contains the two isomers in the ratio of 1:1 (150 mg, 2.3%) while the brown powder (720 mg, 11%) is virtually diastereomerically pure.

EXAMPLE 17

Synthesis of {4-[3'-t-Bu-($\eta^5$-cyclopentadienyl)]-4,7,7,-trimethyl($\eta^5$-4,5,6,7-tetrahydroindenyl)}dichlorozirconium A suspension of 2.84 g (7.71 mmol) of the dilithium salt (Example 9) is suspended in 150 ml of toluene and cooled to −78° C. 1.79 g (7.71 mol) of zirconium tetrachloride are added to portions, and the mixture is warmed to room temperature and stirred for a further 48 hours. Insoluble constituents are subsequently separated off, the orange toluene phase is evaporated in an oil-pump vacuum, and the orange-red oil is powdered by vigorous stirring in pentane.

The regioisomeric zirconocene dichlorides are obtained as an orange-yellow powder in a crude yield of 23% (787 mg). The $^1$H-NMR spectrum of the crude product shows the signals of the two diastereomers in a ratio of 1:1. Extraction of the orange-yellow powder with pentane in a circulation frit gives 370 mg (11%) of the zirconocene dichlorides in a ratio of 1:1.

G. Synthesis of the Dialkylmetallocene Complexes

EXAMPLE 18

Synthesis of 4-($\eta^5$-Cyclopentadienyl)-4,7,7-trimethyl($\eta^5$-4,5,6,7-tetrahydroindenyl) zirconiumdimethyl Following the literature procedure [b], 3.30 ml (5.33 mmol, 1.60 M) of an ethereal solution of methyllithium are slowly added dropwise at −78° C. to a suspension of 1.03 g (2.66 mmol) of zirconocene dichloride (Example 10) in 50 ml of diethyl ether. The mixture is allowed to warm slowly to room temperature in a cold bath and is then stirred at room temperature for a further 5 hours. The solvent is removed in vacuo, and the colorless residue is extracted with 3×50 ml of pentane. The combined pentane solutions are evaporated and kept at −25° C. to crystallize. Removal of the solvent and drying in an oil-pump vacuum gives 700 mg (76%) of dimethylzirconocene as a colorless, crystalline powder.

[b] E. Samuel, M. D. Rausch, J. Am. Chem. Soc. 95 (1973) 6263.

EXAMPLE 19

Synthesis of the Two Diastereomers of [4-($\eta^5$-Cyclopentadienyl)-4,7-dimethyl-7-(2-propen-1-yl) ($\eta^5$-4,5,6,7-tetrahydroindenyl)]dichlorotitanium 2.45 g (7.24 mmol) of the dilithium compound (Example 9b) are dissolved in 80 ml of tetrahydrofuran, giving an orange, clear solution, which is subsequently cooled to −78° C., and 2.42 g (7.24 mmol) of titanium tetrachloride/bis-THF adduct are added. The reaction mixture immediately changes color to dark red. The mixture is allowed to warm to room temperature and is stirred for a further two days. Removal of the solvent in vacuo gives a brown powder. Pentane extraction of the crude product in a circulation frit gives 0.22 g (9%) of the two allyltitanocenes as a brown powder.

The $^1$H-NMR spectrum shows the two products in a diastereomer ratio of 2:1.

EXAMPLE 20

Synthesis of the Two Diastereomers of [4-($\eta^5$-Cyclopentadienyl)-4,7-dimethyl-7-(2-propen-1-yl) ($\eta^5$-4,5,6,7-tetrahydroindenyl)]dichlorozirconium 7.56 g (22.3 mmol) of the dilithium compound (Example 9b) are suspended in 200 ml of toluene and cooled to −78° C. 5.21 g (22.3 mmol) of zirconium tetrachloride are added in portions. After 30 minutes at −78° C., the mixture is allowed to warm to room temperature over the course of 4 hours and is stirred for a further 12 hours. The orange suspension is then filtered through a G4 frit, the residue is washed twice with 30 ml of toluene in each case, and the filtrate is evaporated to dryness in an oil-pump vacuum, giving an orange oil, which can be powdered by addition of 50 ml of pentane followed by vigorous stirring. Removal of the solvent in vacuo gives the yellow-orange, pulverulent allylzirconocenes in a crude yield of 5.04 g (55%). Repeated extraction of the crude product with 100 ml of pentane in a circulation frit gives 2.34 g (26%) of the allylzirconocenes as a yellow powder; m.p. 99° C. (DSC).

The $^1$H-NMR spectrum shows the two products 23a and 23b in a diastereomer rato of 1.5:1.

EXAMPLE 21

Synthesis of the two diastereomers of [4-($\eta^5$,-cyclopentadienyl)-4,7-dimethyl-7-(3-(9-borabicyclono{3,3,1}nonyl-β)propyl-($\eta^5$-4,5,6,7-tetrahydroindenyl)] dichlorozirconium 210 (0.51 mmol) of the allylzirconocene dichlorides (Example 20) are dissolved in 50 ml of toluene, and 62 mg (0.51 mmol) of 9 BBN are added at room temperature. The mixture is stirred at room temperature for 36 hours, the solvent is removed in vacuo, and the orange-yellow oil is powdered using 30 ml of diethyl ether. Evaporation of the clear solution to 10 ml and cooling for several hours at −30° C. gives 208 mg (78%) of the diastereomers as an orange-yellow powder; m.p. 74° C. (DSC).

EXAMPLE 22

Synthesis of 7-(3'-i-propylcyclopentadienyl)-4,4,7-trimethyl-4,5,6,7-tetrahydro-1H-indene a) Synthesis of {4-[3'-i-propyl-($\eta^5$-cyclopentadienyl)]-4,7,7-trimethyl($\eta^5$-4,5,6,7-tetrahydroindenyl)}dichlorozirconium A solution of 6.11 g (22.9 mmol) of the tetrahydroindenylfulvene (Example 8a) in 20 ml of diethyl ether is added dropwise at room temperature to a suspension of 2.17 g (57.3 mmol) of lithium aluminum hydride in 100 ml of diethyl ether. After a vigorous, but not very exothermic reaction, the orange suspension is refluxed for a further three hours, cooled to 0° C. in an icebath and carefully hydrolyzed by means of ice-water, giving a white, bulky precipitate, which is extracted twice with 50 ml of diethyl ether in each case, and the combined organic phases are washed with aqueous sodium chloride solution. Drying over magnesium sulfate and removal of the solvent in vacuo give 5.63 g (92%) of the i-propyl-substituted ansa-ligand as an orange oil.

The product again comprises a plurality of double-bond isomers, so that only a rough assignment of signal groups in the $^1$H-NMR spectrum is possible.

b) Synthesis of {4-[3'-i-propyl-($\eta^5$-cyclopentadienyl)]-4,7,7-trimethyl($\eta^5$-4,5,6,7-tetrahydroindenyl)}dilithium 4.21 g (15.7 mmol) of the isopropyl-substituted ligand are dissolved in 70 ml of diethyl ether, and 21.6 ml (34.5 mmol) of a 1.60 M solution of methyllithium are added dropwise at 0° C. The solution rapidly becomes colorless, and a white precipitate forms. When the dropwise addition is complete, the mixture is stirred at room temperature for a further 15 hours. The precipitate is then filtered off and washed twice with 15 ml of diethyl ether in each case, giving 5.20 g (93%) of the extremely air-sensitive dilithium salt as a beige powder containing one mole-equivalent of diethyl ether.

c) Synthesis of {4-[3'-i-propyl($\eta^5$-cyclopentadienyl)]-4,7,7-trimethyl($\eta^5$-4,5,6,7-tetrahydroindenyl)}dichlorozirconium 3.40 g (14.6 mmol) of zirconium tetrachloride are slowly added to a suspension, cooled to −78° C., of 5.20 g (14.7 mmol) of the dilithium salt in 200 ml of toluene. The resultant beige suspension is stirred at room temperature for 24 hours, before insoluble constituents are separated off and the orange, clear filtrate is evaporated to approximately 50 ml in an oil-pump vacuum. $^1$H-NMR spectroscopic analysis of the toluene phase shows that the two diastereomers are present therein in a ratio of 1:1. Addition of 20 ml of pentane and storage in the ice box at =20° C. causes precipitation of a yellow solid (1.42 g) in which one diastereomer is significantly concentrated (8:1). Accordingly, the toluene phase contains the other diastereomer concentrated in the reverse ratio (1:62 g); overall yield 49%.

Dissolution of approximately 100 g of the precipitated yellow powder in methylene chloride and slow diffusion of pentane into this solution gives crystals suitable for X-ray structure analysis, which shows that they are the diastereomer (4R*-{4-[3'-i-Pr-($\eta^5$-cyclopentadienyl)]-4,7,7-trimethyl($\eta^5$-4,5,6,7-pR*-tetrahydroindenyl)}dichlorozirconium.

EXAMPLE 23

Synthesis of {4-[3'-i-Propyl($\eta^5$-cyclopentadienyl)]-4,7,7-trimethyl[2-i-propyl($\eta^5$-4,5,6,7-tetrahydroindenyl)}dichlorozirconium a) Synthesis of 4-(3'-i-propylcyclopentadienyl)-4,7,7-trimethyl-(2-i-propyl-4,5,6,7-tetrahydro-1H-indene) starting from 2-isopropylidene-4-(3'-isopropylidenecyclopenta-1',4'-dienyl)-4,7,7,-trimethyl-(4,5,6,7-tetrahydro-2H-indene)

Dissolution of 8.32 g (34.2 mmol) of the "monofulvene" (Example 8a) in a mixture of 50 ml of methanol and 20 ml of pentane gives an orange-red, clear solution, which is cooled to 0° C. Successive addition of 2.61 g (3.31 ml, 45.0 mmol) of acetone and 6.08 g (7.10 ml, 85.5 mmol) of pyrrolidine causes the reaction solution to change color to dark red after 30 minutes. The reaction mixture is stirred at room temperature for 7 days, and 5 ml of glacial acetic acid, 150 ml of water and 50 ml of pentane are added successively. The aqueous phase is extracted by shaking twice with pentane, and the combined organic phases are washed several times with saturated, aqueous sodium chloride solution and dried over magnesium sulfate. Removal of the solvent in an oil-pump vacuum gives the difulvene as a red oil in a crude yield of 9.04 g (86%).

Some of the red oil is taken up in pentane and chromatographed on a silica gel column (Merck, 60 mesh) which has previously been deactivated by means of triethylamine. The eluent used is a pentane:diethyl ether mixture (100:5) (overall yield<10%).

b) Synthesis of 4-(3'-i-propylcyclopentadienyl)-4,7,7-trimethyl(2-i-propyl-4,5,6,7-tetrahydro-1H-indene)

3.03 g (80.0 mmol) of lithium aluminum hydride in 100 ml of diethyl ether are introduced into a three-neck flask fitted with coil condenser and dropping funnel, and 6.47 g (21.1 mmol) of the difulvene (Example 23a) dissolved in 50 ml of diethyl ether are added dropwise at room temperature with vigorous stirring. When the addition is complete, the reaction mixture is refluxed for a further 5 hours and then carefully hydrolyzed using 100 ml of water, giving a gray precipitate of aluminum oxide and a yellow diethyl ether phase. The latter is decanted off, the gray precipitate is extracted a number of times with diethyl ether, and the combined diethyl ether phases are washed with saturated, aqueous sodium chloride solution. Drying over magnesium sulfate and removal of the solvent in vacuo give 6.25 g (96%) of the reduced difulvene as an orange-red oil, which is reacted without further purification.

c) Synthesis of 4-(3'-i-propylcyclopentadienyl)-4,7,7-trimethyl(2-i-propyl-4,5,6,7-tetrahydro-1H-indene) via 2,5-bis[(i-propyl)cyclopenta-2,4-dien-1-ylidene]hexane 5.90 ml (5.07 g, 71.3 mmol) of freshly distilled pyrrolidine are added dropwise at 0° C. to a solution of 2.78 ml (2.71 g, 23.8 mmol) of 2,5-hexanedione and 4.00 g (47.6 mmol) of isopropylcyclopentadiene in 50 ml of methanol. During this addition, the reaction solution immediately changes color to dark red and is stirred at 0° C. for a further 15 hours. For work-up, the pyrrolidine is neutralized by addition of a solution of 2 ml of glacial acetic acid in 100 ml of water. The mixture is extracted twice with 100 ml of diethyl ether in each case, the combined organic phases are washed several times with saturated, aqueous sodium chloride solution and dried over magnesium sulfate. Removal of the solvent in vacuo gives the difulvene as a dark-red oil in a crude yield of 75% (5.20 g).

The difulvene is purified by column chromatography in a silica gel column, deactivated by means of triethylamine (pentane:triethylamine=100:1). A suitable eluent is a pentane:diethyl ether solvent mixture in a ratio of 1:1, allowing the isolation of 1.72 g of the difulvene (25%) as a red oil.

d) Synthesis of 4-(3'-i-propylcyclopentadienyl)-4,7,7-trimethyl(2-i-propyl-4,5,6,7-tetrahydro-1H-indene)

600 mg (2.04 mmol) of the bisisopropyl-substituted difulvene (Example 23b) are dissolved in 10 ml of diethyl ether, and 2.55 ml of an ethereal 1.60 M solution of methyllithium are slowly added at 0° C. The mixture is allowed to warm to room temperature, giving, after 24 hours, an orange suspension, which is cooled to 0° C. before it is hydrolyzed by means of 10 ml of water. Extraction with 20 ml of diethyl ether and drying over magnesium sulfate gives 520 mg of the cyclized product as an orange oil in a yield of 82%.

e) Synthesis of {4-[3'-i-propyl($\eta^5$-cyclopentadienyl)]-4,7,7-trimethyl[2-i-propyl($\eta^5$-4,5,6,7-tetrahydroindenyl)}dichlorozirconium 2.00 ml (3.22 mmol) of a 1.60 M ethereal solution of methyllithium are added dropwise at 0° C. to a solution of 500 mg (1.61 mmol) of the bisisopropyl-substituted compounds (Examples 23a and 23b) in 20 ml of pentane. The mixture is allowed to warm to room temperature, giving, after 12 hours, a cloudy, orange suspension, which is cooled to −78° C. and treated with 373 mg (1.61 mmol) of zirconium tetrachloride. After the mixture has been stirred at room temperature for 24 hours, the insoluble constituents are filtered off, and the solvent is removed in vacuo, giving the two diastereomers of the ansazirconocene as an orange powder in a crude yield of 300 mg (40%). The $^1$H-NMR spectrum shows the resonance signals of the two diastereomers in the ratio 1:1 (determined from the i-Pr groups).

EXAMPLE 24

Synthesis of {4-[3'-trimethylsilyl($\eta^5$-cyclopentadienyl)]-4,7,7-trimethyl[2-trimethylsilyl($\eta^5$-4,5,6,7-tetrahydroindenyl)]}dichlorozirconium a) Synthesis of 7-(3'-trimethylsilylcyclopentadienyl)-4,4,7-trimethyl(2-trimethylsilyl-4,5,6,7-tetrahydro-1H-indene)

A solution of 6.81 g (21.8 mmol) of the dilithium etherate (Example 2) in 50 ml of tetrahydrofuran is cooled to 0° C., and 5.50 ml (4.74 g, 43.6 mmol) of trimethylsilyl chloride are added dropwise. The mixture is allowed to warm to room temperature overnight, giving an orange, cloudy suspension, which is hydrolyzed by addition of 50 ml of degassed water and subsequently extracted with petroleum ether. Drying over magnesium sulfate and removal of the solvent in vacuo gives 6.54 g (81%) of a red-orange oil.

b) Synthesis of {4-[3'-trimethylsilyl($\eta^5$-cyclopentadienyl)]-4,7,7-trimethyl[2-trimethylsilyl($\eta^5$-4,5,6,7-tetrahydroindenyl)]}dilithium 11.1 ml (17.8 mmol) of a 1.60 M ethereal solution of methyllithium are added dropwise to a solution, cooled to 0° C., of 3.30 g (8.90 mmol) of the bistrimethylsilyl-substituted compound in 40 ml of pentane. A white precipitate is obtained and gas is evolved. The mixture is stirred at room temperature for a further 24 hours in order to complete the reaction, before the white precipitate is filtered off and washed with pentane. Drying in an oil-pump vacuum gives the dilithium salt as a white, pyrophoric residue in a yield of 76% (2.60 g).

c) Synthesis of {4-[3'-trimethylsilyl($\eta^5$-cyclopentadienyl)]-4,7,7-trimethyl[2-trimethylsilyl($\eta^5$-4,5,6,7-tetrahydroindenyl)]}dichlorozirconium 1.58 g (6.79 mmol) of zirconium tetrahydrochloride are added in portions to a suspension, cooled to −78° C., of 2.60 g (6.79 mmol) of the bistrimethylsilyl-substituted dilithium salt in 100 ml of toluene. The mixture is allowed to warm to room temperature, giving, after stirring for 24 hours, an orange suspension. Insoluble constituents are separated off, and the solvent is evaporated to dryness, giving a red oil. Addition of 20 ml of pentane followed by work-up gives the two diastereomers of the ansa-zirconocene as an orange powder in a crude yield of 1.54 g (43%); m.p. 151° C. (decomp., DSC).

Polymerization examples

Example A 600 cm$^3$ of an 85% strength by weight solution of norbornene in toluene are introduced into a 1.5 dm$^3$ autoclave which had previously been flushed thoroughly with ethene. The solution was saturated with ethene by repeatedly injecting ethene (18 bar). 5 cm$^3$ of a toluene solution of methylaluminoxane (10.1% strength by weight of methylaluminoxane solution having a molecular weight of 1300 g/mol according to cryoscopic determination) were metered in countercurrent into the reactor prepared for this way, and the mixture was stirred at 70° C. for 30 minutes. A solution of 1.0 mg of 4-($\eta^5$-cyclopentadienyl)-4,7,7-trimethyl($\eta^5$-4,5,6,7-tetrahydroindenyl)dichlorozirconium in 5 cm$^3$ of a toluene solution of methylaluminoxane were added after preactivation for 15 minutes. (In the case of molecular weight regulation using hydrogen, hydrogen can be injected at this point).

The mixture was polymerized for one hour at 70° C. with stirring (750 rpm), during which the ethene pressure was kept topped up at 18.0 bar.

When the reaction time was complete, the polymerization mixture was discharged into a vessel and immediately introduced into 5 dm$^3$ of acetone, the mixture was stirred for 10 minutes, and the precipitated product was subsequently filtered. The filter cake was washed alternately, three times each, with 10% strength hydrochloric acid and acetone and subsequently washed with water until neutral, and the residue was slurried in acetone and re-filtered. The polymer purified in this way was dried in vacuo (0.2 bar) at 80° C. for 15 hours.

Drying gave 224 g of colorless polymer which had a glass transition temperature of 179° C., a viscosity index of 52 cm$^3$/g, a yield stress of 59 MPa and an elongation at break of 3.1%. The activity A* was 80,512 g of polymer/h×mmol.

Example B (comparative example)

The procedure was as in Example A, but the metallocene compound used was isopropylidene(cyclopentadienyl)(1-indenyl)dichlorozirconium. 89 g of polymer were obtained which had a glass transition temperature of 150° C., a viscosity index of 57 cm$^3$/g, a yield stress of 61 MPa and an elongation at break of 3.3%. The activity A* was 34,000 g of polymer/h×mmol.

Example C 600 cm$^3$ of an 85% strength by weight solution of norbornene in toluene were introduced into a 1.5 dm$^3$ autoclave which had previously been thoroughly flushed with ethene. The solution was saturated with ethene by repeated injection of ethene (18 bar). 5 cm$^3$ of a toluene solution of methylaluminoxane (10.1% by weight methylaluminoxane solution having a molecular weight of 1300 g/mol, according to cryoscopic determination) were metered in countercurrent into the reactor prepared in this way, and the mixture was stirred at 80° C. for 30 minutes. A solution of 1.0 mg of 4-($\eta^5$-isopropylcyclopentadienyl)-4,7,7-trimethyl($\eta^5$-4,5,6,7-tetrahydroindenyl)dichlorozirconium in 5 cm$^3$ of a toluene solution of methylaluminoxane was added after preactivation for 15 minutes. (In the case of molecular weight regulation using hydrogen, hydrogen can be injected at this point.)

The mixture was polymerized for one hour with stirring (750 rpm), during which the ethene pressure was kept at 17.8 bar by re-injection and the temperature in the reactor was kept at 80° C.

When the reaction time was complete, the polymerization mixture was discharged into a vessel and immediately introduced into 5 dm$^3$ of acetone and stirred for 10 minutes, and the precipitated product was subsequently filtered. The filter cake was washed alternately, three times each, with 10% strength hydrochloric acid and acetone, then washed with water till neutral, and the residue was slurried in acetone and re-filtered. The polymer purified in this way was dried at 80° C. for 15 hours in vacuo (0.2 bar).

Drying gave 16.0 g of a colorless polymer which had a glass transition temperature of 145° C., a viscosity number of 156 cm$^3$/g, a yield stress of 64 MPa and an elongation at break of 3.3%. The activity A* was 68,300 g of polymer/h×mmol.

Example D 600 cm$^3$ of an 50% strength by weight solution of norbornene in toluene were introduced into a 1.5 dm$^3$ autoclave which had previously been thoroughly flushed with ethane. The solution was saturated with ethene by repeated injection of ethene (18 bar). 5 cm$^3$ of a toluene solution of methylaluminoxane (10.1% by weight methylaluminoxane solution having a molecular weight of 1300 g/mol, according to cryoscopic determination) were metered in countercurrent into the reactor prepared in this way, and the mixture was stirred at 80° C. for 30 minutes. A solution of 0.2 mg of 4-($\eta^5$-isopropylcyclopentadienyl)-4,7,7-trimethyl($\eta^5$-4,5,6,7-tetrahydroindenyl)dichlorozirconium in 5 cm$^3$ of a toluene solution of methylaluminoxane was added after preactivation for 15 minutes. (In the case of hydrogen control, hydrogen can be injected at this point.)

The mixture was polymerized for one hour with stirring (750 rpm), during which the ethene pressure was kept at 17.8 bar by re-injection and the temperature in the reaction was kept at 70° C.

When the reaction time was complete, the polymerization mixture was discharged into a vessel and immediately introduced into 5 dm$^3$ of acetone and stirred for 10 minutes, and the precipitated product was subsequently filtered. The filter cake was washed alternately, three times each, with 10% strength hydrochloric acid and acetone, then washed with water till neutral, and the residue was slurried in this way was dried at 80° C. for 15 hours in vacuo (0.2 bar).

Drying gave 98 g of a colorless polymer which had a glass transition temperature of 184° C., a viscosity number of 114 cm$^3$/g, a yield stress of 61 MPa and an elongation at break of 3.1%. The activity A* was 104,500 g of polymer/h×mmol.

Example E 600 cm$^3$ of an 50% strength by weight solution of norbornene in toluene were introduced into a 1.5 dm$^3$ autoclave which had previously been thoroughly flushed with ethene. The solution was saturated with ethene by repeated injection of ethene (18 bar). 5 cm$^3$ of a toluene solution of methylaluminoxane (10.1% by weight methylaluminoxane solution having a molecular weight of 1300 g/mol, according to cryoscopic determination) were metered in countercurrent into the reactor prepared in this way, and the mixture was stirred at 80° C. for 30 minutes. A solution of 1.0 mg of 4-($\eta^5$-isopropylcyclopentadienyl)-4,7,7-trimethyl($\eta^5$-4,5,6,7-tetrahydroindenyl)dichlorozirconium in 5 cm$^3$ of a toluene solution of methylaluminoxane was added after preactivation for 15 minutes. (In the case of hydrogen control, hydrogen can be injected at this point.)

The mixture was polymerized for one hour with stirring (750 rpm), during which the ethene pressure was kept at 17.8 bar by re-injection and the temperature in the reactor was kept at 50° C.

When the reaction time was complete, the polymerization mixture was discharged into a vessel and immediately introduced into 5 dm$^3$ of acetone and stirred for 10 minutes, and the precipitated product was subsequently filtered. The filter cake was washed alternately, three times each, with 10% strength hydrochloric acid and acetone, then washed with water till neutral, and the residue was slurried in acetone and re-filtered. The polymer purified in this way was dried at 80° C. for 15 hours in vacuo (0.2 bar).

Drying gave 31 g of a colorless polymer which had a glass transition temperature of 121° C., a viscosity number of 203 cm$^3$/g, a yield stress of 65 MPa and an elongation at break of 3.3%. The activity A* was 13,200 g of polymer/h×mmol.

Example F 600 cm$^3$ of an 50% strength by weight solution of norbornene in toluene were introduced into a 1.5 dm$^3$ autoclave which had previously been thoroughly flushed with ethene. The solution was saturated with ethene by repeated injection of ethene (18 bar). 5 cm$^3$ of a toluene solution of methylaluminoxane (10.1% by weight methylaluminoxane solution having a molecular weight of 1300 g/mol, according to cryoscopic determination) were metered in countercurrent into the reactor prepared in this way, and the mixture was stirred at 80° C. for 30 minutes. A solution of 0.83 mg of 4-($\eta^5$-isopropylcyclopentadienyl)-4,7,7-trimethyl($\eta^5$-4,5,6,7-tetrahydroindenyl)dichlorozirconium in 5 cm$^3$ of a toluene solution of methylaluminoxane was added after preactivation for 15 minutes. (In the case of hydrogen control, hydrogen can be injected at this point.)

The mixture was polymerized for one hour with stirring (750 rpm), during which the ethene pressure was kept at 18.0 bar by re-injection and the temperature in the reactor was kept at 90° C.

When the reaction time was complete, the polymerization mixture was discharged into a vessel and immediately introduced into 5 dm$^3$ of acetone and stirred for 10 minutes, and the precipitated product was subsequently filtered. The filter cake was washed alternately, three times each, with 10% strength hydrochloric acid and acetone, then washed with water till neutral, and the residue was slurried in acetone and re-filtered. The polymer purified in this way was dried at 80° C. for 15 hours in vacuo (0.2 bar).

Drying gave 45 g of a colorless polymer which had a glass transition temperature of 130° C., a viscosity number of 107 cm$^3$/g, a yield stress of 62 MPa and an elongation at break of 3.2%. The activity A* was 24,200 g of polymer/h×mmol.

Example G

The procedure was analogous to Example A, but 0.92 mg of 4-($\eta^5$-benzylcyclopentadienyl)-4,7,7-trimethyl($\eta^5$-4,5,6,7-tetrahydroindenyl)dichlorozirconium were used. The polymerization temperature was 90° C. 31 g of polymer having the following properties were obtained: Tg=141° C., VN=80 cm$^3$/g, yield stress=63 MPa, elongation at break= 3.6%, A*=18,900 g of polymer/h×mmol.

Example H

The procedure was analogous to Example A, but 1.0 mg of 4-($\eta^5$-cyclopoentadienyl)-4,7,7-trimethyl($\eta^5$-4,5,6,7-etrahydroindenyl)bis(dimethylamino)zirconium were used. 180 g of polymer having the following properties were obtained: Tg=169° C., VN=54 cm$^3$/g, yield stress=59 MPa, elongation at break=3.2%, A*=71,900 g of polymer/h× mmol.

Example I

The procedure was analogous to Example A, but 1.1 mg of 4-($\eta^5$-butylcyclopentadienyl)-4,7,7-trimethyl($\eta^5$-4,5,6,7-tetrahydroindenyl)dichlorozirconium were used. 33 g of polymer having the following properties were obtained: Tg=124° C., VN=228 cm$^3$g, yield stress=64 MPa, elongation at break=3.8%, A*=27,400 g of polymer/h×mmol.

We claim:

1. A process for the preparation of a cycloolefin copolymer by polymerization of a) at least one polycyclic olefin, b) at least one acyclic 1-olefin and c), optionally, one or more monocyclic olefins, in the presence of a catalyst comprising at least one cocatalyst and at least one stereorigid metallocene compound, where the stereorigid metallocene compound contains, as ligands, at least two substituted or unsubstituted cyclopentadienyl groups which are bonded to one another via a monocyclic or polycyclic ring system, and in which at least one cyclopentadienyl group is fused to the monocyclic or polycyclic ring system.

2. The process as claimed in claim 1, in which the monocyclic or polycyclic ring system of the stereorigid metallocene compound has at least six ring atoms.

3. The process as claimed in claim 1, in which the cocatalyst is an aluminoxane.

4. The process as claimed in claim 1, in which the stereorigid metallocene compound is a compound of the formula I

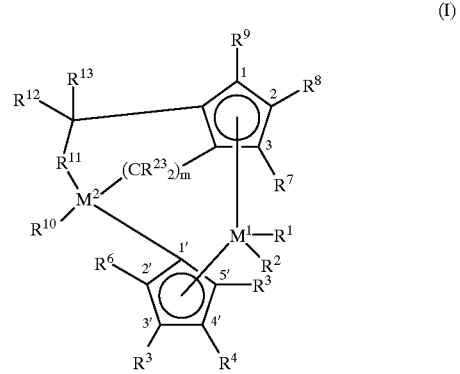

(I)

in which

M$^1$ is a metal from group IIIb, IVb, Vb or VIb of the Periodic Table,

M$^2$ is carbon, silicon, or germanium,

R$^1$ and R$^2$ are identical or different and are a hydrogen atom, a C$_1$–C$_{40}$-hydrocarbon-containing group, an OH group, a halogen tom or NR$^{14}_2$, in which R$^{14}$ is a halogen atom, a C$_1$–C$_{10}$-aryl group, or R$^1$ and R$^2$ together with the atoms connecting them form a ring system, R$^3$, R$^4$, R$^5$, R$^6$, R$^7$, R$^8$ and R$^9$ are identical or different and are a hydrogen atom, a halogen atom, a C$_1$–C$_{40}$-hydrocarbon-containing group which optionally can be halogenated, a —SiR$^{14}_3$, —NR$^{14}_2$, —SiOR$^{14}_3$, —SiSR$^{14}_3$, or —PR$^{14}_2$ radical, in which R$^{14}$ is a halogen atom, a C$_1$–C$_{10}$-alkyl group or a C$_6$–C$_{10}$-aryl group, or two or more adjacent radicals R$^3$, R$^4$, R$^5$, R$^6$, R$^7$, R$^8$ and R$^9$, together with the atoms connecting them, form a ring system, R$^{10}$ is a hydrogen atom, a C$_1$–C$_{40}$-hydrocarbon-containing group, which may carry —NR$^{14}_3$, —SiR$^{14}_3$, —SR$^{14}_2$, or —OSiR$^{14}_3$ radicals, in which R$^{14}$ is a halogen atom, a C$_1$–C$_{10}$-alkyl group or a C$_6$–C$_{10}$-aryl group, or R$^{10}$ is connected to one or more of the radicals R$^3$, R$^4$, R$^5$ and R$^6$, R$^{11}$ is

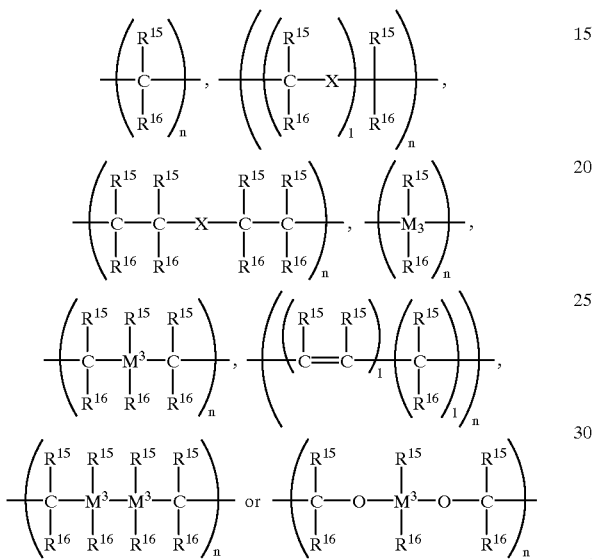

where n is an integer from 1 to 20, l is an integer from 0 to 20, X is O, =NR$^{14}$, =CO, =PR$^{14}$, =P(O)R$^{14}$, =SO, =SO$_2$ or —S—, in which R$^{14}$ is a halogen atom, a C$_1$–C$_{10}$-alkyl group or a C$_6$–C$_{10}$-aryl group, R$^{15}$ and R$^{16}$ are identical or different and are a hydrogen atom, a halogen atom or a C$_1$–C$_{40}$-hydrocarbon-containing group, or two radicals R$^{15}$, two radicals R$^{16}$ or R$^{15}$ and R$^{16}$, in each case together with the atoms connecting them, form one or more rings, and M$^{13}$ is silicon, germanium or tin, R$^{12}$ and R$^{13}$ are identical or different and are a hydrogen atom, a C$_1$–C$_{40}$-hydrocarbon-containing group, which may carry —NR$^{14}_3$, —SR$^{14}_2$, —SiR$^{14}_3$, or —OSiR$^{14}_3$ radicals, in which R$^{14}$ is a halogen atom, a C$_1$–C$_{10}$-alkyl group or a C$_6$–C$_{10}$-aryl group, or may carry halogen, R$^{23}$ is identical or different and is a hydrogen atom, a halogen atom or a C$_1$–C$_{40}$-hydrocarbon-containing group, or one or more radicals R$^{23}$ are bonded to one or both radicals R$^{15}$ and R$^{16}$ and/or to one or more radicals R$^{10}$, R$^{11}$, R$^{12}$ and R$^{13}$, and m is an integer from 0 to 24, where, in the case where M$^2$ is C,, mis 0 and R$^{11}$ is CH$_2$, at least one of the radicals R$^4$, R$^8$, R$^{10}$, R$^{12}$ and R$^{13}$ is not alkyl and/or at least on of the radicals R$^3$, R$^5$, R$^6$, R$^7$ and R$^8$ is not hydrogen.

5. The process as claimed in claim 4, in which M$^1$ is zirconium, R$^1$ and R$^2$ are identical and are a halogen atom, R$^3$, R$^4$, R$^5$, R$^6$, R$^7$, R$^8$ and R$^9$ are identical or different and are hydrogen or a C$_1$–C$_4$-alkyl group or a C$_6$–C$_{14}$-aryl group, or R$^8$ and R$^9$ and R$^3$ and R$^4$ and/or R$^5$ and R$^6$, together with the atoms connecting them, form an aromatic hydrocarbon ring system, M$^2$ is a carbon atom, R$^{10}$ is a C$_1$–C$_6$-alkyl group, R$^{11}$ is —CH$_2$—CH$_2$—, R$^{12}$ and R$^{13}$ are identical or different and are a methyl or phenyl group, and m is 0.

6. The process as claimed in claim 4, wherein R$^1$ and R$^2$ are identical or different and are C$_1$–C$_{10}$ alkyl group, a C$_1$–C$_{10}$ alkoxy group, a C$_6$–C$_{10}$-aryl group, a C$_6$–C$_{25}$-aryloxy group, a C$_2$–C$_{10}$-alkenyl group, a C$_7$–C$_{40}$-arylalkyl group or a C$_7$–C$_{40}$-arylalkenyl group;

R$^3$, R$^4$, R$^5$, R$^6$, R$^7$, R$^8$, and R$^9$ are identical or different and are a hydrogen atom, halogen atom, a C$_1$–C$_{10}$-alkyl group, which may be halogenated, a C$_6$–C$_{20}$-aryl group, a C$_6$–C$_{20}$-aryloxy group, a C$_2$–C$_{12}$-alkenyl group, a C$_7$–C$_{40}$-arylalkyl group, a C$_7$–C$_{40}$-alkylaryl group or a C$_8$–C$_{40}$-arylalkenyl group where two or more adjacent radicals are R$^3$, R$^4$, R$^5$, R$^6$, R$^7$, R$^8$ and R$^9$ together with the atoms connecting them form a ring system containing 4 to 40 carbon atoms, R$^{10}$ is a hydrogen atom, a C$_1$–C$_{20}$-alkyl group, a C$_1$–C$_{10}$-alkoxy group, a C$_6$–C$_{20}$-aryl group, a C$_6$–C$_{20}$-aryloxy group, a C$_2$–C$_{12}$-alkenyl group, a C$_7$–C$_{40}$-arylalkyl group, a C$_7$–C$_{40}$-alkylaryl group or a C$_8$–C$_{40}$-arylalkenyl group, each of which may carry —NR$^{14}_3$, SiR$^{14}_3$, —SR$^{14}_2$ or —Osir$^{14}_3$ radicals, in which R$^{14}$ is a halogen atom, a C$_1$–C$_{10}$-alkyl group or a C$_6$–C$_{10}$-aryl group R$^{15}$ and R$^6$ are identical or different and are a hydrogen atom, a halogen atom or a C$_1$–C$_{10}$-alkyl group, a C$_1$–C$_{10}$-fluoroalkyl group, a C$_1$–C$_{10}$-alkoxy group, a C$_6$–C$_{10}$-aryl group, a C$_6$–C$_{10}$-fluoroaryl group, a C$_6$–C$_{10}$-aryloxy group, a C$_2$–C$_{10}$-alkenyl group, a C$_7$–C$_{40}$-arylalkyl group, a C$_7$–C$_{40}$-alkylaryl group, or a C$_8$–C$_{40}$-arylalkenyl group, R$^{12}$ and R$^{13}$ are identical or different and a hydrogen atom C$_1$–C$_{20}$-alkyl group, a C$_1$–C$_{10}$-alkoxy group, a C$_6$–C$_{20}$-aryl group, a C$_6$–C$_{20}$-aryloxy group, a C$_2$–C$_{12}$-alkenyl group, a C$_7$–C$_{40}$-arylalkyl group, a C$_7$–C$_{40}$-alkylaryl group or a C$_8$–C$_{40}$-arylalkenyl group, each of which may carry —NR$^{14}_3$, —SR$^{14}_2$, —SiR$^{14}_3$, or —OSiR$^{14}_3$ radicals, in which R$^{14}$ is a halogen atom, a C$_1$–C$_{10}$-alkyl group or a C$_6$14 C$_{10}$-aryl group, or may carry halogen, R$^{20}_3$ is identical or different and is a hydrogen atom, a halogen atom, a C$_1$–C$_{10}$-alkyl group, a C$_1$–C$_{10}$-alkoxy group, a C$_6$–C$_{10}$-aryl group, a C$_6$–C$_{25}$-aryloxy group, a C$_2$–C$_{10}$-alkenyl group, a C$_7$–C$_{40}$-arylalkyl group or a C$_7$–C$_{40}$-arylalkenyl group.

7. The process as claimed in claim 6, wherein two or more adjacent radicals R$^3$, R$^4$, R$^5$, R$^6$, R$^7$, R$^8$ and R$^9$ together with the atoms connecting them form a ring system containing 6 to 15 carbon atoms.

8. The process as claimed in claim 6, wherein M$^1$ zirconium or hafnium and R$^1$ are identical and R$^1$–R$^3$ alkyl or a halogen atom, R$^3$, R$^4$, R$^5$, R$^6$, R$^7$, R$^8$, R$^9$ are identical or different and are a hydrogen atom or C$_1$–C$_{10}$-alkyl group, or a C$_6$–C$_{24}$-aryl group, or two or more adjacent radicals together with the atoms connecting them form an aromatic or aliphatic hydrocarbon ring system, R$^{10}$ is hydrogen, C$_6$–C$_{24}$-aryl group or a C$_1$–C$_{10}$-alkyl group, R$^{11}$ is

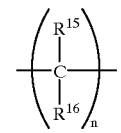

wherein n is an integer form 1 to 8, $R^{15}$ and $R^{16}$ are identical or different and are hydrogen or a $C_1$–$C_{10}$-alkyl group, or two radicals $R^{15}$, two radicals $R^{16}$ or $R^{15}$ and $R^{16}$, together with the atoms connecting them, form a hydrocarbon ring system, $M^2$ is carbon, $R^{12}$ and $R^{13}$ are identical or different and are a hydrogen atom, a $C_1$–$C_{10}$ alkyl group, or a $C_6$–$C_{10}$ aryl group and m is 0.

9. The process as claimed in claim 8, wherein $R^1$ and $R^2$ are chlorine, $M^1$ is zirconium, $R^{10}$ is $C_1$–$C_4$-alkyl group, n is an integer from 2 to 4, $R^{12}$ and $R^{13}$ are identical or different and are a hydrogen atom, a $C_1$–$C_4$-alkyl group or a $C_6$–$C_{10}$-aryl group.

10. The process as claimed in claim 9, wherein $R^3$, $R^4$, $R^5$, $R^6$, $R^7$, $R^8$ and $R^9$ are identical or different and are halogen, a $C_1$–$C_4$-alkyl group, or $C_6$–$C_{14}$-aryl group, or $R^8$ and $R^9$ and $R^3$ and $R^4$ and/or $R^5$ and $R^6$ together with the atoms connecting them from aromatic hydrocarbon ring system may be substituted, $R^{10}$ is a $C_1$–$C_6$-alkyl group, $R^{11}$ is —$CH_2$—$CH_2$, $R^{12}$ and $R^{13}$ are identical and different and are a methyl or phenyl group.

11. The process as claimed in claim 10, wherein $R^3$, $R^4$, $R^5$, $R^6$, $R^7$, $R^8$ and $R^9$ are identical or different and are hydrogen, methyl, ethyl, isopropyl, butyl or isobutyl, phenyl or naphthyl or $R^8$ and $R^9$ and $R^3$ and $R^4$ and/or $R^5$ and $R^6$ together with the atoms connecting them form a 6-membered ring, $R^{10}$ is methyl.

12. The process as claimed in claim 4, wherein at least one of the radicals $R^3$ to $R^9$ is not hydrogen.

13. The process as claimed in claim 11, wherein at least one of the radicals $R^3$ to $R^9$ is not hydrogen.

14. The process as claimed in claim 13, wherein at least one of the radicals $R^4$, $R^5$, or $R^8$ is not hydrogen.

15. The process as claimed in claim 12, wherein at least one of the radicals $R^4$, $R^5$ or $R^8$ is not hydrogen.

16. The process as claimed in claim 1, wherein the said metallocene compound is selected from the group consisting of

[4-($\eta^5$-cyclopentadienyl)-4,7,7-trimethyl ($\eta^5$-4,5,6,7-tetrahydroindenyl)]dichlorotitanium,

[4-($\eta^5$-cyclopentadienyl)-4,7,7-trimethyl ($\eta^5$-4,5,6,7-tetrahydroindenyl)]dichlorozirconium,

[4-($\eta^5$-cyclopentadienyl)-4,7,7-trimethyl ($\eta^5$-4,5,6,7-tetrahydroindenyl)]dichlorohafnium,

[4-($\eta^5$-cyclopentadienyl)-4,7,7-triphenyl ($\eta^5$-4,5,6,7-tetrahydroindenyl)]dichlorotitanium,

[4-($\eta^5$-cyclopentadienyl)-4,7,7-triphenyl ($\eta^5$-4,5,6,7-tetrahydroindenyl)]dichlorozirconium,

[4-($\eta^5$-cyclopentadienyl)-4,7-dimethyl-7-phenyl ($\eta^5$-4,5,6,7-tetrahydroindenyl)]dichlorotitanium,

[4-($\eta^5$-cyclopentadienyl)-4,7-dimethyl-7-phenyl ($\eta^5$-4,5,6,7-tetrahydroindenyl)]dichlorozirconium,

[4-($\eta^5$-cyclopentadienyl)-4,7-dimethyl-7-naphthyl ($\eta^5$-4,5,6,7-tetrahydroindenyl)]dichlorotitanium,

[4-($\eta^5$-cyclopentadienyl)-4,7-dimethyl-7-naphthyl ($\eta^5$-4,5,6,7-tetrahydroindenyl)]dichlorozirconium,

[4-($\eta^5$-cyclopentadienyl)-4,7-dimethyl-7-butyl ($\eta^5$-4,5,6,7-tetrahydroindenyl)]dichlorotitanium,

[4-($\eta^5$-cyclopentadienyl)-4,7-dimethyl-7-butyl ($\eta^5$-4,5,6,7-tetrahydroindenyl)]dichlorozirconium,

[4-($\eta^5$-3'-tert-butylcyclopentadienyl)-4,7,7-trimethyl ($\eta^5$-4,5,6,7-tetrahydroindenyl)]dichlorotitanium,

[4-($\eta^5$-3'-tert-butylcyclopentadienyl)-4,7,7-trimethyl ($\eta^5$-4,5,6,7-tetrahydroindenyl)]dichlorozirconium,

[4-($\eta^5$-3'-tert-butylcyclopentadienyl)-4,7,7-triphenyl ($\eta^5$-4,5,6,7-tetrahydroindenyl)]dichlorotitanium,

[4-($\eta^5$-3'-tert-butylcyclopentadienyl)-4,7,7-triphenyl ($\eta^5$-4,5,6,7-tetrahydroindenyl)]dichlorozirconium,

[4-($\eta^5$-3'-tert-butylcyclopentadienyl)-4,7-dimethyl-7-phenyl ($\eta^5$-4,5,6,7-tetrahydroindenyl)]dichlorotitanium,

[4-($\eta^5$-3'-tert-butylcyclopentadienyl)-4,7-dimethyl-7-phenyl ($\eta^5$-4,5,6,7-tetrahydroindenyl)]dichlorozirconium,

[4-($\eta^5$-3'-tert-butylcyclopentadienyl)-4,7-dimethyl-7-naphthyl ($\eta^5$-4,5,6,7-tetrahydroindenyl)]dichlorotitanium,

[4-($\eta^5$-3'-tert-butylcyclopentadienyl)-4,7-dimethyl-7-naphthyl ($\eta^5$-4,5,6,7-tetrahydroindenyl)]dichlorozirconium,

[4-($\eta^5$-3'-tert-butylcyclopentadienyl)-4,7-dimethyl-7-butyl ($\eta^5$-4,5,6,7-tetrahydroindenyl)]dichlorotitanium,

[4-($\eta^5$-3'-tert-butylcyclopentadienyl)-4,7-dimethyl-7-butyl ($\eta^5$-4,5,6,7-tetrahydroindenyl)]dichlorozirconium,

[4-($\eta^5$-indenyl)-4,7,7-trimethyl ($\eta^5$-4,5,6,7-tetrahydroindenyl)]dichlorotitanium,

[4-($\eta^5$-indenyl)-4,7,7-trimethyl ($\eta^5$-4,5,6,7-tetrahydroindenyl)]dichlorozirconium,

[4-($\eta^5$-indenyl)-4,7,7-triphenyl ($\eta^5$-4,5,6,7-tetrahydroindenyl)]dichlorotitanium,

[4-($\eta^5$-indenyl)-4,7,7-triphenyl ($\eta^5$-4,5,6,7-tetrahydroindenyl)]dichlorozirconium,

[4-($\eta^5$-indenyl)-4,7-dimethyl-7-phenyl ($\eta^5$-4,5,6,7-tetrahydroindenyl)]dichlorotitanium,

[4-($\eta^5$-indenyl)-4,7-dimethyl-7-phenyl ($\eta^5$-4,5,6,7-tetrahydroindenyl)]dichlorozirconium,

[4-($\eta^5$-indenyl)-4,7-dimethyl-7-naphthyl ($\eta^5$-4,5,6,7-tetrahydroindenyl)]dichlorotitanium,

[4-($\eta^5$-indenyl)-4,7-dimethyl-7-naphthyl ($\eta^5$-4,5,6,7-tetrahydroindenyl)]dichlorozirconium,

[4-($\eta^5$-indenyl)-4,7-dimethyl-7-butyl ($\eta^5$-4,5,6,7-tetrahydroindenyl)]dichlorotitanium,

[4-($\eta^5$-indenyl)-4,7-dimethyl-7-butyl ($\eta^5$-4,5,6,7-tetrahydroindenyl)]dichlorozirconium,

[4-($\eta^5$-cyclopentadienyl)-4,7,7-trimethyl ($\eta^5$-4,5,6,7-tetrahydrofluorenyl)]dichlorotitanium,

[4-($\eta^5$-cyclopentadienyl)-4,7,7-trimethyl ($\eta^5$-4,5,6,7-tetrahydrofluorenyl)]dichlorozirconium,

[4-($\eta^5$-cyclopentadienyl)-4,7,7-triphenyl ($\eta^5$-4,5,6,7-tetrahydrofluorenyl)]dichlorotitanium,

[4-($\eta^5$-cyclopentadienyl)-4,7,7-triphenyl ($\eta^5$-4,5,6,7-tetrahydrofluorenyl)]dichlorozirconium,

[4-($\eta^5$-cyclopentadienyl)-4,7-dimethyl-7-phenyl ($\eta^5$-4,5,6,7-tetrahydrofluorenyl)]dichlorotitanium,

[4-($\eta^5$-cyclopentadienyl)-4,7-dimethyl-7-phenyl ($\eta^5$-4,5,6,7-tetrahydrofluorenyl)]dichlorozirconium,

[4-($\eta^5$-cyclopentadienyl)-4,7-dimethyl-7-naphthyl ($\eta^5$-4,5,6,7-tetrahydrofluorenyl)]dichlorotitanium,

[4-($\eta^5$-cyclopentadienyl)-4,7-dimethyl-7-naphthyl-($\eta^5$-4,5,6,7-tetrahydrofluorenyl)]dichlorozirconium,

[4-($\eta^5$-cyclopentadienyl)-4,7-dimethyl-7-butyl ($\eta^5$-4,5,6,7-tetrahydrofluorenyl)]dichlorotitanium,

[4-($\eta^5$-cyclopentadienyl)-4,7-dimethyl-7-butyl ($\eta^5$-4,5,6,7-tetrahydrofluorenyl)]dichlorozirconium,

[4-($\eta^5$-3'-methylcyclopentadienyl)-4,7,7-trimethyl-($\eta^5$-4,5,6,7-tetrahydroindenyl)]dichlorotitanium,

[4-($\eta^5$-3'-methylcyclopentadienyl)-4,7,7-trimethyl-($\eta^5$-4,5,6,7-tetrahydroindenyl)]dichlorozirconium,

[4-(η⁵-3'-methylcyclopentadienyl)-4,7,7-triphenyl-(η⁵-4,5,6,7-tetrahydroindenyl)]dichlorotitanium,
[4-(η⁵-3'-methylcyclopentadienyl)-4,7,7-triphenyl-(η⁵-4,5,6,7-tetrahydroindenyl)]dichlorozirconium,
[4-(η⁵-3'-methylcyclopentadienyl)-4,7-dimethyl-7-phenyl-(η⁵-4,5,6,7-tetrahydroindenyl)]dichlorotitanium,
[4-(η⁵-3'-methylcyclopentadienyl)-4,7-dimethyl-7-phenyl-(η⁵-4,5,6,7-tetrahydroindenyl)]dichlorozirconium,
[4-(η⁵-3'-methylcyclopentadienyl)-4,7-dimethyl-7-naphthyl-(η⁵-4,5,6,7-tetrahydroindenyl)]dichlorotitanium,
[4-(η⁵-3'-methylcyclopentadienyl)-4,7-dimethyl-7-naphthyl-(η⁵-4,5,6,7-tetrahydroindenyl)]dichlorozirconium,
[4-(η⁵-3'-methylcyclopentadienyl)-4,7-dimethyl-7-butyl-(η⁵-4,5,6,7-tetrahydroindenyl)]dichlorotitanium,
[4-(η⁵-3'-methylcyclopentadienyl)-4,7-dimethyl-7-butyl-(η⁵-4,5,6,7-tetrahydroindenyl)]dichlorozirconium,
[4-(η⁵-cyclopentadienyl)-4,7,7-trimethyl (η⁵-2-methyl-4,5,6,7-tetrahydroindenyl)]dichlorotitanium,
[4-(η⁵-cyclopentadienyl)-4,7,7-trimethyl (η⁵-2-methyl-4,5,6,7-tetrahydroindenyl)]dichlorozirconium,
[4-(η⁵-cyclopentadienyl)-4,7,7-triphenyl (η⁵-2-methyl-4,5,6,7-tetrahydroindenyl)]dichlorotitanium,
[4-(η⁵-cyclopentadienyl)-4,7,7-triphenyl (η⁵-2-methyl-4,5,6,7-tetrahydroindenyl)]dichlorozirconium,
[4-(η⁵-cyclopentadienyl)-4,7-dimethyl-7-phenyl (η⁵-2-methyl-4,5,6,7-tetrahydroindenyl)]dichlorotitanium,
[4-(η⁵-cyclopentadienyl)-4,7-dimethyl-7-phenyl (η⁵-2-methyl-4,5,6,7-tetrahydroindenyl)]dichlorozirconium,
[4-(η⁵-cyclopentadienyl)-4,7-dimethyl-7-naphthyl (η⁵-2-methyl-4,5,6,7-tetrahydroindenyl)]dichlorotitanium,
[4-(η⁵-cyclopentadienyl)-4,7-dimethyl-7-naphthyl (η⁵-2-methyl-4,5,6,7-tetrahydroindenyl)]dichlorozirconium,
[4-(η⁵-cyclopentadienyl)-4,7-dimethyl-7-butyl (η⁵-2-methyl-4,5,6,7-tetrahydroindenyl)]dichlorotitanium,
[4-(η⁵-cyclopentadienyl)-4,7-dimethyl-7-butyl (η⁵-2-methyl-4,5,6,7-tetrahydroindenyl)]dichlorozirconium,
[4-(η⁵-3'-methylcyclopentadienyl)-4,7,7-trimethyl (η⁵-2-methyl-4,5,6,7-tetrahydroindenyl)]dichlorotitanium,
[4-(η⁵-3'-methylcyclopentadienyl)-4,7,7-trimethyl (η⁵-2-methyl-4,5,6,7-tetrahydroindenyl)]dichlorozirconium,
[4-(η⁵-3'-methylcyclopentadienyl)-4,7,7-triphenyl (η⁵-2-methyl-4,5,6,7-tetrahydroindenyl)]dichlorotitanium,
[4-(η⁵-3'-methylcyclopentadienyl)-4,7,7-triphenyl (η⁵-2-methyl-4,5,6,7-tetrahydroindenyl)]dichlorozirconium,
[4-(η⁵-3'-methylcyclopentadienyl)-4,7-dimethyl-7-phenyl (η⁵-2-methyl-4,5,6,7-tetrahydroindenyl)]dichlorotitanium,
[4-(η⁵-3'-methylcyclopentadienyl)-4,7-dimethyl-7-phenyl (η⁵-2-methyl-4,5,6,7-tetrahydroindenyl)]dichlorozirconium,
[4-(η⁵-3'-methylcyclopentadienyl)-4,7-dimethyl-7-naphthyl (η⁵-2-methyl-4,5,6,7-tetrahydroindenyl)]dichlorotitanium,
[4-(η⁵-3'-methylcyclopentadienyl)-4,7-dimethyl-7-naphthyl (η⁵-2-methyl-4,5,6,7-tetrahydroindenyl)]dichlorozirconium,
[4-(η⁵-3'-methylcyclopentadienyl)-4,7-dimethyl-7-butyl (η⁵-2-methyl-4,5,6,7-tetrahydroindenyl)]dichlorotitanium,
[4-(η⁵-3'-methylcyclopentadienyl)-4,7-dimethyl-7-butyl (η⁵-2-methyl-4,5,6,7-tetrahydroindenyl)]dichlorozirconium,
[4-(η⁵-fluorenyl)-4,7,7-trimethyl (η⁵-4,5,6,7-tetrahydroindenyl)]dichlorotitanium,
[4-(η⁵-fluorenyl)-4,7,7-trimethyl (η⁵-4,5,6,7-tetrahydroindenyl)]dichlorozirconium,
[4-(η⁵-fluorenyl)-4,7,7-triphenyl (η⁵-4,5,6,7-tetrahydroindenyl)]dichlorotitanium,
[4-(η⁵-fluorenyl)-4,7,7-triphenyl (η⁵-4,5,6,7-tetrahydroindenyl)]dichlorozirconium,
[4-(η⁵-fluorenyl)-4,7-dimethyl-7-phenyl (η⁵-4,5,6,7-tetrahydroindenyl)]dichlorotitanium,
[4-(η⁵-fluorenyl)-4,7-dimethyl-7-phenyl (η⁵-4,5,6,7-tetrahydroindenyl)]dichlorozirconium,
[4-(η⁵-fluorenyl)-4,7-dimethyl-7-naphthyl (η⁵-4,5,6,7-tetrahydroindenyl)]dichlorotitanium,
[4-(η⁵-fluorenyl)-4,7-dimethyl-7-naphthyl (η⁵-4,5,6,7-tetrahydroindenyl)]dichlorozirconium,
[4-(η⁵-fluorenyl)-4,7-dimethyl-7-butyl (η⁵-4,5,6,7-tetrahydroindenyl)]dichlorotitanium,
[4-(η⁵-fluorenyl)-4,7-dimethyl-7-butyl (η⁵-4,5,6,7-tetrahydroindenyl)]dichlorozirconium,
[4-(η⁵-cyclopentadienyl)-4,7,7-trimethyl-4,5,6,7,10,11,12,13-octahydro-5,6-benzoindenyl)dichlorozirconium,
[5-(η⁵-cyclopentadienyl)-4,7,7-trimethyl (η⁵-4,5,6,7-tetrahydroindenyl)]dichlorotitanium,
[5-(η⁵-cyclopentadienyl)-4,7,7-trimethyl (η⁵-4,5,6,7-tetrahydroindenyl)]dichlorozirconium,
[5-(η⁵-cyclopentadienyl)-4,7,7-triphenyl (η⁵-4,5,6,7-tetrahydroindenyl)]dichlorotitanium,
[5-(η⁵-cyclopentadienyl)-4,7,7-triphenyl (η⁵-4,5,6,7-tetrahydroindenyl)]dichlorozirconium,
[5-(η⁵-cyclopentadienyl)-4,7-dimethyl-7-phenyl (η⁵-4,5,6,7-tetrahydroindenyl)]dichlorotitanium,
[5-(η⁵-cyclopentadienyl)-4,7-dimethyl-7-phenyl (η⁵-4,5,6,7-tetrahydroindenyl)]dichlorozirconium,
[5-(η⁵-cyclopentadienyl)-4,7-dimethyl-7-naphthyl (η⁵-4,5,6,7-tetrahydroindenyl)]dichlorotitanium,
[5-(η⁵-cyclopentadienyl)-4,7-dimethyl-7-naphthyl (η⁵-4,5,6,7-tetrahydroindenyl)]dichlorozirconium,
[5-(η⁵-cyclopentadienyl)-4,7-dimethyl-7-butyl (η⁵-4,5,6,7-tetrahydroindenyl)]dichlorotitanium,
[5-(η⁵-cyclopentadienyl)-4,7-dimethyl-7-butyl (η⁵-4,5,6,7-tetrahydroindenyl)]dichlorozirconium,
[5-(η⁵-3'-tert-butylcyclopentadienyl)-4,7,7-trimethyl (η⁵-4,5,6,7-tetrahydroindenyl)]dichlorotitanium,
[5-(η⁵-3'-tert-butylcyclopentadienyl)-4,7,7-trimethyl (η⁵-4,5,6,7-tetrahydroindenyl)]dichlorozirconium,
[5-(η⁵-3'-tert-butylcyclopentadienyl)-4,7,7-triphenyl (η⁵-4,5,6,7-tetrahydroindenyl)]dichlorotitanium,
[5-(η⁵-3'-tert-butylcyclopentadienyl)-4,7,7-triphenyl (η⁵-4,5,6,7-tetrahydroindenyl)]dichlorozirconium,
[5-(η⁵-3'-tert-butylcyclopentadienyl)-4,7-dimethyl-7-phenyl (η⁵-4,5,6,7-tetrahydroindenyl)]dichlorotitanium,
[5-(η⁵-3'-tert-butylcyclopentadienyl)-4,7-dimethyl-7-phenyl (η⁵-4,5,6,7-tetrahydroindenyl)]dichlorozirconium,
[5-(η⁵-3'-tert-butylcyclopentadienyl)-4,7-dimethyl-7-naphthyl (η⁵-4,5,6,7-tetrahydroindenyl)]dichlorotitanium,

[5-($\eta^5$-3'-tert-butylcyclopentadienyl)-4,7-dimethyl-7-naphthyl ($\eta^5$-4,5,6,7-tetrahydroindenyl)]dichlorozirconium,

[5-($\eta^5$-3'-tert-butylcyclopentadienyl)-4,7-dimethyl-7-butyl ($\eta^5$-4,5,6,7-tetrahydroindenyl)]dichlorotitanium,

[5-($\eta^5$-3'-tert-butylcyclopentadienyl)-4,7-dimethyl-7-butyl ($\eta^5$-4,5,6,7-tetrahydroindenyl)]dichlorozirconium,

[5-($\eta^5$-indenyl)-4,7,7-trimethyl-($\eta^5$-4,5,6,7-tetrahydroindenyl)]dichlorotitanium,

[5-($\eta^5$-indenyl)-4,7,7-trimethyl($\eta^5$-4,5,6,7-tetrahydroindenyl)]dichlorozirconium,

[5-($\eta^5$-indenyl)-4,7,7-triphenyl ($\eta^5$-4,5,6,7-tetrahydroindenyl)]dichlorotitanium,

[5-($\eta^5$-indenyl)-4,7,7-triphenyl ($\eta^5$-4,5,6,7-tetrahydroindenyl)]dichlorozirconium,

[5-($\eta^5$-indenyl)-4,7-dimethyl-7-phenyl ($\eta^5$-4,5,6,7-tetrahydroindenyl)]dichlorotitanium,

[5-($\eta^5$-indenyl)-4,7-dimethyl-7-phenyl ($\eta^5$-4,5,6,7-tetrahydroindenyl)]dichlorozirconium,

[5-($\eta^5$-indenyl)-4,7-dimethyl-7-naphthyl ($\eta^5$-4,5,6,7-tetrahydroindenyl)]dichlorotitanium,

[5-($\eta^5$-indenyl)-4,7-dimethyl-7-naphthyl ($\eta^5$-4,5,6,7-tetrahydroindenyl)]dichlorozirconium,

[5-($\eta^5$-indenyl)-4,7-dimethyl-7-butyl ($\eta^5$-4,5,6,7-tetrahydroindenyl)]dichlorotitanium,

[5-($\eta^5$-indenyl)-4,7-dimethyl-7-butyl ($\eta^5$-4,5,6,7-tetrahydroindenyl)]dichlorozirconium,

[5-($\eta^5$-cyclopentadienyl)-4,7,7-trimethyl ($\eta^5$-4,5,6,7-tetrahydrofluorenyl)]dichlorotitanium,

[5-($\eta^5$-cyclopentadienyl)-4,7,7-trimethyl ($\eta^5$-4,5,6,7-tetrahydrofluorenyl)]dichlorozirconium,

[5-($\eta^5$-cyclopentadienyl)-4,7,7-triphenyl ($\eta^5$-4,5,6,7-tetrahydrofluorenyl)]dichlorotitanium,

[5-($\eta^5$-cyclopentadienyl)-4,7,7-triphenyl ($\eta^5$-4,5,6,7-tetrahydrofluorenyl)]dichlorozirconium,

[5-($\eta^5$-cyclopentadienyl)-4,7-dimethyl-7-phenyl ($\eta^5$-4,5,6,7-tetrahydrofluorenyl)]dichlorotitanium,

[5-($\eta^5$-cyclopentadienyl)-4,7-dimethyl-7-phenyl ($\eta^5$-4,5,6,7-tetrahydrofluorenyl)]dichlorozirconium,

[5-($\eta^5$-cyclopentadienyl)-4,7-dimethyl-7-naphthyl ($\eta^5$-4,5,6,7-tetrahydrofluorenyl)]dichlorotitanium,

[5-($\eta^5$-cyclopentadienyl)-4,7-dimethyl-7-naphthyl ($\eta^5$-4,5,6,7-tetrahydrofluorenyl)]dichlorozirconium,

[5-($\eta^5$-cyclopentadienyl)-4,7-dimethyl-7-butyl ($\eta^5$-4,5,6,7-tetrahydrofluorenyl)]dichlorotitanium,

[5-($\eta^5$-cyclopentadienyl)-4,7-dimethyl-7-butyl ($\eta^5$-4,5,6,7-tetrahydrofluorenyl)]dichlorozirconium,

[5-($\eta^5$-fluorenyl)-4,7,7-trimethyl ($\eta^5$-4,5,6,7-tetrahydroindenyl)]dichlorotitanium,

[5-($\eta^5$-fluorenyl)-4,7,7-trimethyl ($\eta^5$-4,5,6,7-tetrahydroindenyl)]dichlorozirconium,

[5-($\eta^5$-fluorenyl)-4,7,7-triphenyl ($\eta^5$-4,5,6,7-tetrahydroindenyl)]dichlorotitanium,

[5-($\eta^5$-fluorenyl)-4,7,7-triphenyl ($\eta^5$-4,5,6,7-tetrahydroindenyl)]dichlorozirconium,

[5-($\eta^5$-fluorenyl)-4,7-dimethyl-7-phenyl ($\eta^5$-4,5,6,7-tetrahydroindenyl)]dichlorotitanium,

[5-($\eta^5$-fluorenyl)-4,7-dimethyl-7-phenyl ($\eta^5$-4,5,6,7-tetrahydroindenyl)]dichlorozirconium,

[4-($\eta^5$-3'-isopropylcyclopentadienyl)-4,7,7-trimethyl-$\eta^5$-4,5,6,7-tetrahydroindenyl)]dichlorozirconium,

[4-($\eta^5$-4'-isopropylcyclopentadienyl)-4,7,7-trimethyl-$\eta^5$-4,5,6,7-tetrahydroindenyl)]dichlorozirconium,

[4-($\eta^5$-3'-isopropylcyclopentadienyl)-2-isopropyl-4,7,7-trimethyl-$\eta^5$-4,5,6,7-tetrahydroindenyl)]dichlorozirconium,

[4-($\eta^5$-4'-isopropylcyclopentadienyl)-2-isopropyl-4,7,7-trimethyl-$\eta^5$-4,5,6,7-tetrahydroindenyl)]dichlorozirconium,

[4-($\eta^5$-3'-isopropylcyclopentadienyl)-4,7-dimethyl-7-phenyl-$\eta^5$-4,5,6,7-tetrahydroindenyl)]dichlorozirconium,

[4-($\eta^5$-4'-isopropyl-cyclopentadienyl)-4,7-dimethyl-7-phenyl-$\eta^5$-4,5,6,7-tetrahydroindenyl)]dichlorozirconium,

[4-($\eta^5$-3'-isopropylcyclopentadienyl)-2-isopropyl-4,7-dimethyl-7-phenyl-$\eta^5$-4,5,6,7-tetrahydroindenyl)]dichlorozirconium,

[4-($\eta^5$-4'-isopropylcyclopentadienyl)-2-isopropyl-4,7-dimethyl-7-phenyl-$\eta^5$-4,5,6,7-tetrahydroindenyl)]dichlorozirconium,

[4-($\eta^5$-3'-trimethylsilylcyclopentadienyl)-4,7,7-trimethyl-$\eta^5$-4,5,6,7-tetrahydroindenyl)]dichlorozirconium,

[4-($\eta^5$-4'-trimethylsilylcyclopentadienyl)-4,7,7-trimethyl-$\eta^5$-4,5,6,7-tetrahydroindenyl)]dichlorozirconium,

[4-($\eta^5$-3'-trimethylsilylcyclopentadienyl)-2-trimethylsilyl-4,7,7-trimethyl-$\eta^5$-4,5,6,7-tetrahydroindenyl)]dichlorozirconium,

[4-($\eta^5$-4'-trimethylsilylcyclopentadienyl)-2-trimethylsilyl-4,7,7-trimethyl-$\eta^5$-4,5,6,7-tetrahydroindenyl)]dichlorozirconium,

[4-($\eta^5$-3'-(tert-butyldimethylsilyl)cyclopentadienyl)-4,7,7-trimethyl-$\eta^5$-4,5,6,7-tetrahydroindenyl)]dichlorozirconium,

[4-($\eta^5$-4'-(tert-butyldimethylsilyl)cyclopentadienyl)-4,7,7-trimethyl-$\eta^5$-4,5,6,7-tetrahydroindenyl)]dichlorozirconium,

[4-($\eta^5$-3'-(tert-butyldimethylsilyl)cyclopentadienyl)-2-(tert-butyldimethylsilyl)-4,7,7-trimethyl-$\eta^5$-4,5,6,7-tetrahydroindenyl)]dichlorozirconium,

[4-($\eta^5$-4'-(tert-butyldimethylsilyl)cyclopentadienyl)-2-(tert-butyldimethylsilyl)-4,7,7-trimethyl-$\eta^5$-4,5,6,7-tetrahydroindenyl)]dichlorozirconium,

[4-($\eta^5$-3'-trimethylsilylcyclopentadienyl)-4,7-dimethyl-7-phenyl-$\eta^5$-4,5,6,7-tetrahydroindenyl)]dichlorozirconium,

[4-($\eta^5$-4'-trimethylsilylcyclopentadienyl)-4,7-dimethyl-7-phenyl-$\eta^5$-4,5,6,7-tetrahydroindenyl)]dichlorozirconium,

[4-($\eta^5$-3'-trimethylsilylcyclopentadienyl)-2-trimethylsilyl-4,7-dimethyl-7-phenyl-$\eta^5$-4,5,6,7-tetrahydroindenyl)]dichlorozirconium,

[4-($\eta^5$-4'-trimethylsilylcyclopentadienyl)-2-trimethylsilyl-4,7-dimethyl-7-phenyl-$\eta^5$-4,5,6,7-tetrahydroindenyl)]dichlorozirconium,

[4-($\eta^5$-3'-phenylcyclopentadienyl)-4,7,7-trimethyl-$\eta^5$-4,5,6,7-tetrahydroindenyl)]dichlorozirconium,

[4-($\eta^5$-4'-phenylcyclopentadienyl)-4,7,7-trimethyl-$\eta^5$-4,5,6,7-tetrahydroindenyl)]dichlorozirconium,

[4-($\eta^5$-3'-phenylcyclopentadienyl)-2-phenyl-4,7,7-trimethyl-$\eta^5$-4,5,6,7-tetrahydroindenyl)]dichlorozirconium,

[4-($\eta^5$-4'-phenylcyclopentadienyl)-2-phenyl-4,7,7-trimethyl-$\eta^5$-4,5,6,7-tetrahydroindenyl)]dichlorozirconium,

[4-($\eta^5$-3'-phenylcyclopentadienyl)-4,7-dimethyl-7-phenyl-$\eta^5$-4,5,6,7-tetrahydroindenyl)]dichlorozirconium,

[4-($\eta^5$-4'-phenylcyclopentadienyl)-4,7-dimethyl-7-phenyl-$\eta^5$-4,5,6,7-tetrahydroindenyl)]dichlorozirconium,

[4-($\eta^5$-3'-phenylcyclopentadienyl)-2-phenyl-4,7-dimethyl-7-phenyl-$\eta^5$-4,5,6,7-tetrahydroindenyl)]dichlorozirconium,

[4-($\eta^5$-4'-phenylcyclopentadienyl)-2-phenyl-4,7-dimethyl-7-phenyl-$\eta^5$-4,5,6,7-tetrahydroindenyl)]dichlorozirconium,

[4-($\eta^5$-4'-methylcyclopentadienyl)-4,7,7-trimethyl-$\eta^5$-4,5,6,7-tetrahydroindenyl)]dichlorozirconium,

[4-($\eta^5$-4'-methylcyclopentadienyl)-2-methyl-4,7,7-trimethyl-$\eta^5$-4,5,6,7-tetrahydroindenyl)]dichlorozirconium,

[4-($\eta^5$-4'-methylcyclopentadienyl)-2-methyl-4,7-dimethyl-7-phenyl-$\eta^5$-4,5,6,7-tetrahydroindenyl)]dichlorozirconium,

[4-($\eta^5$-4'-tert-butylcyclopentadienyl)-2-tert-butyl-4,7,7-trimethyl-$\eta^5$-4,5,6,7-tetrahydroindenyl)]dichlorozirconium,

[4-($\eta^5$-3'-tert-butylcyclopentadienyl)-2-tert-butyl-4,7,7-trimethyl-$\eta^5$-4,5,6,7-tetrahydroindenyl)]dichlorozirconium,

[4-($\eta^5$-4'-tert-butylcyclopentadienyl)-4,7,7-trimethyl-$\eta^5$-4,5,6,7-tetrahydroindenyl)]dichlorozirconium,

[4-($\eta^5$-3'-benzylcyclopentadienyl)-4,7,7-trimethyl-$\eta^5$-4,5,6,7-tetrahydroindenyl)]dichlorozirconium,

[4-($\eta^5$-4'-benzylcyclopentadienyl)-4,7,7-trimethyl-$\eta^5$-4,5,6,7-tetrahydroindenyl)]dichlorozirconium,

[4-($\eta^5$-3'-benzylcyclopentadienyl)-2-benzyl-4,7,7-trimethyl-$\eta^5$-4,5,6,7-tetrahydroindenyl)]dichlorozirconium,

[4-($\eta^5$-4'-benzylcyclopentadienyl)-2-benzyl-4,7,7-trimethyl-$\eta^5$-4,5,6,7-tetrahydroindenyl)]dichlorozirconium,

[4-($\eta^5$-cyclopentadienyl)-4-butyl-7,7-dimethyl-$\eta^5$-4,5,6,7-tetrahydroindenyl)]dichlorozirconium,

[4-($\eta^5$-cyclopentadienyl)-4-butyl-7-methyl-7-butyl-$\eta^5$-4,5,6,7-tetrahydroindenyl)]dichlorozirconium,

[4-($\eta^5$-cyclopentadienyl)-4-methyl-7,7-dibutyl-$\eta^5$-4,5,6,7-tetrahydroindenyl)]dichlorozirconium,

[4-($\eta^5$-cyclopentadienyl)-4-methyl-7-butyl-7-phenyl-$\eta^5$-4,5,6,7-tetrahydroindenyl)]dichlorozirconium,

[4-($\eta^5$-cyclopentadienyl)-4-butyl-7-methyl-7-phenyl-$\eta^5$-4,5,6,7-tetrahydroindenyl)]dichlorozirconium,

[4-($\eta^5$-3'-isopropylcyclopentadienyl)-2-isopropyl-4-butyl-7,7-dimethyl-$\eta^5$-4,5,6,7-tetrahydroindenyl)]dichlorozirconium,

[4-($\eta^5$-4'-isopropylcyclopentadienyl)-2-isopropyl-4-butyl-7,7-dimethyl-$\eta^5$-4,5,6,7-tetrahydroindenyl)]dichlorozirconium,

[4-($\eta^5$-3'-isopropylcyclopentadienyl)-2-isopropyl-4-butyl-7-butyl-7-methyl-$\eta^5$-4,5,6,7-tetrahydroindenyl)]dichlorozirconium,

[4-($\eta^5$-4'-isopropylcyclopentadienyl)-2-isopropyl-4-butyl-7-methyl-7-phenyl-$\eta^5$-4,5,6,7-tetrahydroindenyl)]dichlorozirconium,

[4-($\eta^5$-3'-isopropylcyclopentadienyl)-4-butyl-7-butyl-7-methyl-$\eta^5$-4,5,6,7-tetrahydroindenyl)]dichlorozirconium,

[4-($\eta^5$-4'-isopropylcyclopentadienyl)-2-isopropyl-4-butyl-7-methyl-7-phenyl-$\eta^5$-4,5,6,7-tetrahydroindenyl)]dichlorozirconium,

[4-($\eta^5$-cyclopentadienyl)-4,7-dimethyl-7-(2-propen-1-yl)-($\eta^5$-4,5,6,7-tetrahydroindenyl)]dichlorozirconium,

[4-($\eta^5$-3'-isopropylcyclopentadienyl)-4,7-dimethyl-7-(2-propen-1-yl)-($\eta^5$-4,5,6,7-tetrahydroindenyl)]dichlorozirconium,

[4-($\eta^5$-cyclopentadienyl)-4,7-dimethyl-7-(3-(9-borabicyclo{3,3,1}nonyl-β)propyl)-($\eta^5$-4,5,6,7-tetrahydroindenyl)]dichlorozirconium,

[4-($\eta^5$-3'-isopropylcyclopentadienyl)-4,7-dimethyl-7-(3-(9-borabicyclo{3,3,1}nonyl-β)propyl)-($\eta^5$-4,5,6,7-tetrahydroindenyl)]dichlorozirconium,

[4-($\eta^5$-4'-isopropylcyclopentadienyl)-4,7-dimethyl-7-(3-(9-borabicyclo{3,3,1}nonyl-β)propyl)-($\eta^5$-4,5,6,7-tetrahydroindenyl)]dichlorozirconium,

[4-($\eta^5$-3'-tert-butylcyclopentadienyl)-4,7-dimethyl-7-(3-(9-borabicyclo{3,3,1}nonyl-β)propyl)-($\eta^5$-4,5,6,7-tetrahydroindenyl)]dichlorozirconium,

[4-($\eta^5$-4'-tert-butylcyclopentadienyl)-4,7-dimethyl-7-(3-(9-borabicyclo{3,3,1}nonyl-β)propyl)-($\eta^5$-4,5,6,7-tetrahydroindenyl)]dichlorozirconium,

[4-($\eta^5$-3'-methylcyclopentadienyl)-4,7-dimethyl-7-(3-(9-borabicyclo{3,3,1}nonyl-β)propyl)-($\eta^5$-4,5,6,7-tetrahydroindenyl)]dichlorozirconium,

[4-($\eta^5$-3'-isopropylcyclopentadienyl)-2-isopropyl-4,7-dimethyl-7-(3-(9-borabicyclo{3,3,1}nonyl-β)propyl)-($\eta^5$-4,5,6,7-tetrahydroindenyl)]dichlorozirconium,

[4-($\eta^5$-4'-isopropylcyclopentadienyl)-2-isopropyl-4,7-dimethyl-7-(3-(9-borabicyclo{3,3,1}nonyl-β)propyl)-($\eta^5$-4,5,6,7-tetrahydroindenyl)]dichlorozirconium,

[4-($\eta^5$-3'-ethylcyclopentadienyl)-4,7,7-trimethyl-($\eta^5$-4,5,6,7-tetrahydroindenyl)]dichlorozirconium,

[4-($\eta^5$-4'-ethylcyclopentadienyl)-4,7,7-trimethyl-($\eta^5$-4,5,6,7-tetrahydroindenyl)]dichlorozirconium,

[4-($\eta^5$-3'-ethylcyclopentadienyl)-2-ethyl-4,7,7-trimethyl-($\eta^5$-4,5,6,7-tetrahydroindenyl)]dichlorozirconium,

[4-($\eta^5$-4'-ethylcyclopentadienyl)-2-ethyl-4,7,7-trimethyl-($\eta^5$-4,5,6,7-tetrahydroindenyl)]dichlorozirconium,

[4-($\eta^5$-3'-isopropylcyclopentadienyl)-2-phenyl-4,7,7-trimethyl-($\eta^5$-4,5,6,7-tetrahydroindenyl)]dichlorozirconium,

[4-($\eta^5$-4'-isopropylcyclopentadienyl)-2-phenyl-4,7,7-trimethyl-($\eta^5$-4,5,6,7-tetrahydroindenyl)]dichlorozirconium,

[4-($\eta^5$-3'-isopropylcyclopentadienyl)-2-methyl-4,7,7-trimethyl-($\eta^5$-4,5,6,7-tetrahydroindenyl)]dichlorozirconium,

[4-($\eta^5$-4'-isopropylcyclopentadienyl)-2-methyl-4,7,7-trimethyl-($\eta^5$-4,5,6,7-tetrahydroindenyl)]dichlorozirconium,

[4-($\eta^5$-3'-isopropylcyclopentadienyl)-2-phenyl-4,7,7-trimethyl-($\eta^5$-4,5,6,7-tetrahydroindenyl)]dichlorozirconium,

[4-($\eta^5$-4'-isopropylcyclopentadienyl)-2-phenyl-4,7,7-trimethyl-$\eta^5$-4,5,6,7-tetrahydroindenyl)]dichlorozirconium,

[4-($\eta^5$-2-indenyl)-4,7,7-trimethyl-$\eta^5$-4,5,6,7-tetrahydroindenyl)]dichlorozirconium,

[4-($\eta^5$-2-(4,5,6,7-tetrahydro)indenyl)-4,7,7-trimethyl-$\eta^5$-4,5,6,7-tetrahydroindenyl)]dichlorozirconium,

[4-($\eta^5$-2-indenyl)-2-methyl-4,7,7-trimethyl-$\eta^5$-4,5,6,7-tetrahydroindenyl)]dichlorozirconium,

[4-($\eta^5$-2-4,5,6,7-tetrahydro)indenyl)-4,7,7-trimethyl-$\eta^5$-4,5,6,7-tetrahydroindenyl)]dichlorozirconium,

[4-($\eta^5$-2-indenyl)-2-phenyl-4,7,7-trimethyl-$\eta^5$-4,5,6,7-tetrahydroindenyl)]dichlorozirconium,

[4-($\eta^5$-2-(4,5,6,7-tetrahydro)indenyl)-2-butyl-4,7,7-trimethyl-$\eta^5$-4,5,6,7-tetrahydroindenyl)]dichlorozirconium,

[4-($\eta^5$-2-indenyl)-2-trimethylsilyl-4,7,7-trimethyl-$\eta^5$-4,5,6,7-tetrahydroindenyl)]dichlorozirconium,

[4-($\eta^5$-2-(4,5,6,7-tetrahydro)indenyl)-2-trimethylsilyl-4,7,7-trimethyl-$\eta^5$-4,5,6,7-tetrahydroindenyl)]dichlorozirconium,

[4-($\eta^5$-2-indenyl)-2-isopropyl-4,7,7-trimethyl-$\eta^5$-4,5,6,7-tetrahydroindenyl)]dichlorozirconium,

[4-($\eta^5$-2-(4,5,6,7-tetrahydro)indenyl)-2-methyl-4,7,7-trimethyl-$\eta^5$-4,5,6,7-tetrahydroindenyl)]dichlorozirconium,

[4-($\eta^5$-2-indenyl)-2-butyl-4,7,7-trimethyl-$\eta^5$-4,5,6,7-tetrahydroindenyl)]dichlorozirconium,

[4-($\eta^5$-2-(4,5,6,7-tetrahydro)indenyl)-2-phenyl-4,7,7-trimethyl-$\eta^5$-4,5,6,7-tetrahydroindenyl)]dichlorozirconium,

[4-($\eta^5$-3'-isopropylcyclopentadienyl)-2-methyl-4,7,7-trimethyl-$\eta^5$-4,5,6,7-tetrahydroindenyl)]dichlorozirconium,

[4-($\eta^5$-4'-isopropylcyclopentadienyl)-2-methyl-4,7,7-trimethyl-$\eta^5$-4,5,6,7-tetrahydroindenyl)]dichlorozirconium,

[4-($\eta^5$-3'-isopropylcyclopentadienyl)-4,7,7-trimethyl-$\eta^5$-4,5,6,7-tetrahydrofluorenyl)]dichlorozirconium,

[4-($\eta^5$-4'-isopropylcyclopentadienyl)-4,7,7-trimethyl-$\eta^5$-4,5,6,7-tetrahydrofluorenyl)]dichlorozirconium,

[4-($\eta^5$-3'-isopropylcyclopentadienyl)-2-isopropyl-4,7,7-trimethyl-$\eta^5$-4,5,6,7-tetrahydrofluorenyl)]dichlorozirconium,

[4-($\eta^5$-4'-isopropylcyclopentadienyl)-2-isopropyl-4,7,7-trimethyl-$\eta^5$-4,5,6,7-tetrahydrofluorenyl)]dichlorozirconium,

[4-($\eta^5$-3'-butylcyclopentadienyl)-4,7,7-trimethyl-$\eta^5$-4,5,6,7-tetrahydroindenyl)]dichlorozirconium,

[4-($\eta^5$-4'-butylcyclopentadienyl)-4,7,7-trimethyl-$\eta^5$-4,5,6,7-tetrahydroindenyl)]dichlorozirconium,

[4-($\eta^5$-3'-butylcyclopentadienyl)-2-isopropyl-4,7,7-trimethyl-$\eta^5$-4,5,6,7-tetrahydroindenyl)]dichlorozirconium,

[4-($\eta^5$-4'-butylcyclopentadienyl)-2-isopropyl-4,7,7-trimethyl-$\eta^5$-4,5,6,7-tetrahydroindenyl)]dichlorozirconium,

[4-($\eta^5$-3'-butylcyclopentadienyl)-2-butyl-4,7,7-trimethyl-$\eta^5$-4,5,6,7-tetrahydroindenyl)]dichlorozirconium,

[4-($\eta^5$-4'-butylcyclopentadienyl)-2-butyl-4,7,7-trimethyl-$\eta^5$-4,5,6,7-tetrahydroindenyl)]dichlorozirconium,

[4-($\eta^5$-3',4'-dimethylcyclopentadienyl)-4,7,7-trimethyl-$\eta^5$-4,5,6,7-tetrahydroindenyl)]dichlorozirconium,

[4-($\eta^5$-3',4'-diisopropylcyclopentadienyl)-4,7,7-trimethyl-$\eta^5$-4,5,6,7-tetrahydroindenyl)]dichlorozirconium,

[4-($\eta^5$-3',4'-diphenylcyclopentadienyl)-2-isopropyl-4,7,7-trimethyl-$\eta^5$-4,5,6,7-tetrahydroindenyl)]dichlorozirconium,

[4-($\eta^5$-3',4'-diethylcyclopentadienyl)-2-isopropyl-4,7,7-trimethyl-$\eta^5$-4,5,6,7-tetrahydroindenyl)]dichlorozirconium,

[4-($\eta^5$-3',4'-dibutylcyclopentadienyl)-2-isopropyl-4,7,7-trimethyl-$\eta^5$-4,5,6,7-tetrahydroindenyl)]dichlorozirconium,

[4-($\eta^5$-3'-methyl-4'-phenylcyclopentadienyl)-4,7,7-trimethyl-$\eta^5$-4,5,6,7-tetrahydroindenyl)]dichlorozirconium,

[4-($\eta^5$-3'-ethyl-4'-phenylcyclopentadienyl)-4,7,7-trimethyl-$\eta^5$-4,5,6,7-tetrahydroindenyl)]dichlorozirconium,

[4-($\eta^5$-3'-isopropyl-4'-phenylcyclopentadienyl)-4,7,7-trimethyl-$\eta^5$-4,5,6,7-tetrahydroindenyl)]dichlorozirconium,

[4-($\eta^5$-3'-methyl-4'-isopropylcyclopentadienyl)-4,7,7-trimethyl-$\eta^5$-4,5,6,7-tetrahydroindenyl)]dichlorozirconium,

[4-($\eta^5$-3'-methyl-4'-naphthylcyclopentadienyl)-4,7,7-trimethyl-$\eta^5$-4,5,6,7-tetrahydroindenyl)]dichlorozirconium, and

[4-($\eta^5$-3'-methyl-4'-butylcyclopentadienyl)-4,7,7-trimethyl-$\eta^5$-4,5,6,7-tetrahydroindenyl)]dichlorozirconium.

17. The process as claimed in claim 1, wherein the compound is selected from the group consisting of

[$\eta^5$-9-($\eta^5$-cyclopentadienyl)tricyclo[6.1.1.0$^{2,6}$]deca-2,5-dienyl]dichlorotitanium,

[$\eta^5$-9-($\eta^5$-cyclopentadienyl)tricyclo[6.1.1.0$^{2,6}$]deca-2,5-dienyl]dichlorozirconium,

[$\eta^5$-7-methyl-9-($\eta^5$-cyclopentadienyl)tricyclo[6.1.1.0$^{2,6}$]deca-2,5-dienyl]dichlorotitanium,

[$\eta^5$-7-methyl-9-($\eta^5$-cyclopentadienyl)tricyclo[6.1.1.0$^{2,6}$]deca-2,5-dienyl]dichlorozirconium,

[$\eta^5$-9-methyl-9-($\eta^5$-cyclopentadienyl)tricyclo[6.1.1.0$^{2,6}$]deca-2,5-dienyl]dichlorotitanium,

[$\eta^5$-9-methyl-9-($\eta^5$-cyclopentadienyl)tricyclo[6.1.1.0$^{2,6}$]deca-2,5-dienyl]dichlorozirconium,

[$\eta^5$-10-($\eta^5$-cyclopentadienyl)tricyclo[5.2.1.0$^{2,6}$]deca-2,5-dienyl]dichlorotitanium,

[$\eta^5$-10-($\eta^5$-cyclopentadienyl)tricyclo[5.2.1.0$^{2,6}$]deca-2,5-dienyl]dichlorozirconium,

[$\eta^5$-10-methyl-10-($\eta^5$-cyclopentadienyl)tricyclo[5.2.1.0$^{2,6}$]deca-2,5-dienyl]dichlorotitanium,

[$\eta^5$-10-methyl-10-($\eta^5$-cyclopentadienyl)tricyclo[5.2.1.0$^{2,6}$]deca-2,5-dienyl]dichlorozirconium,

[$\eta^5$-9-($\eta^5$-cyclopentadienyl)tricyclo[5.2.2.0$^{2,6}$]undeca-2,5-dienyl]dichlorotitanium,

[$\eta^5$-9-($\eta^5$-cyclopentadienyl)tricyclo[5.2.2.0$^{2,6}$]undeca-2,5-dienyl]dichlorozirconium,

[$\eta^5$-9-methyl-9-($\eta^5$-cyclopentadienyl)tricyclo[5.2.2.0$^{2,6}$]-undeca-2,5-dienyl]dichlorotitanium,

[$\eta^5$-9-methyl-9-($\eta^5$-cyclopentadienyl)tricyclo[5.2.2.0$^{2,6}$]-undeca-2,5-dienyl]dichlorozirconium,

[$\eta^5$-10-($\eta^5$-3'-methylcyclopentadienyl)tricyclo[5.2.1.0$^{2,6}$]-deca-2,5-dienyl]dichlorotitanium,

[$\eta^5$-10-($\eta^5$-3'-methylcyclopentadienyl)tricyclo[5.2.1.0$^{2,6}$]-deca-2,5-dienyl]dichlorozirconium,

[$\eta^5$-10-methyl-10-($\eta^5$-3'-methylcyclopentadienyl)tricyclo[5.2.1.0$^{2,6}$]deca-2,5-dienyl]dichlorotitanium,

[$\eta^5$-10-methyl-10-($\eta^5$-3'-methylcyclopentadienyl)tricyclo[5.2.1.0$^{2,6}$]deca-2,5-dienyl]dichlorozirconium,

[$\eta^5$-4-methyl-10-($\eta^5$-3'-methylcyclopentadienyl)tricyclo[5.2.1.0$^{2,6}$]deca-2,5-dienyl]dichlorotitanium,

[η$^5$-4-methyl-10-(η$^5$-3'-methylcyclopentadienyl)tricyclo[5.2.1.0$^{2,6}$]deca-2,5-dienyl]dichlorozirconium,

[η$^5$-4,10-dimethyl-10-(η$^5$-3'-methylcyclopentadienyl)tricyclo[5.2.1.0$^{2,6}$]deca-2,5-dienyl]dichlorotitanium,

[η$^5$-4,10-dimethyl-10-(η$^5$-3'-methylcyclopentadienyl)tricyclo[5.2.1.0$^{2,6}$]deca-2,5-dienyl]dichlorozirconium,

[η$^5$-5-methyl-10-(η$^5$-3'-methylcyclopentadienyl)tricyclo[5.2.1.0$^{2,6}$]deca-2,5-dienyl]dichlorotitanium,

[η$^5$-5-methyl-10-(η$^5$-3'-methylcyclopentadienyl)tricyclo[5.2.1.0$^{2,6}$]deca-2,5-dienyl]dichlorozirconium,

[η$^5$-5,10-dimethyl-10-(η$^5$-3'-methylcyclopentadienyl)tricyclo[5.2.1.0$^{2,6}$]deca-2,5-dienyl]dichlorotitanium, and

[η$^5$-5,10-dimethyl-10-(η$^5$-3'-methylcyclopentadienyl)tricyclo[5.2.1.0$^{2,6}$]deca-2,5-dienyl]dichlorozirconium.

18. The process as claimed in claim 1, wherein said stereorigid metallocene compound contain as ligands, at least two substituted or unsubstituted cyclopentadienyl groups bonded to one another via a monocyclic ring system, in which at least one cyclopentadienyl group is fused to the monocyclic ring system and one cyclopentadienyl group is a substituent on the monocyclic ring system.

19. The process as claimed in claim 1, wherein said stereorigid metallocene compound contains as ligands, at least two substituted or unsubstituted cyclopentadienyl groups bonded to one another via a polycyclic ring system, in which at least one cyclopentadienyl group is fused to the polycyclic ring system.

* * * * *